US009441222B2

(12) United States Patent
Weijzen et al.

(10) Patent No.: US 9,441,222 B2
(45) Date of Patent: Sep. 13, 2016

(54) MIRNA FOR TREATING DISEASES AND CONDITIONS ASSOCIATED WITH NEO-ANGIOGENESIS

(71) Applicant: InteRNA Technologies B.V., Nijmegen (NL)

(72) Inventors: Sanne Weijzen, Bilthoven (NL); Roeland Quirinus Jozef Schaapveld, Bussum (NL); Meriem Bourajjaj, Almere (NL); Rick Jan Van Haastert, Amersfoot (NL); Arjan Willem Griffioen, Heemstede (NL); Judith Rosina Van Biejnum, Hilversum (NL); Edwin Pieter Johan Gerard Cuppen, Bilthoven (NL); Eugene Berezikov, Haren (NL); Andreas Alphons Franciscus Ludovicus Van Piujenbroek, Boxtel (NL); Willemijn Maria Gommans, Voorschoten (NL); Negar Babae, Utrecht (NL); Petronella Innocentia Van Noort, Megen (NL)

(73) Assignee: INTERNA TECHNOLOGIES B.V. (NL)

( * ) Notice: Subject to any disclaimer, the term of this patent is extended or adjusted under 35 U.S.C. 154(b) by 16 days.

(21) Appl. No.: 13/933,526

(22) Filed: Jul. 2, 2013

(65) Prior Publication Data

US 2014/0005251 A1 Jan. 2, 2014

Related U.S. Application Data

(63) Continuation of application No. PCT/NL2012/050011, filed on Jan. 10, 2012.

(60) Provisional application No. 61/431,656, filed on Jan. 11, 2011, provisional application No. 61/431,667, filed on Jan. 11, 2011, provisional application No. 61/521,917, filed on Aug. 10, 2011, provisional application No. 61/521,931, filed on Aug. 10, 2011, provisional application No. 61/522,346, filed on Aug. 11, 2011, provisional application No. 61/540,640, filed on Sep. 29, 2011.

(30) Foreign Application Priority Data

Jan. 11, 2011 (EP) ...................................... 11150645

(51) Int. Cl.
*C12N 15/113* (2010.01)
*C12Q 1/68* (2006.01)

(52) U.S. Cl.
CPC ........... *C12N 15/113* (2013.01); *C12Q 1/6883* (2013.01); *C12N 2310/141* (2013.01); *C12N 2320/10* (2013.01); *C12N 2320/30* (2013.01); *C12N 2320/31* (2013.01)

(58) Field of Classification Search
USPC ........... 435/6.1, 91.1, 91.31, 455, 6.12, 1.1; 514/44; 536/23.1, 24.5
See application file for complete search history.

(56) References Cited

U.S. PATENT DOCUMENTS

| | | | |
|---|---|---|---|
| 2006/0185027 A1 | 8/2006 | Bartel et al. | |
| 2006/0247193 A1 | 11/2006 | Taira et al. | |
| 2009/0004668 A1* | 1/2009 | Chen et al. ........................ 435/6 |
| 2009/0281167 A1* | 11/2009 | Shen ..................... C12N 15/113 514/44 A |
| 2015/0275299 A1 | 10/2015 | Xu | |

FOREIGN PATENT DOCUMENTS

| | | |
|---|---|---|
| EP | 2112235 B1 | 10/2009 |
| EP | 2061482 B1 | 1/2015 |
| JP | 2011188849 A | 9/2011 |
| WO | 03029459 A2 | 4/2003 |
| WO | 03070912 A2 | 8/2003 |
| WO | 2004076622 A2 | 9/2004 |
| WO | 2005013901 A2 | 2/2005 |
| WO | 2005078139 A2 | 8/2005 |
| WO | 2006111512 A2 | 10/2006 |
| WO | 2006137941 A1 | 12/2006 |
| WO | 2007081680 A2 | 7/2007 |
| WO | 2007081720 A2 | 7/2007 |
| WO | 2007081740 A2 | 7/2007 |
| WO | 2007090073 A2 | 8/2007 |
| WO | 2007103808 A2 | 9/2007 |
| WO | 2007109236 A2 | 9/2007 |
| WO | 2008025073 A1 | 3/2008 |
| WO | 2008103755 A1 | 8/2008 |
| WO | 2008154098 A2 | 12/2008 |
| WO | 2009008720 A2 | 1/2009 |
| WO | 2009043353 A2 | 4/2009 |
| WO | 2009044899 A2 | 4/2009 |
| WO | 2009045469 A2 | 4/2009 |
| WO | 2010014636 A1 | 2/2010 |
| WO | 2010048549 A2 | 4/2010 |
| WO | 2010056737 A2 | 5/2010 |
| WO | 2010097471 A2 | 9/2010 |

(Continued)

OTHER PUBLICATIONS

Doench et al, Genes & Development, vol. 17, pp. 438-442, 2003.*

(Continued)

*Primary Examiner* — Jane Zara

(74) *Attorney, Agent, or Firm* — Morgan, Lewis & Bockius LLP

(57) ABSTRACT

The invention relates to the diagnostic and therapeutic uses of a miRNA molecule, an equivalent or a source thereof in a disease and condition associated with neo-angiogenesis.

5 Claims, 16 Drawing Sheets

(56) References Cited

FOREIGN PATENT DOCUMENTS

| WO | 2011028550 A1 | 3/2011 |
|---|---|---|
| WO | 2011150855 A1 | 12/2011 |
| WO | 2012027558 A2 | 3/2012 |

OTHER PUBLICATIONS

Opalinska et al, Nature Rev., vol. 1, pp. 503-514, 2002.*
Jang et al, Expert Rev. Medical Devices, vol. 1, No. 1, pp. 127-138, 2004.*
Paroo et al. Trends in Biotech., vol. 22, No. 8, pp. 390-394, 2004.*
Bushati et al, Current Opin. Neurobiol., vol. 18, pp. 292-296, 2008.*
Vasdudevan et al, Science, vol. 318, pp. 1931-1934, 2007.*
Cheng, A., et al., Antisense Inhibition of Human miRNAs and Indications for an Involvement of miRNA in Cell Growth and Apoptosis, Nucleic Acids Research, vol. 33, No. 4, pp. 1290-1297 (Feb. 10, 2005).
Chou, Y., et al., "EGFR Promotes Lung Tumorigenesis by Activating miR-7 through a Ras/ERK/Myc Pathway That Targets the Ets2 Transcriptional Repressor ERF, Tumor and Stem Cell Biology," vol. 70, No. 21, pp. 8822-8831 (Nov. 1, 2010).
Foekens, J., et al., "Four miRNAs Associated with Aggressivenes of Lymph Node-Negative, Estrogen Receptor-Positive Human Breast Cancer," PNAS, vol. 105, No. 35, pp. 13021-13026 (Sep. 2, 2008).
Jiang, Lu., et al., "MicroRNA-7 Targes IGF1R (Insulin-Like Growth Factor 1 Receptor) in Tongue Squamous Cell Carcinoma Cells," Author Manuscript, Biochem. J., vol. 432, No. 1, pp. 199-205 (Oct. 25, 2010).
Junn, E., et al., "Repression of a α-Synuclein Expression and Toxicity by microRNA-7," PNAS, vol. 106, No. 31, pp. 13052-13057 (Aug. 4, 2009).
Kefas, B., et al., "MicroRNa-7 Inhibits the Epiderman Growth Factor Receptor and the Akt Pathway and Is Down-Regulated in Glioblastoma," Cancer Res., vol. 68, No. 10, pp. 3566-3572 (May 15, 2008).
Lai, Eric C., "Micro RNAs are Complementary to 3' UTR Sequence Motifs that Mediate Negative Post-Transcriptional Regulation," Nature Genetics, vol. 30, pp. 363-364, published online Mar. 18, 2002 (Apr. 2002).
Li, X., et al., "A microRNA Mediates EGF Receptor Signaling and Promotes Photoreceptor Differentiation in the Drosophila Eye," Cell, vol. 123, pp. 1267-1277 (Dec. 29, 2005).
Miguel, M., et al., "Immunohistochemical Comparative Analysis of Transforming Growth Factor α, Epidermal Growth Factor, and Epidermal Growth Factor Receptor in Normal, Hyperplastic and Neoplastic Human Prostates," Cytokine, vol. 11, No. 9, pp. 722-727 (Sep. 1999).
Ogino A., et al., "Emergency of Epidermal Growth Factor Receptor T790M Mutation during Chronic Exposure to Gefitinib in a Non-Small Cell Lung Cancer Cell Line," Cancer Res., vol. 67, No. 16, pp. 7807-7814 (Aug. 15, 2007).
Rai, K., "Liposomal Delivery of MicroRNA-7-Expressing Plasmid Overcomes Epidermal Growth Facator Receptor Tyrosine Kinase Inhibitor-Resistance in Lung Cancer Cells," Mol Cancer Ther., vol. 10, pp. 1720-1727 (Jun. 28, 2011).
Rai Kammei, Proc Am Assco Cancer Res; Abstract 1396 AACR Annual Meeting Apr. 18-22, 2009.
Rai Kammei, Proc Am Asso Cancer Res; Abstract 1158 AACR Annual Meeting Apr. 2-6, 2011.
Rai Kammei, Proc Am Asso Cancer Res; Abstract 4041 AACR Annual Meeting Apr. 17-21, 2010.
Reddy, S., et al., "MicroRNA-7, a Homeobox D10 Target, Inhibits the p21-Aactivated Kinase 1 and Regulates its Functions," Author Manuscript, Cancer Res., vol. 68, No. 20, pp. 8195-8200 (Oct. 15, 2008).
Saydem, O., et al., "miRNA-7 Attenuation in Schwannoma Tumors Stimulates Growth by Upregulating These Oncogenic Signaling Pathways," Cancer Research, vol. 71, No. 3, pp. 852-861 (Feb. 1, 2011).
Tsuda, N., et al., "Synthetic microRNA and Double-Stranded RNA Targeting the 3'-untranslated Region of HER-2/neu mRNA Inhibit HER-2 Protein Expression in Ovarian Cancer Cells," International Journal of Oncology, vol. 27, pp. 1299-1306 (Apr. 22, 2005).
Vardy, D., et al., "Induction of Autocrine Epidermal Growth Factor Receptor Ligands in Human Keratinocytes by Insulin/Insulin-Like Growth Factor-1," Journal of Cellular Physiology, vol. 163, pp. 257-265 (May 1995).
Veerla, S., et al., "MiRNA Expression in Urothelial Carcinomas: Important Roles of miR-10a, miR-222, miR-125b, miR-7 and miR-452 for Tumor Stage and Metastasis, and Frequent Homozygous Losses of miR-31," Int. J. Cancer, vol. 124, pp. 2236-2242, published online Nov. 26, 2008, (May 1, 2009).
Webster, R. J., et al., "Regulation of Epidermal Growth Factor Receptor Signaling in Human Cancer Cells by MicroRNa-7," The Journal of Biological Chemistry, vol. 284, No. 9, pp. 5731-5741 (Feb. 27, 2009).
Wilson, S. E., "EGF, EGF Receptor, Basic FGF, TGF Beta-1, and IL-1 Alpha mRNA in Human Corneal Epithelial Cells and Stromal Fibroblasts," Investigative Ophthalmology & Visual Science, vol. 33, No. 5, (Apr. 1992).
Yano, S., et al., "Distribution and Function of EGFR in Human Tissue and the Effect of EGFR Tyrosine Kinase Inhibition," Anticancer Research, vol. 23.5A, pp. 3639-3640 (Sep.-Oct. 2003).
Balmer, L., et al., "Identification of a Novel AU-Rich Element in the 3' Untranslated Region of Epidermal Growth Factor Receptor mRNA That is the Target for Regulated RNA-Binding Proteins," Molecular and Cellular Biology, vol. 21, No. 6, pp. 2070-2084 (Mar. 2001).
Grimson, A., et al., "MicroRNA Targeting Specificity in Mammals: Determinants Beyond Seed Pairing," Mol. Cell., vol. 27, No. 1, pp. 91-105 (Jul. 6, 2007).
Guix, M., et al., Acquired Resistance to EGFR Tyrosine Kinase Inhibitors in Cancer Cells is Meciated by Loss of IGF-Binding Proteins, Journal of Clinical Investigation, vol. 118, No. 7, pp. 2609-2619 (Jul. 2008).

* cited by examiner

Fig. 12A  Controls vs. miR-7
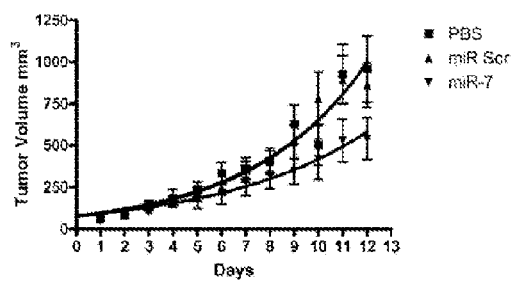
Fig. 12B  Controls vs. miR-574-5p
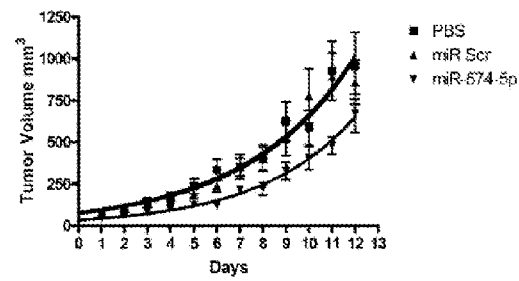
Fig. 12C  Controls vs. miR-27a
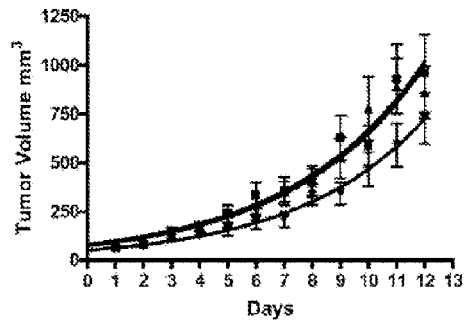
Fig. 12D  Controls vs. si-VEGFR2
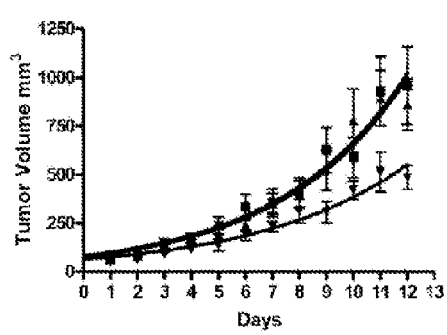

MIRNA FOR TREATING DISEASES AND CONDITIONS ASSOCIATED WITH NEO-ANGIOGENESIS

CROSS REFERENCE

This application is a continuation of international application PCT/NL2012/050011, filed Jan. 10, 2012, which claims priority to European application No. 11150645.7, filed Jan. 11, 2011, and U.S. provisional applications 61/431,656 and 61/431,667, filed Jan. 11, 2011, and 61/521/917 and 61/521,931, filed Aug. 10, 2011, and 61/522,346, filed Aug. 11, 2011, and 61/540,640, filed Sep. 29, 2011.

FIELD OF THE INVENTION

The invention relates to a diagnostic use of a miRNA molecule, equivalent or source thereof and therapeutic use of said miRNA molecule, equivalent or source thereof in diseases and conditions associated with neo-angiogenesis.

BACKGROUND OF THE INVENTION

Angiogenesis is defined as the growth of new microvessels out of pre-existing capillaries. It may be distinguished from vasculogenesis, which refers to neovascularization during embryonal growth in which also larger vessels are formed and where endothelial precursor cells (EPCs) cells participate. However, there is evidence that EPCs can play a (minor) role in tumor angiogenesis as well. It can also be distinguished from arteriogenesis which mainly involves the maturation and growth of collateral blood vessels (Asahara S. et al 1999, Carmeliet P. 2000, and Helisch A. et al 2003). Angiogenesis is the main mechanism by which new blood vessels are formed during physiological processes like wound healing, inflammation, and the female reproductive cycle. In addition, angiogenesis is involved in various disorders including age-related macular degeneration, rheumatoid arthritis, endometriosis, and cancer (Carmeliet P. et al 2005, and Griffioen A. W. et al 2000). A century ago, it was observed that angiogenesis occurs around tumors and further research led to the hypothesis that tumors produce pro-angiogenesis factors to stimulate neovascularisation (Carmeliet P. et al 2000, Folkman J. et al 1971). The importance of angiogenesis in tumor growth was initially hypothesized in 1971, when Judah Folkman theorized that solid tumors possess limited resources that the many actively proliferating cancer cells fight for. Ever since, tumor angiogenesis research has focused on understanding of and interfering with the processes by which tumor cells promote the growth of new blood vessels (Folkman J. et al 2007, and Ribatti D. et al 2000). The process of tumor angiogenesis is primarily activated when a growing tumor mass surpasses the maximal volume that can be maintained by diffusion of oxygen and nutrients (Carmeliet P. 2000). The hypoxic environment will cause the tumor cells to undergo the angiogenic switch leading to increased production of pro-angiogenesis proteins like the vascular endothelial growth factor (VEGF) (Folkman J. et al 1995, Folkman J. et al 2002, and Hanahan D. et al 1996). These pro-angiogenic proteins activate endothelial cells in nearby vessels. At the same time, an increased activity of different proteolytic enzymes results in degradation of the basal membrane and detachment of cell-cell contacts, which facilitate migration and invasion of EC (endothelial cells) into the surrounding matrix and towards the tumor (Carmeliet P. 2000, and Griffioen A. W. et al 2000). The proteolytic cleavage of the extracellular matrix also allows migration of the activated endothelial cells towards chemotactic signals that originate from the tumor tissue. These signals are sensed by endothelial cells and the subsequent migration and proliferation of endothelial cells results in the formation of vessel-like structures (Adams R. H. et al 2007, and Carmeliet P. 2000). Despite its irregular and disorganized structure, this network is capable of providing the growing tumor mass with all the required metabolites. In addition, the vascular bed provides the tumor cells with the opportunity to enter the circulation and form distant metastases (Folkman J. et al, 2002). While different cell types contribute to neovascularization, the endothelial cell is generally acknowledged to be the central player in the angiogenesis process. In response to different triggers, these cells display a variety of functions, including extracellular matrix remodeling, proliferation, and migration. All these functions require the expression of specific molecules, and proper execution of this complex process relies on endothelial cell flexibility to readily adjust the transcriptome and proteome to comply with the functional demands. Besides the more classical mechanisms, like regulation of gene promoter activity and altered protein turn-over, it has now become evident that cells also use small non-coding RNA molecules to govern gene expression. One class of these RNA molecules, microRNAs (miRNAs), acts as molecular switches that can redirect the expression profile of a cell. Evidence is increasing that these miRNAs fulfill an important role in endothelial gene expression regulation during tumor angiogenesis (Heusschen R, et al 2010). Many miRNAs show organ-specific expression patterns suggesting cell type-specific functions (Chen C. Z. et al 2004, Poy M. N. et al 2004, and van Rooij E. et al 2007). Consequently, dysregulation of miRNA expression and function may lead to human diseases (Chang T. C. et al 2007). The first large-scale analysis of miRNA expression in endothelial cells (ECs) was carried out in HUVECs (Human Umbilical Venal Endothelial Cells) and identified 15 highly expressed miRNAs with receptors of angiogenic factors (e.g. Flt-1, Nrp-2, Fgf-R, c-Met, and c-kit) as putative mRNA targets, according to prediction algorithms (Polisenol L. et al 2006). Additional studies also profiled the expression of miRNAs in ECs (Kuehbacher A. et al 2007, and Suarez Y. et al 2007). The highly expressed miRNAs that were common in at least 2 of the 3 studies, included miRNA-15b, -16, -20, -21, -23a, -23b, -24, -29a and -b, -31, -99a, -100, -103, -106, -125a, -125b, -126, -130a, -181a, -191, -221, -222, -320, let-7, let-7b, let-7c, and let-7d (Kuehbacher A. et al 2007, Polisenol L. et al 2006, and Suarez Y. et al 2007). However, their specific targets and functions in ECs related to angiogenesis have only been characterized for a few of them.

A study showed that transfection of HUVECs with miRNA-221/222 inhibits tube formation, migration, and wound healing in response to stem cell factor (Polisenol L. et al 2006). This and other studies suggest an antiangiogenic action for these miRNAs and they might be a potential tool to block angiogenesis. However, it is important to note that miR221/222 can also promote cancer cell proliferation through the regulation of p27(Kip1) tumor suppressor (Le Sage C. et al 2007) indicating that the regulation of proliferation by these miRNAs appears cell type specific. Therefore, cell specific targeting with miRNAs is an important area of investigation to be developed. Other miRNAs expressed in ECs, let-7f and miRNA-27b, have been shown to exert proangiogenic effects, as revealed by the blockade of in vitro angiogenesis with 2'-O-methyl oligonucleotides inhibitors (Kuehbacher A. et al 2007) although their targets in ECs have not yet been characterized.

The best-characterized EC-specific miRNA is miRNA-126 (Fish J. E. et al 2008, Harris T. A. et al 2008, and Wang S. et al 2008). It promotes growth factor (VEGF/FGF Vascular Endothelial Growth Factor/Fibroblast Growth Factor) signaling, angiogenesis, and vascular integrity by inhibiting endogenous repressors of growth factors within ECs (Fish J. E. et al 2008, and Wang S. et al 2008). These findings illustrate that a single miRNA can regulate vascular integrity and angiogenesis, providing a new target for either pro- or antiangiogenic therapies.

A very recent study (Anand S. et al 2010) concludes that miRNA-132 acts as an angiogenic switch by suppressing endothelial p120RasGAP (p120Ras GTPase Activating Protein) expression, leading to Ras activation and the induction of neovascularization, whereas the application of anti miRNA-132 inhibits neovascularization by maintaining vessels in the resting state.

Additionally, several other findings which are not described here provide proof-of-concept for miRNAs as a powerful and highly specific anti-angiogenic therapeutic modality.

There are currently several angiostatic compounds in the market and many are in mid- and late stage clinical testing. Since approximately 5 years, medication based on anti-angiogenesis (e.g. Avastin) has been approved for the clinic. More recently, small molecule RTKI's (Receptor Tyrosine Kinase Inhibitor) are used, e.g. Sunitinib. However, by their nature—targeting essentially tumor driven processes—they evoke clinical resistance. Although there is definitely some prolongation of survival in patient cohorts for some cancer types, the benefit can be considered moderate. In addition to the cancer treatment, three anti-angiogenesis therapies are currently used for the treatment of patients with eye diseases such as wet age-related macular degeneration (AMD): pegaptanib (Macugen, Pfizer), ranibizumab (Lucentis, Novartis), and bevacizumab (Avastin, Roche). Here also, although there is definitely some visual acuity improvement, the benefit is still considered as limited.

Therefore, there is a clear need for better diagnostic markers for neo-angiogenesis, as well as better strategies of therapeutic angiogenesis inhibition.

DESCRIPTION OF THE INVENTION

The invention encompasses several uses of a miRNA molecule, equivalent, mimic, isomiR or antagomir or source thereof as identified herein. The invention also encompasses each of the newly identified miRNA molecules equivalent, mimic, isomiR or antagomir per se.

In a first aspect, there is provided a miRNA-9, miRNA-574, miRNA-7, miRNA-190b and/or miRNA-142 molecule, an equivalent, mimic, isomiR, or a source thereof or a composition comprising said miRNA molecule miRNA-9, miRNA-574, miRNA-7, miRNA-190b and/or miRNA-142, said equivalent or said source thereof, preferably for use as a medicament for preventing, treating, reverting, curing and/or delaying neo-angiogenesis or a disease or a condition associated with neo-angiogenesis. MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA equivalent, a miRNA mimic or a miRNA isomiR, or a mimic or an isomiR or a miRNA source is to be used for each of the identified miRNAs or miRNA equivalent or miRNA sources of this application: miRNA-574, miRNA-7, miRNA-26b, miRNA-27a, miRNA-92a, miRNA-221, miRNA-222, miRNA-145, let7a1, miRNA-190b, miRNA-142, miRNA-9 and sources thereof. Preferred mature or mimic sequences (as identified in Table 5 as SEQ ID NO: 22-52), seed sequences (as identified in Tables 5 and 7 as SEQ ID NO: 348-378, 61-115 and 379-381), isomiR sequences (as identified in Table 7 as SEQ ID NO: 116-304 and 382-396) or source sequences (as identified in Tables 4 (RNA precursor as SEQ ID NO: 1-21) or 6 (DNA encoding a RNA precursor as SEQ ID NO: 53-60)) of said miRNA molecule or equivalent thereof respectively are identified in corresponding tables.

Within the whole text of the application unless otherwise indicated, a miRNA may also be named a miRNA molecule, a miR, or an equivalent thereof or a source or a precursor thereof. A preferred equivalent is an isomiR or a mimic. Each sequence identified herein may be identified as being SEQ ID NO as used in the text of the application or as corresponding SEQ ID NO in the sequence listing.

MiRNA-132, miRNA-126 and miRNA-21 are also referred to in the present invention. They are the only miRNA molecules of this invention whose expression is not to be up-regulated/over-expressed/increased and/or whose activity is not to be increased in order to be used in therapeutic applications as identified herein. In contrast, the endogenous expression of these miRNA molecules needs to be down-regulated/decreased and/or an activity of such miRNA molecule needs to be decreased or reduced or inhibited to obtain a therapeutically desirable effect. This is preferably carried out as explained later herein using an antagomir. Therefore, in the invention when reference is made to any of these miRNA molecules in a therapeutic use, one always refers to a use of an antagomir of a miRNA-132, miRNA-126 or miRNA-21 molecule or of an equivalent of an antagomir of these miRNAs or a source of an antagomir of these miRNAs. Accordingly, when one refers to an antagomir, one always refers to a use of an antagomir of a miRNA-132, miRNA-126 and miRNA-21 molecule or an equivalent or a source thereof as indicated herein. Each of the definitions given herein concerning a miRNA molecule or a miRNA equivalent or a miRNA source may also apply for any of the miRNA molecule to be used as an antagomir as identified in this paragraph. Each definition given herein concerning q given antagomir of a miRNA molecule also holds for other antagomir of a distinct miRNA molecule, each as defined herein.

In the context of the invention, a miRNA molecule or an equivalent or a mimic or an antagomir or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or body fluids (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic or an antagomir thereof may be a single stranded or double stranded RNA molecule.

Preferably a miRNA molecule or an equivalent, or a mimic thereof is from 6 to 30 nucleotides in length, preferably 12 to 30 nucleotides in length, preferably 15 to 28 nucleotides in length, more preferably said molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Preferably an antagomir of a miRNA molecule is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA molecule or equivalent or mimic or isomiR thereof comprises at least 6 of the 7 nucleotides present in the seed sequence of said miRNA molecule or equivalent or mimic or isomiR thereof (Tables 5 and 7 show preferred seed sequence of each of the miRNAs molecule identified herein as SEQ ID NO: 348-378, 61-115 and 379-381). Preferably in this embodiment, a miRNA molecule or an equivalent or a mimic or isomiR thereof is from 6 to 30 nucleotides in length and more preferably comprises at least 6 of the 7 nucleotides present in the seed sequence of said miRNA molecule or equivalent thereof. Even more preferably a miRNA molecule or an equivalent or a mimic or isomiR thereof is from 15 to 28 nucleotides in length and more preferably comprises at least 6 of the 7 nucleotides present in the seed sequence, even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-574 molecule or equivalent or mimic or isomiR thereof comprises at least 6 of the 7 nucleotides present in the seed sequence identified as SEQ ID NO: 353, 354, 78, 79, 80, 82, 83, and/or 84 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-7 molecule or equivalent or mimic or isomiR thereof comprises at least 6 of the 7 nucleotides present in the seed sequence identified as SEQ ID NO: 348, 349, 350, 62, 63, 64, 65, 66, 67, 68, 69, 71, 72, 73, and/or 74 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-190b molecule or equivalent or mimic or isomiR thereof comprises at least 6 of the 7 nucleotides present in the seed sequence identified as SEQ ID NO: 374 and/or 96 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-142 molecule or equivalent or mimic or isomiR thereof comprises at least 6 of the 7 nucleotides present in the seed sequence identified as SEQ ID NO: 375, 376, 97, 99, 100, 101, 102, 103, 104, 105, 106, 107, 108, 109, and/or 110 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-9 molecule or equivalent or mimic or isomiR thereof comprises at least 6 of the 7 nucleotides present in the seed sequence identified as SEQ ID NO: 377, 378, 114, 115, 379, 380 and/or 381 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a more preferred embodiment, a miRNA-9 molecule or equivalent or mimic or isomiR thereof is identified as a miRNA-9* molecule or equivalent or mimic or isomiR thereof and comprises at least 6 of the 7 nucleotides present in the seed sequence identified as SEQ ID NO: 378, 114 and/or 115 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In another preferred embodiment, a miRNA molecule or an equivalent or mimic or isomiR thereof comprises at least 6 of the 7 nucleotides present in a given seed sequence as identified in Tables 5 and 7 as SEQ ID NO: 348-378, 61-115 and 379-381 and has at least 70% identity over the whole mature sequence as identified in Table 5 (Table 5 shows preferred mature or mimic sequences of each of the miRNAs identified herein as SEQ ID NO: 22-52). Preferably, identity is at least 75%, 80%, 85%, 90%, 95%, 97%, 98%, 99% or 100%.

Accordingly a preferred miRNA-574 molecule or equivalent or mimic or isomiR thereof comprises at least 6 of the 7 nucleotides present in the seed sequence identified as SEQ ID NO: 353, 354, 78, 79, 80, 82, 83, and/or 84 and/or has at least 70%, 75%, 80%, 85%, 90%, 95%, 97%, 98%, 99% or 100% identity over SEQ ID NO: 27, 28, 181, 182, 183, 184, 185, 186, 187, 188, 189, 190, 191, 192, 193, 194, 195, 196, 197, 198, 199, 200, 201, 202, 203, 204 and/or 205.

Accordingly a preferred miRNA-7 molecule or equivalent or mimic or isomiR thereof comprises at least 6 of the 7 nucleotides present in the seed sequence identified as SEQ ID NO: 348, 349, 350, 62, 63, 64, 65, 66, 67, 68, 69, 71, 72, 73 and/or 74 and/or has at least 70%, 75%, 80%, 85%, 90%, 95%, 97%, 98%, 99% or 100% identity over SEQ ID NO: 22, 23, 24, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, and/or 177.

Accordingly a preferred miRNA-190b molecule or equivalent or mimic or isomiR thereof comprises at least 6 of the 7 nucleotides present in the seed sequence identified as SEQ ID NO: 374 and/or 96 and/or has at least 70%, 75%, 80%, 85%, 90%, 95%, 97%, 98%, 99% or 100% identity over SEQ ID NO: 48, 234, 235, 236, 237, 238, 239 and/or 240.

Accordingly a preferred miRNA-142 molecule or equivalent or mimic or isomiR thereof comprises at least 6 of the 7 nucleotides present in the seed sequence identified as SEQ ID NO: 375, 376, 97, 99, 100, 101, 102, 103, 104, 105, 106, 107, 108, 109, and/or 110 and/or has at least 70%, 75%, 80%, 85%, 90%, 95%, 97%, 98%, 99% or 100% identity over SEQ ID NO: 49, 50, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288 and/or 289.

Accordingly a preferred miRNA-9 molecule or equivalent or mimic or isomiR thereof comprises at least 6 of the 7 nucleotides present in the seed sequence identified as SEQ ID NO: 377, 378, 114, 115, 379, 380 and/or 381 has at least 70%, 75%, 80%, 85%, 90%, 95%, 97%, 98%, 99% or 100% identity over SEQ ID NO: 51, 52, 290, 291, 291, 293, 294, 295, 296, 297, 298, 299, 300, 301, 302, 303, 304, 382, 383, 384, 385, 386, 387, 388, 389, 390, 391, 392, 393, 394, 395 and/or 396.

In a more preferred embodiment, a miRNA-9 molecule or equivalent or mimic or isomiR thereof is identified as a miRNA-9* molecule or equivalent or mimic or isomiR thereof and comprises at least 6 of the 7 nucleotides present in the seed sequence identified as SEQ ID NO: 378, 114 and/or 115 has at least 70%, 75%, 80%, 85%, 90%, 95%, 97%, 98%, 99% or 100% identity over SEQ ID NO: 52, 293, 294, 295, 296, 297, 298, 299, 300, 301, 302, 303 and/or 304.

Preferably in this embodiment, a miRNA molecule or an equivalent or a mimic or an isomiR thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more, comprises at least 6 of the 7 nucleotides present in a given seed sequence as identified in Tables 5 and 7 as SEQ ID NO: 348-378, 61-115 and 379-381 and has at least 70% identity over the whole mature sequence as identified in Table 5 as SEQ ID NO: 22-52. Preferably, identity is at least 75%, 80%, 85%, 90%, 95%, 97%, 98%, 99% or 100%.

Alternatively, preferably in this embodiment, a miRNA molecule or an equivalent or a mimic or an isomiR thereof has a length of not more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides, comprises at least 6 of the 7 nucleotides present in a given seed sequence as identified in Tables 5 and 7 as SEQ ID NO: 348-378, 61-115 and 379-381 and has at least 70% identity over the whole mature sequence as identified in Table 5 as SEQ ID NO: 22-52. Preferably, identity is at least 75%, 80%, 85%, 90%, 95%, 97%, 98%, 99% or 100%.

In another preferred embodiment, an isomiR of a miRNA molecule has at least 70% identity over the whole isomiR sequence (Table 7 shows preferred isomiR of each of the mature miRNAs identified as SEQ ID NO: 116-304 and 382-396. Preferably, identity is at least 75%, 80%, 85%, 90%, 95% or higher. Preferably in this embodiment, an isomiR of a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-574 molecule or equivalent or mimic or isomiR thereof comprises at least 6 of the 7 nucleotides present in the seed sequence identified as SEQ ID NO: 353, 354, 78, 79, 80, 82, 83, and/or 84 and/or has at least 70%, 75%, 80%, 85%, 90%, 95%, 97%, 98%, 99% or 100% identity over SEQ ID NO: 27, 28, 181, 182, 183, 184, 185, 186, 187, 188, 189, 190, 191, 192, 193, 194, 195, 196, 197, 198, 199, 200, 201, 202, 203, 204 and/or 205 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-7 molecule or equivalent or mimic or isomiR thereof comprises at least 6 of the 7 nucleotides present in the seed sequence identified as SEQ ID NO: 348, 349, 350, 62, 63, 64, 65, 66, 67, 68, 69, 71, 72, 73 and/or 74 and/or has at least 70%, 75%, 80%, 85%, 90%, 95%, 97%, 98%, 99% or 100% identity over SEQ ID NO: 22, 23, 24, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176 and/or 177 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-190b molecule or equivalent or mimic or isomiR thereof comprises at least 6 of the 7 nucleotides present in the seed sequence identified as SEQ ID NO: 374 and/or 96 and/or has at least 70%, 75%, 80%, 85%, 90%, 95%, 97%, 98%, 99% or 100% identity over SEQ ID NO: 48, 234, 235, 236, 237, 238, 239 and/or 240 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-142 molecule or equivalent or mimic or isomiR thereof comprises at least 6 of the 7 nucleotides present in the seed sequence identified as SEQ ID NO: 375, 376, 97, 99, 100, 101, 102, 103, 104, 105, 106, 107, 108, 109 and/or 110 and/or has at least 70%, 75%, 80%, 85%, 90%, 95%, 97%, 98%, 99% or 100% identity over SEQ ID NO: 49, 50, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288 and/or 289 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-9 molecule or equivalent or mimic or isomiR thereof comprises at least 6 of the 7 nucleotides present in the seed sequence identified as SEQ ID NO: 377, 378, 114, 115, 379, 380 and/or 381 has at least 70%, 75%, 80%, 85%, 90%, 95%, 97%, 98%, 99% or 100% identity over SEQ ID NO: 51, 52, 290, 291, 292, 293, 294, 295, 296, 297, 298, 299, 300, 301, 302, 303, 304, 382, 383, 384, 385, 386, 387, 388, 389, 390, 391, 392, 393, 394, 395 and/or 396 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a more preferred embodiment, a miRNA-9 molecule or equivalent or mimic or isomiR thereof is identified as a miRNA-9* molecule or equivalent or mimic or isomiR thereof and comprises at least 6 of the 7 nucleotides present in the seed sequence identified as SEQ ID NO: 378, 114 and/or 115 has at least 70%, 75%, 80%, 85%, 90%, 95%, 97%, 98%, 99% or 100% identity over SEQ ID NO: 52, 293, 294, 295, 296, 297, 298, 299, 300, 301, 302, 303 and/or 304 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Another preferred miRNA molecule or equivalent or mimic or an isomiR thereof has at least 60% identity with a seed sequence (as identified in Tables 5 and 7 as SEQ ID NO: 348-378, 61-115 and 379-381 or with a mature sequence (as identified in Table 5 as SEQ ID NO: 22-52 or with a precursor sequence (as identified in Table 4 as SEQ ID NO: 1-21 or with a DNA encoding an RNA precursor (as identified in Table 6 as SEQ ID NO: 53-60 or with an isomiR sequence (as identified in Table 7 as SEQ ID NO: 116-304 and 382-396. Identity may be at least 65%, 70%, 75%, 80%, 85%, 90%, 95%, 99% or 100%. Identity is preferably assessed on the whole SEQ ID NO as identified in a given table. However, identity may also be assessed on part of a given SEQ ID NO. Part may mean at least 50% of the length of the SEQ ID NO, at least 60%, at least 70%, at least 80%, at least 90% or 100%.

An equivalent of a miRNA molecule may be an isomiR or a mimic. A precursor sequence may result in more than one isomiR sequences depending on the maturation process (see for example miRNA-26b, miRNA-132, miRNA-126, or miRNA-142 wherein certain tissues multiple isomiRs have been identified (Table 7). A mimic is a molecule which has a similar or identical activity with a miRNA molecule. In this context a similar activity is given the same meaning as an acceptable level of an activity. A mimic is, in a functional determination, opposed to an antagomir. An antagomir of a miRNA molecule or equivalent or source thereof is therefore a molecule which has an activity which is opposite or reverse to the one of the corresponding miRNA molecule it derives from. An antagomir of a miRNA molecule or equivalent thereof may also be defined as a molecule which is able to antagonize or silence or decrease an activity of said miRNA molecule or equivalent thereof. An activity which is opposite or reverse to the one of the corresponding miRNA molecule it derives from or an activity which is able to antagonize an activity of said miRNA molecule it derives from is preferably an activity which is able to decrease an activity of said miRNA molecule, equivalent or source thereof. In this context, decrease means at least 5%, 10%, 20%, 30%, 40%, 50%, 60%, 70%, 80%, 90%, 95° A or 100% decrease of the activity of said miRNA molecule or equivalent or source thereof.

An antagomir of a miRNA molecule or equivalent or source thereof may be a nucleic acid, preferably a RNA which is complementary to a part of the corresponding miRNA molecule or equivalent thereof. Preferred antagomir are complementary to a part of sequences of mature miRNAs or isomiR identified in Table 5 as SEQ ID NO: 22-52 or Table 7 as SEQ ID NO: 116-304 and 382-396. A part may mean at least 50% of the length of the SEQ ID NO, at least 60%, at least 70%, at least 80%, at least 90% or 100%. In a preferred embodiment; an antagomir or an equivalent thereof is complementary to a seed sequence or a part of said seed sequence of a miRNA molecule or equivalent thereof A part may mean at least 50% of the length of the seed sequence, at least 60%, at least 70%, at least 80%, at least 90% or 100%.

Preferably, an antagomir is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and is complementary to a part of sequences of mature miRNAs or isomiR identified in Table 5 (as SEQ ID NO: 22-52) or Table 7 (as SEQ ID NO: 116-304 and 382-396). A part may mean at least 50% of the length of a given sequence, at least 60%, at least 70%, at least 80%, at least 90% or 100%.

Preferably, an antagomir is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and is complementary to a part of a seed sequence (as identified in Tables 5 and 7 as SEQ ID NO: 348-378, 61-115 and 379-381). A part may mean at least 50% of the length of the seed sequence, at least 60%, at least 70%, at least 80%, at least 90% or 100%.

Preferably an antagomir or equivalent thereof has at least 60% identity with an antagomir sequence (as identified in Table 8 as SEQ ID NO: 305-310). Identity may be at least 65%, 70%, 75%, 80%, 85%, 90%, 95%, 99% or 100%. Identity is preferably assessed on the whole SEQ ID NO as identified in Table 8. However, identity may also be assessed on a part of a given SEQ ID NO. A part may mean at least 50% of the length of the SEQ ID NO, at least 60%, at least 70%, at least 80%, at least 90% or 100%.

Preferably, an antagomir is from 8 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and has at least 60% identity with an antagomir sequence (as identified in Table 8 as SEQ ID NO: 305-310). Identity may be at least 65%, 70%, 75%, 80%, 85%, 90%, 95%, 99% or 100%. Identity is preferably assessed on the whole SEQ ID NO as identified in Table 8. However, identity may also be assessed on a part of a given SEQ ID NO. A part may mean at least 50% of the length of the SEQ ID NO, at least 60%, at least 70%, at least 80%, at least 90% or 100%.

The chemical structure of the nucleotides of an antagomir of a miRNA molecule or equivalent or source thereof may be modified to increase stability, binding affinity and/or specificity. Said antagomir may comprise or consists of a RNA molecule or preferably a modified RNA molecule. A preferred modified RNA molecule comprises a modified sugar. One example of such modification is the introduction of a 2'-O-methyl or 2'-O-methoxyethyl group or 2' fluoride group on the nucleic acid to improve nuclease resistance and binding affinity to RNA. Another example of such modification is the introduction of a methylene bridge connecting the 2'-O atom and the 4'-C atom of the nucleic acid to lock the conformation (Locked Nucleic Acid (LNA)) to improve affinity towards complementary single-stranded RNA. A third example is the introduction of a phosphorothioate group as linker between nucleic acid in the RNA-strand to improve stability against a nuclease attack. A fourth modification is conjugation of a lipophilic moiety on the 3' end of the molecule, such as cholesterol to improve stability and cellular delivery. In a preferred embodiment, an antagomir of miRNA molecule consists of a fully LNA-modified phosphorotioate oligonucleotide, termed tiny LNA as described in Obad et al. An antagomir as defined herein may comprise 1, 2, 3, 4, 5, 6, 7, 8, 9, 10 or more sugar modifications. It is also encompassed by the invention to introduce more than one distinct sugar modification in one antagomir.

Each of the miRNA molecules or equivalents or mimics or isomiRs thereof as identified herein has an acceptable level of an activity of a given miRNA they derive from. An acceptable level of an activity is preferably that said miRNA or equivalent or mimics or isomiRs thereof is still able to exhibit an acceptable level of said activity of said miRNA. An activity of a given miRNA or an equivalent thereof is for example the ability to exhibit a detectable anti-angiogenesis activity and/or induce a decrease of neo-angiogenesis as later defined herein. An acceptable level of an activity is preferably at least 30%, 40%, 50%, 60%, 70%, 80%, 90%, 95% or 100% of the activity of the miRNA they derive from.

A preferred activity of any of the miRNA molecule or equivalent or isomiR or mimic thereof as identified herein (i.e. miRNA-574, miRNA-7, miRNA-26b, miRNA-27a, miRNA-92a, miRNA-221, miRNA-222, miRNA-145, let7a1, miRNA-190b, miRNA-142, miRNA-9) is to exhibit a detectable anti-angiogenesis activity and/or induce a decrease of neo-angiogenesis in a subject as later defined herein.

A preferred activity of any of the antagomir miRNA molecule or equivalent or source thereof as identified herein (i.e. antagomir of miRNA-132, miRNA-126 and miRNA- 21) is to exhibit a detectable anti-angiogenesis activity and/or induce a decrease of neo-angiogenesis in a subject as later defined herein.

A source of a miRNA molecule or a source of an equivalent of a miRNA molecule, mimic, isomiR may be any molecule which is able to induce the production of a miRNA molecule or of an equivalent thereof such as a mimic or isomiR as identified herein and which comprises a hairpin-like structure and/or a double stranded nucleic acid molecule. The presence of a hairpin-like structure, may be assessed using the RNAshapes program (Steffen P. et al 2006) using sliding windows of 80, 100 and 120 nt or more. The hairpin-like structure is usually present in a natural or endogenous source of a miRNA molecule whereas a double-stranded nucleic acid molecule is usually present in a recombinant or synthetic source of a miRNA molecule or of an equivalent thereof.

A source of an antagomir of a miRNA molecule or a source of an equivalent of an antagomir of a miRNA molecule may be any molecule which is able to induce the production of said antagomir.

A source of a miRNA molecule or of an equivalent or a mimic or an isomiR or an antagomir thereof may be a single stranded, a double stranded RNA or a partially double stranded RNA or may comprise three strands, an example of which is described in WO2008/10558. As used herein partially double stranded refers to double stranded structures that also comprise single stranded structures at the 5' and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure.

Alternatively, a source of a miRNA molecule or of an equivalent or a mimic or an isomiR thereof is a DNA molecule encoding a precursor of a miRNA molecule or of an equivalent or a mimic or an isomiR thereof. Preferred DNA molecules in this context are identified in Table 6 as SEQ ID NO: 53-60. The invention encompasses the use of a DNA molecule encoding a precursor of a miRNA molecule that has at least 70% identity with said sequence as identified in Table 6. Preferably, the identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a DNA sequence as identified in Table 6 as SEQ ID NO: 53-60.

The induction of the production of a given miRNA molecule or of an equivalent thereof or of a mimic or an isomiR or of an antagomiR thereof is preferably obtained when said source is introduced into a cell using one assay as defined below. Cells encompassed by the present invention are later on defined.

A preferred source of a miRNA molecule or of an equivalent thereof or of a mimic or an isomiR thereof is a precursor thereof, more preferably a nucleic acid encoding said miRNA molecule or an equivalent thereof or of a mimic or an isomiR thereof A preferred precursor is a naturally-occurring precursor. A precursor may be a synthetic or recombinant precursor.

A preferred precursor of a given miRNA molecule is identified in Table 4 as SEQ ID NO: 1-21. The invention encompasses the use of a precursor of a miRNA molecule or of an equivalent thereof that has at least 70% identity with said sequence. Preferably, identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a sequence as identified in Table 4 as SEQ ID NO: 1-21.

Accordingly, a preferred source of a miRNA-574 molecule has at least 70%, 75%, 80%, 85%, 90%, 95%, 97%, 98%, 99% or 100% identity with SEQ ID NO: 5 and/or 55 and/or has a length of at least 50, 55, 60, 70, 75, 80, 85, 90, 95, 100, 130, 150, 200, 250, 300, 350, 400 nucleotides or more.

Accordingly, a preferred source of a miRNA-7 molecule has at least 70%, 75%, 80%, 85%, 90%, 95%, 97%, 98%, 99% or 100% identity with SEQ ID NO: 1, 2, 3 and/or 53 and/or has a length of at least 50, 55, 60, 70, 75, 80, 85, 90, 95, 100, 130, 150, 200, 250, 300, 350, 400 nucleotides or more.

Accordingly, a preferred source of a miRNA-190b molecule has at least 70%, 75%, 80%, 85%, 90%, 95%, 97%, 98%, 99% or 100% identity with SEQ ID NO: 17 and/or 58 and/or has a length of at least 50, 55, 60, 70, 75, 80, 85, 90, 95, 100, 130, 150, 200, 250, 300, 350, 400 nucleotides or more.

Accordingly, a preferred source of a miRNA-142 molecule has at least 70%, 75%, 80%, 85%, 90%, 95%, 97%, 98%, 99% or 100% identity with SEQ ID NO: 18 and/or 59 and/or has a length of at least 50, 55, 60, 70, 75, 80, 85, 90, 95, 100, 130, 150, 200, 250, 300, 350, 400 nucleotides or more.

Accordingly, a preferred source of a miRNA-9 molecule has at least 70%, 75%, 80%, 85%, 90%, 95%, 97%, 98%, 99% or 100% identity with SEQ ID NO: 19, 20, 21, and/or 60 and/or has a length of at least 50, 55, 60, 70, 75, 80, 85, 90, 95, 100, 130, 150, 200, 250, 300, 350, 400 nucleotides or more.

In this context, it is pointed that several precursors of a given mature miRNA molecule may lead to an identical miRNA molecule. For example, miRNA-7 may originate from precursor miRNA-7-1, mi-RNA7-2 or miRNA-7-3 (preferably identified as being SEQ ID NO: 1, 2 or 3). In a preferred embodiment, a miRNA-7-3 or a molecule having at least 70%, 75%, 80%, 85%, 90%, 95%, 97%, 98%, 99% or 100% identity with miRNA-7-3 or SEQ ID NO:3 is used as a precursor of a miRNA-7 molecule. Preferred sources or precursors have been defined later herein. A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or Lentiviral vector. Other preferred vectors are oncolytic viral vectors. Such vectors are further described herein below. Alternatively, a source may be a synthetic miRNA molecule or a chemical mimic as further defined in the part dedicated to general definitions.

The detection of the presence of a miRNA molecule or of an equivalent thereof such as a mimic or an isomiR or the presence of an antagomir of a miRNA molecule or equivalent thereof may be carried out using any technique known to the skilled person. The assessment of the expression level or of the presence of such molecule is preferably performed using classical molecular biology techniques such as (real time Polymerase Chain Reaction) qPCR, microarrays, bead arrays, RNAse protection analysis or Northern blot analysis or cloning and sequencing. The skilled person will understand that alternatively or in combination with the quantification of a miRNA molecule or of an equivalent thereof, the quantification of a substrate of a corresponding miRNA molecule or of an equivalent thereof of any compound known to be associated with a function of said miRNA molecule or of said equivalent thereof or the quantification of a function or activity of said miRNA molecule or of said equivalent thereof using a specific assay is encompassed within the scope of the invention. The same holds for an antagomir of a miRNA molecule.

Preferred compositions and formulations are all defined later herein. A miRNA molecule or an equivalent thereof or a mimic or an isomiR or an antagomir thereof may be used as such as a naked molecule, with or without chemical modifications, or encapsulated into a particle or conjugated to a moiety. A preferred composition comprises a miRNA molecule or an equivalent thereof or a mimic or an isomiR or an antagomir thereof encapsulated into a nanoparticle or a liposomal structure. A miRNA molecule or equivalent thereof or a mimic or an isomiR or an antagomir thereof may be an aptamer-miRNA hybrid. An aptamer-miRNA is defined as a miRNA linked to an RNA (or DNA) oligonucleotide, the latter adopting a conformation that targets the aptamer-miRNA hybrid molecule to a cell-surface protein (e.g. cyclic RGD peptide (cyclic arginine(R)-glycine(G)-aspartic acid(D) peptide). The aptamer-tagged miRNA can be linked to e.g. polyethylene glycol, which increases the chimera's circulating half-life (Dassie, J. P., et al. 2009).

An activity of a given miRNA or an equivalent thereof such as a mimic, isomiR or a corresponding source thereof or an activity of a given antagomir of a miRNA molecule or an equivalent thereof or a corresponding source thereof all as defined herein is preferably the ability to exhibit a detectable anti-angiogenesis activity and/or induce a decrease of neo-angiogenesis. Within the context of the invention, an anti-angiogenic activity may comprise or comprises at least one of the following:

Reduction or decrease of neo-angiogenesis,
Normalization of vessels and
Reduce number of vessels in the pathogenic area.

Exhibiting such a detectable anti-angiogenesis activity and/or inducing such a reduction or decrease of neo-angiogenesis is crucial in the present invention in order to be able to prevent, delay, cure and/or treat neo-angiogenesis and/or any disease or condition associated with neo-angiogenesis. Any disease or condition wherein neo-angiogenesis is involved or associated may be prevented, delayed, cured and/or treated with a molecule as defined herein. In a disease or condition of the invention, neo-angiogenesis may be detectable before the onset of the disease or condition i.e. before the appearance of a symptom of said disease or condition. It is further encompassed by the present invention that neo-angiogenesis is detectable during the development of said disease or condition, i.e. after the apparition of a symptom of said disease or condition. Angiogenesis is defined as the growth of new microvessels out of pre-existing capillaries. It may be distinguished from vasculogenesis, which refers to neovascularization during embryonal growth in which also larger vessels are formed and where EPCs cells participate. However, there is evidence that EPCs can play a role in tumor angiogenesis as well. It can also be distinguished from arteriogenesis which mainly involves the maturation and growth of collateral blood vessels (Asahara S. et al 1999, Carmeliet P. 2000, and Helisch A. et al 2003). Angiogenesis is the main mechanism by which new blood vessels are formed during physiological processes like wound healing, inflammation, and the female reproductive cycle. In the context of the invention, neo-angiogenesis is defined as angiogenesis when it is involved in a disease or condition which is not physiological or is pathological.

Neo-angiogenesis may be detected using any technique known to the skilled person. Neo-angiogenesis may be assessed in situ in a patient or in a tumor by non-invasive techniques such as PET (Positron emission tomography), MRI (Magnetic Resonance Imaging) (Dynamic Contrast Enhanced, DCE-MRI) or CT (Computer Tomography) imaging. These techniques may be used to monitor tumor burden, based on increased leakage of the vasculature in tumors. Using MRI or PET, you could follow the presence of angiogenesis markers such as a5β3-integrin, plasma VEGF or bFGF.

Alternatively neo-angiogenesis may be assessed using a tumor biopsy or section and subsequent immune-histochemical analyses on endothelial cells to assess their activity and compare it to the activity of normal endothelial cells from a healthy subject or from endothelial cells from the patient but isolated at a different place in the body. Such immune-histochemical analyses may be done using pan-endothelial cell antibodies such as anti-CD31 and anti-CD34 to assess microvessel density. Tissue sections could be stained with markers for endothelial cells, combined with proliferation markers, to explore the ratio between tumor endothelial cells and tumor proliferating cells in the tissue. An example of an endothelial marker is CD31 or CD34. An example of a proliferation marker is Ki67. Ki-67 is an excellent marker to determine the growth fraction of a given cell population.

The fraction of Ki-67-positive tumor cells (the Ki-67 labelling index) is often correlated with the clinical course of cancer. The microvessel density (MVD) is preferably assessed in a tumor section as in example 13 (FIG. 13) stained with an anti-CD31 and using the intensity of the staining to quantify MVD.

Quantification of MVD is preferably done by counting the positively stained luminal structures in four to five representative images per tumor section. A decrease, preferably a significant decrease of the MVD assessed in at least four to five representative images per tumor section is preferably seen as in indication that the molecule administered has an anti-angiogenesis activity or is able to induce a decrease of neo-angiogenesis.

Neo-angiogenesis may also be assessed using cells, preferably endothelial cells from a tumor, a healthy subject or endothelial cell lines. Endothelial cells from a tumor are preferably designated as tumor endothelium. Tumor endothelium may be isolated by FACS (Fluoresence Activated Cell Sorting) of tumor tissue using CD31 as an endothelial marker. This could be carried out as described in van Beijnum et al 2008. Preferred endothelial cell to assess neo-angiogenesis in vitro are HUVEC and RF24 as used in the experimental part. The assessment of neo-angiogenesis activity in vitro may be carried out using a MTS (3-(4,5-dimethylthiazol-2-yl)-5-(3-carboxymethoxyphenyl)-2-(4-sulfophenyl)-2H-tetrazolium) assay: assessment of the proliferative activity of endothelial cells. Preferably the MTS assay is carried out and results of this MTS assay are analyzed as described in the experimental part. However, other viability assays known to the skilled person may be used such as MTT (3-(4,5-Dimethylthiazol-2-yl)-2,5-diphenyltetrazolium bromide), Crystal Violet and WST-1 (Water Soluble Tetrazolium).

In addition, other types of assays could be used such as spheroid sprouting assay and matrigel tube formation assay as second line activity assays. In the matrigel tube formation assay, cells, especially endothelial cells, are seeded on a synthetic semi-natural gel matrix (such as Matrigel from BD Biosciencesor collagen-gel, in some cases fibrin gels). In both assays, endothelial cells, preferably HUVECs are being used. After a certain period of time, depending on cell culture conditions, cells begin to form tube-like structures. The formation of tube-like structures is regarded as a first step towards the generation of new vessels. The read-out parameter is the number of vessel-knots per area unit. For the spheroid sprouting assay, cell spheroids (e.g. endothelial cells) are placed on a gel (e.g. matrigel and collagen gels). After a certain period of time sprout formation can be observed. The extend of sprouting is considered as a criteria for the evaluation of the angiogenic potential of cells. The read-out parameter is the number of sprouts per spheroid. An anti-angiogenic activity may be present when the number of vesselknot per area unit, respectively number of sprouts per spheroid is reduced or decreased for a given period of time by comparison to the corresponding number of vesselknot per area unit, respectively number of sprouts per spheroid in untreated cells versus the number of sprouts per spheroid in treated cells. A decrease or a reduction may be a decrease of 5%, 10%, 20%, 30%, 40%, 50%, 60%, 70%, 80%, 90% or 100%. Preferably, no vesselknot per area unit, respectively no sprout per sheroid is detectable in a given period of time.

An anti-angiogenic activity in a tumor tissue may also be present when a normalization of vessels is visualized and/or when the number of vessels in the pathogenic area is reduced.

In a preferred embodiment, as soon as the number of vessel in the pathogenic area is found to be decreased by comparison to the number of vessel at the onset of the treatment, there is a detectable anti-angiogenic activity. A decrease may be a detectable decrease of the number of vessels in the pathogenic area or a decrease of 5%, 10%, 20%, 30%, 40%, 50%, 60%, 70%, 80% of the vessel in the pathogenic area. Pathogenic area is the area of the tumor including the surrounding tissue, located close to the tumor area. Close in this context may mean up to a few centimeters.

A normalization of vessels is preferably a change in the 3 dimensional structure of a vessel or microvessel. For example, a pathological vessel or microvessel associated with neo-angiogenesis activity in a tumor endothelium may be less regular and/or appears more tortuous and/or appears more leaky than a control vessel or microvessel. A control vessel may be a vessel from a healthy individual or a vessel from the patient but not located in the pathogenic area from said patient. In a preferred embodiment, as soon as the 3 dimensional structure of a vessel appears more regular, less tortuous and/or less leaky than a control vessel, an anti-angiogenic activity is said to have been detected. Preferably, less irregular, tortuous and/or leaky vessels are detected in the pathogenic area than at the onset of the treatment. More preferably, less means 5% less, 10%, 20%, 30%, 40%, 50%, 60%, 70%, 80%, 90% or 100% less. Most preferably, no irregular, tortuous and/or leaky vessels are detected in the pathogenic area. A normalization of vessels and/or the number of vessels in the pathogenic area may be assessed using a non-invasive imaging technique such as PET, MRI or CT imaging.

In the case of an eye disease or condition associated with neo-angiogenesis, several assays have been developed for assessing a detectable anti-angiogenesis activity and/or a reduction or decrease of neo-angiogenesis induced by a drug to be tested. In these different disease models, the angiogenesis can be triggered by different stimuli such a mechanical stimulus (laser induced rupture of Bruch's membrane) (Shen et al, 2006 Gene therapy. 13, 225-234) or by the overexpression of specific blood vessel growth such as vEGF in transgenic mice (Miki et al, 2009, Ophthalmology. 2009 September 116(9): 1748-1754). If a detectable anti-angiogenesis activity and/or a reduction or decrease of angiogenesis is assessed using a miRNA molecule, equivalent or source thereof as identified herein, such miRNA molecule, equivalent or source thereof is said to be used as a medicament for preventing, treating, reverting, curing and/or delaying neo-angiogenesis or a disease or a condition associated with neo-angiogenesis.

The assessment of neo-angiogenesis and/or anti-angiogenic activity may be carried out periodically, e.g. each week, each month. The increase/decrease of neo-angiogenesis and/or presence of an anti-angiogenic activity may therefore be assessed periodically, e.g. each week, month. This assessment is preferably carried out at several time points for a given subject or at one or several time points for a given subject and a healthy control. The assessment may be carried out at regular time intervals, e.g. each week, each month. The assessment may therefore be assessed regularly, e.g. each week, each month. When one assessment of neo-angiogenesis or angiogenic activity has led to the finding of a decrease of neo-angiogenesis or to the presence of an anti-angiogenic activity, a miRNA molecule, an equivalent, a mimic, an isomiR thereof a or a source thereof or an antagomiR or an equivalent or a source thereof is said is exhibit a detectable anti-angiogenesis activity and/or inducing a reduction or decrease of neo-angiogenesis.

A detectable decrease of neo-angiogenesis activity and/or the presence of an anti-angiogenic activity has been preferably detected when for at least one time point, a decrease of neo-angiogenesis and/or the presence of an anti-angiogenic activity has been detected. Preferably, a decrease of neo-angiogenesis and/or the presence of an anti-angiogenic activity has been detected for at least two, three, four, five time points.

The invention provides a miRNA-9, miRNA-574, miRNA-7, miRNA-190b and/or miRNA-142 molecule, an equivalent or a source thereof or a composition comprising said miRNA-9, miRNA-574, miRNA-7, miRNA-190b and/or miRNA-142 molecule said equivalent or said source thereof, preferably, for use as a medicament for preventing, treating, reverting, curing and/or delaying neo-angiogenesis or a disease or a condition associated with neo-angiogenesis.

It has been surprisingly found that a miRNA-190b molecule or equivalent or mimic or isomiR thereof is able to exhibit a detectable anti-angiogenesis activity and/or to induce a decrease of neo-angiogenesis as demonstrated in example 7 and example 8.

It has been surprisingly found that a miRNA-142 molecule or equivalent or mimic or isomiR thereof is able to exhibit a detectable anti-angiogenesis activity and/or to induce a decrease of neo-angiogenesis as demonstrated in example 7 and example 8.

It has been surprisingly found that a miRNA-9* molecule or equivalent or mimic or isomiR thereof is able to exhibit a detectable anti-angiogenesis activity and/or to induce a decrease of neo-angiogenesis as demonstrated in example 9, example 10 and example 12.

It has been surprisingly found that a miRNA-7 molecule or equivalent or mimic or isomiR thereof is able to exhibit a detectable anti-angiogenesis activity and/or to induce a decrease of neo-angiogenesis as demonstrated in example 7, example 11 and example 12.

It has been surprisingly found that a miRNA-574 molecule or equivalent or mimic or isomiR thereof is able to exhibit a detectable anti-angiogenesis activity and/or to induce a decrease of neo-angiogenesis as demonstrated in example 7, example 11 and example 12.

Preferably, a miRNA-9, miRNA-574, miRNA-7, miRNA-190b and/or miRNA-142 molecule or an equivalent or a source thereof is able to prevent, treat, revert, cure and/or delay neo-angiogenesis or a disease or a condition associated with neo-angiogenesis when said molecule exhibits a detectable anti-angiogenesis activity or induces a decrease of neo-angiogenesis. Throughout the invention, a molecule exhibiting a detectable anti-angiogenesis activity is synonymous with a molecule that induces a decrease of neo-angiogenesis. Preferably, a decrease of neo-angiogenesis means a significant decrease, preferably a decrease of at least 5% of neo-angiogenesis. The decrease of neo-angiogenesis may be assessed using any of the assays mentioned earlier herein. The presence of a neo-angiogenesis activity in a subject may be assessed in endothelial cells from a tumor, a healthy subject. Endothelial cells from a tumor may also be designated as the tumor endothelium. The assessment of the activity may be carried out immune-histochemical analyses using pan-endothelial cell antibodies such as anti-CD31 and anti-CD34 to assess microvessel density as earlier defined herein. Such decrease of neo-angiogenesis activity may be measured by comparing said neo-angiogenesis activity in an endothelial cell from a subject at a given time point after start of treatment with the corresponding activity from an endothelial cell from the same subject before the onset of the treatment.

More preferably, a decrease means a decrease of at least 10%, even more preferably at least 20%, at least 30%, at least 40%, at least 50%, at least 70%, at least 90%, or 100%. In this case, no neo-angiogenesis activity is detectable.

Neo-angiogenesis or a disease or condition wherein neo-angiogenesis is involved or associated is any disease or condition wherein an abnormal or excessive or unwanted neo-vascularization occurs. For example abnormal or excessive neo-angiogenesis occurs in various eye diseases, where it may result in hemorrhage and functional disorders of the eye, contributing to the loss of vision associated with retinopathy of prematurity, diabetic retinopathy, retinal vein occlusion, age-related macular degeneration, and other eye diseases (see, for example, Yoshida et al., 1999, Histol Histopathol. 14(4): 1287-94). These conditions are leading causes of blindness (Aiello, 1997, Ophthalmic Res. 29(5): 354-62). Excessive angiogenesis also plays a role in other disease conditions such as rheumatoid arthritis, and psoriasis.

Furthermore, neo-angiogenesis plays an important role in the growth and metastasis of tumors. Indeed several angiogenesis inhibitors are used clinically in the treatment of cancer. Therefore, a condition or disease wherein neo-angiogenesis is involved or associated may be a cancer.

In a preferred embodiment, a disease or condition wherein neo-angiogenesis is involved or associated is a cancer (e.g., malignant, metastatic), an eye disease as a disorder including age-related macular degeneration, a diabetic retinopathy, a retinal vein occlusion, or rheumatoid arthritis, psoriasis, endometriosis or any other disease or condition wherein inflammation is present (Carmeliet P. et al 2005 and Griffioen A. W. et al, 2000). Cancers of a preferred embodiment of the invention include a cancer of epithelial origin or neuronal origin or a carcinoma or a solid tumor or a sarcoma or a liquid tumor such a leukemia or a lymphoma. Cancer cells may be from the bladder; brain; breast; colon; esophagus; gastrointestine; head; kidney; liver; lung; nasopharynx; neck; ovary; prostate; skin; stomach; testis; tongue; neuron or uterus. In addition, the cancer may specifically be of the following histological type, though it is not limited to these: neoplasm; malignant; carcinoma; carcinoma undifferentiated; giant and spindle cell carcinoma; small cell carcinoma; pilomatrix carcinoma; transitional cell carcinoma; papillary transitional cell carcinoma; adenocarcinoma; gastrinoma; malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma; familial polyposis coli; solid carcinoma; carcinoid tumor; malignant; branchiolo-alveolar carcinoma; papillary carcinoma; squamous cell carcinoma; basal adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease of the breast; acinar cell carcinoma; adenosquamous carcinoma; adenocarcinoma w/squamous metaplasia; ovarian stromal tumor, malignant; and roblastoma, malignant; Sertoli cell carcinoma. A cancer may be neuroblastoma.

In this context a leukemia includes any of: Acute lymphoblastic leukemia (ALL) such as precursor B acute lymphoblastic leukemia, precursor T acute lymphoblastic leukemia, Burkitt's leukemia, and acute biphenotypic leukemia, Chronic lymphocytic leukemia (CLL) such as B-cell prolymphocytic leukemia, a more aggressive disease, Acute myelogenous leukemia (AML) such as acute promyelocytic leukemia, acute myeloblastic leukemia, and acute megakaryoblastic leukemia, Chronic myelogenous leukemia (CML) such as chronic monocytic leukemia, Hairy cell leukemia (HCL), T-cell prolymphocytic leukemia (T-PLL), Large granular lymphocytic leukemia and Adult T-cell leukemia.

In this context a Lymphoma includes any of: Small lymphocytic lymphoma, Lymphoplasmacytic lymphoma (such as Waldenström macroglobulinemia), Splenic marginal zone lymphoma, Plasma cell myeloma, Plasmacytoma, Extranodal marginal zone B cell lymphoma (MALT lymphoma), Nodal marginal zone B cell lymphoma (NMZL), Follicular lymphoma, Mantle cell lymphoma Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma—nasal type, Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma, unspecified Anaplastic large cell lymphoma, Hodgkin lymphoma, Immunodeficiency-associated lymphoproliferative disorders.

Any cancer that is already known to be treated with an angiostatic compound is encompassed within the scope of the invention. Preferred cancers in this context are: carcinoma, sarcomas, leukemias and lymphomas. More preferred cancers in this context are: colon, breast, lung carcinoma's and renal carcinoma's and glioma's. There are currently known medicaments (angiostatic compounds) that may be used for specifically preventing, treating, reverting, curing and/or delaying neo-angiogenesis or a disease or condition associated with neo-angiogenesis in a subject. However, each of these treatments is likely to display a therapeutic activity which is not sufficient to be used in patients and/or induce resistance. Such a therapeutic activity is not sufficient to be used in patients preferably when such known medicaments (angiostatic compounds) are not able to exhibit a detectable anti-angiogenesis activity and/or not able to induce a decrease of neoangiogenesis. Each of these features has been defined earlier herein. The invention provides a new medicament which is expected not to have such drawbacks. The invention encompasses to use a miRNA-9, miRNA-574, miRNA-7, miRNA-190b and/or miRNA-142 molecule, an equivalent or a source thereof or a composition comprising said miRNA-9, miRNA-574, miRNA-7, miRNA-190b and/or miRNA-142 molecule or equivalent thereof or a source thereof. This use includes increasing, preferably pharmacologically increasing an activity or the steady-state level of said miRNA-9, miRNA-574, miRNA-7, miRNA-190b and/or miRNA-142 or equivalent thereof or of said source thereof in a subject, in a cell of said subject, in a tissue of said subject or in body fluid of said subject.

Within the context of the invention, "increasing an activity or the steady-state level of an antagomir or equivalent thereof or of said source thereof" could be replaced by "decreasing an activity or the steady-state level of a miRNA molecule or equivalent thereof". The same holds for other antagomir identified herein.

In this use, an activity or steady-state level of said miRNA-9, miRNA-574, miRNA-7, miRNA-190b and/or miRNA-142 or equivalent thereof or source thereof is increased in order to exhibit a detectable anti-angiogenesis activity and/or induce a detectable decrease of neo-angiogenesis. The assessment of an anti-angiogenesis activity and of neo-angiogenesis in a subject had been earlier defined herein.

An activity or steady-state level of said miRNA-9, miRNA-574, miRNA-7, miRNA-190b and/or miRNA-142 molecule, equivalent thereof such as a mimic or isomiR thereof or source thereof may be increased at the level of said miRNA molecule (or equivalent thereof) itself, e.g. by providing said miRNA molecule or equivalent thereof to a subject, preferably to a cell of a subject, or to a tissue of said subject, or to an organ of said subject or to said subject said miRNA molecule or equivalent thereof being from an exogenous source. For provision of a miRNA molecule or equivalent thereof from an exogenous source, said miRNA molecule or equivalent thereof may conveniently be produced by expression of a nucleic acid encoding said miRNA molecule or equivalent thereof or encoding a source of said miRNA molecule or equivalent thereof in a suitable host cell as described below or as completely synthetic molecule by chemical synthesis.

Preferably, however, an activity or steady-state level of a miRNA molecule or equivalent thereof is increased by regulating the expression level of a nucleotide sequence encoding said miRNA molecule or equivalent thereof or encoding a source of said miRNA molecule or equivalent thereof. Preferably, the expression level of a nucleotide sequence is regulated in a cell of said subject or in a tissue of said subject or in the subject. The expression level of a miRNA molecule or equivalent thereof or a source of said miRNA molecule or equivalent thereof may be increased by introduction of a miRNA, and equivalent, or a source thereof, or an expression construct (or vector) into a cell, tissue, organ or body fluid of said subject, or in the subject whereby an expression vector comprises a nucleotide sequence comprising a miRNA molecule or equivalent thereof or comprising a source of said miRNA molecule or equivalent thereof, and whereby a nucleotide sequence is under control of a promoter capable of driving expression of a nucleotide sequence in said cell, tissue, organ, subject. The expression level of a miRNA molecule or equivalent thereof or source thereof may also be increased by introduction of an expression construct into a cell, tissue, organ, subject, whereby a construct comprises a nucleotide sequence encoding a factor capable of trans-activation of an endogenous nucleotide sequence encoding a miRNA molecule or equivalent thereof.

A use of the invention preferably comprises the step of administering to a subject a therapeutically effective amount of a pharmaceutical composition comprising a nucleic acid construct for increasing the activity or steady state level of miRNA-9, miRNA-574, miRNA-7, miRNA-190b and/or miRNA-142 molecule or equivalent as defined herein. A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or Lentiviral vector. Alternatively, a use of the invention preferably comprises the step of administering to a subject a therapeutically effective amount of a pharmaceutical composition comprising a miRNA-9 molecule, an equivalent or a source thereof as defined herein.

In a use of the invention, a cell, a tissue, an organ or body fluid is preferably from a subject suspected to have a high risk of exhibiting neo-angiogenesis or of having a disease or condition associated with neo-angiogenesis due for example to its age or its genetic background or to its diet. Alternatively, in another preferred embodiment, use of the invention is applied on a cell, tissue, organ or body fluid from a subject diagnosed as either having a predictive risk for developing later a disease or condition associated with neo-angiogenesis. A diagnostic method used is preferably one of the inventions as described herein. Alternatively, a cell, a tissue or organ to be treated may be selected based on risk of progression of the disease or condition associated with neo-angiogenesis. Such risk of progression may be assessed using classical clinic-pathological criteria or biomarker-based prognosis known to the skilled person. It is also encompassed by the invention to administer a miRNA-9, miRNA-574, miRNA-7, miRNA-190b and/or miRNA-142 molecule or equivalent thereof or a precursor thereof or a composition comprising said miRNA-9, miRNA-574, miRNA-7, miRNA-190b and/or miRNA-142 molecule or equivalent thereof or source thereof into a tissue or organ of said subject. The organ or tissue may correspond to the organ or tissue wherein neo-angiogenesis or a disease or condition associated with neo-angiogenesis had been diagnosed. In the invention, a preferred tissue is a tissue comprising or containing or consisting of a tumor endothelium. In the invention, a preferred organ is colon, breast, lung, kidney or brain in case of a colon, breast, lung or a renal carcinoma or glioma, or any tumor endothelium derived from said organ mentioned above. A tumor endothelium is a tissue comprising or consisting of endothelial cells that are associated with tumor cells, either located within the boundaries of the tumor tissue or in the vicinity thereof, and that are activated by the action of tumor derived molecular signals such as growth factors, cytokines and/or hormones. A vicinity of a tumor in this context may mean up to a few centimeters. Within a tumor usually 0.1-5% of cells are of endothelial origin. Some tumors, such as endothelioma, haemangioma and Kaposi sarcoma, are originating from endothelial cells, through which the number of endothelial cells can be as high as 99%.

A tumor endothelium is a tissue comprising 30%, 40%, 50%, 60%, 70%, 80%, 90%, 100% endothelial cells, preferably these cells are activated as defined earlier herein and wherein said cells are associated with tumor cells, either located within the boundaries of the tumor tissue or in the vicinity thereof. The assessment of the identity of endothelial cell is preferably carried out using FACS staining cells with endothelial markers as CD31 and CD34 on a tumor tissue obtained from a biopsy. The assessment of the activation of endothelial cell is preferably carried out using FACS staining cells with a marker as Ki-67 on a tumor tissue obtained from a biopsy. Preferred tissues comprise colon, breast, lung or kidney in case of a colon, breast, lung carcinoma or a renal carcinoma or glioma. In the invention, a preferred cell is a cell derived from a colon, breast, lung or kidney in case of a colon, breast, lung carcinoma or a renal carcinoma or glioma. This cell may be or comprise a tumor cell or an endothelial cell. In each case, a miRNA-9, miRNA-574, miRNA-7, miRNA-190b and/or miRNA-142 molecule or equivalent or source thereof is preferably administered to an endothelial cell present in said organ, tissue. Said miRNA-9, miRNA-574, miRNA-7, miRNA-190b and/or miRNA-142 molecule or equivalent or source thereof is preferably administered to a tissue comprising 30%, 40%, 50%, 60%, 70%, 80%, 90%, 100% endothelial cells. Said miRNA-9, miRNA-574, miRNA-7, miRNA-190b and/or miRNA-142 molecule or equivalent or source thereof may be targeted to endothelial cells. A treatment of a disease or condition associated with neo-angiogenesis may include a treatment that prevents neo-angiogenesis in a tumor tissue that contains tumor cell that has not yet metastasized or decreases neo-angiogenesis around tumor cell that has already formed metastases and/or is migrating from the primary tumor to distant sites in the body. Alternatively or in combination with preferred definition, a treatment of a disease or condition associated with neo-angiogenesis may include a treatment that prevents neo-angiogenesis in a tumor tissue that contains endothelial cells. In this preferred embodiment, endothelial cells are specifically targeted by linking or conjugating said miRNA-9, miRNA-574, miRNA-7, miRNA-190b and/or miRNA-142 or equivalent or source thereof to a targeting part. A preferred targeting part is a cRGD as identified herein or any molecule known to recognize or bind a molecule which is expressed on endothelial cells. A preferred molecule expressed on endothelial cells is CD31 and CD34.

In another use, the invention mentioned herein may be combined with standard treatments of disease or condition associated with neo-angiogenesis such as chemotherapy, radiotherapy or surgery. Examples of chemotherapeutic agents are later identified herein.

Although gene therapy is a possibility for preventing, treating, reverting and/or delaying neo-angiogenesis or a condition or a disease associated with neo-angiogenesis, other possible treatments may also be envisaged. For example, treatment by "small molecule" drugs to steer certain molecular pathways in the desired direction, is also preferred. These small molecules are preferably identified by the screening method of the invention as defined later herein.

In the context of the invention, preventing, treating, reverting, curing and/or delaying a disease or condition associated with neo-angiogenesis may mean that:
The severity of at least one symptom of this disease or condition has been reduced, and/or
At least a parameter associated with this disease or condition has been improved: preferably such parameter is associated with neo-angiogenesis and/or an angiogenic activity.

A symptom may be endothelial sprouts. The presence of endothelial sprouts may be assessed in situ in a patient or in a tumor by non-invasive techniques such as PET, MRI (Dynamic Contrast Enhanced, DCE-MRI) or CT imaging as for assessing neo-angiogenesis. The severity of the symptom endothelial sprouts is preferably said to have been reduced when the number of endothelial sprouts originating from a tumor is decreased of at least 1%, 5%, 10%, 15%, 20%, 30%, 40%, 50%, 55%, 60%, 65%, 70% or 75%, or more. Endothelial sprouts may be assessed or detected after at least one week, two weeks, three weeks, fours weeks, one month, two months, three months, four months, five months, six months or more of treatment in a subject and compared to the number of endothelial sprouts at the onset of the treatment.

A parameter may be the assessment of neo-angiogenesis and/or anti-angiogenic activity as explained earlier herein. In the context of the invention, preventing, treating, reverting, curing and/or delaying neo-angiogenesis or a disease or condition associated with neo-angiogenesis may be replaced by achieving an anti-tumor effect. Unless otherwise indicated, an anti-tumor effect is preferably assessed or detected after at least one week, two weeks, three weeks, fours weeks, one month, two months, three months, four months, five months, six months or more in a treated subject. An anti-tumor effect is preferably identified in a subject as:
an inhibition of proliferation of tumor cells and/or
an induction or increased induction of tumor cells death and/or
a delay in occurrence of metastases and/or of tumor cell migration and/or
an inhibition or prevention or delay of the increase of a tumor weight or growth and/or
a prolongation of patient survival of at least one month, several months or more (compared to those not treated or treated with a control or compared with the subject at the onset of the treatment) and/or
improvement of the quality of life and observed pain relief In the context of the invention, a patient may survive and/or may be considered as being disease free. Alternatively, the disease or condition may have been stopped or delayed. In the context of the invention, an improvement of quality of life and observed pain relief may mean that a patient may need less pain relief drugs than at the onset of the treatment. Alternatively or in combination with the consumption of less pain relief drugs, a patient may be less constipated than at the ontset of the treatment. "Less" in this context may mean 5% less, 10% less, 20% less, 30% less, 40% less, 50% less, 60% less, 70% less, 80% less, 90% less. A patient may no longer need any pain relief drug. This improvement of quality of life and observed pain relief may be seen, detected or assessed after at least one week, two weeks, three weeks, fours weeks, one month, two months, three months, four months, five months, six months or more of treatment in a patient and compared to the quality of life and observed pain relief at the onset of the treatment of said patient.

An inhibition of the proliferation of tumor cells, preferably endothelial cells from the tumor endothelium may be at least 20%, 30%, 40%, 50%, 55%, 60%, 65%, 70% or 75%, or more. Proliferation of cells may be assessed using known techniques. An induction of tumor cell death may be at least 1%, 5%, 10%, 15%, 20%, 25%, or more. Tumor growth may be inhibited at least 5%, 10%, 20%, 30%, 40%, 50%, 55%, 60%, 65%, 70% or 75%, or more. Tumor cell death may be assessed using techniques known to the skilled person. Tumor cell death may be assessed using MRI or CT. In certain embodiments, tumor weight increase or tumor growth may be inhibited at least 20%, 30%, 40%, 50%, 55%, 60%, 65%, 70% or 75%, or more. Tumor weight or tumor growth may be assessed using techniques known to the skilled person.

The detection of tumor growth or the detection of the proliferation of tumor cells may be assessed in vivo by measuring changes in glucose utilization by positron emission tomography with the glucose analogue 2-[18F]-fluor-2-deoxy-D-glucose (FDG-PET) or [18F]-'3-fluoro-'3-deoxy-L-thymidine PET. An ex vivo alternative may be staining of a tumor biopsy with Ki67.

To test the effect of a miRNA molecule on tumour growth in an animal model in vivo, an experimental system as described in example 12 may be used. A delay in occurrence of metastases and/or of tumor cell migration may be a delay of at least one week, one month, several months, one year or longer. The presence of metastases may be assessed using MRI, CT or Echography or techniques allowing the detection of circulating tumour cells (CTC). Examples of the latter tests are CellSearch CTC test (Veridex), an EpCam-based magnetic sorting of CTCs from peripheral blood. In certain embodiments, tumor growth may be delayed at least one week, one month, two months or more. In a certain embodiment, an occurrence of metastases is delayed at least one week, two weeks, three weeks, fours weeks, one months, two months, three months, four months, five months, six months or more.

In a further preferred embodiment, there is provided a composition further comprising another miRNA molecule and/or an antagomir of a miRNA molecule selected from:

a) a miRNA-9, a miRNA-190b, miRNA-7, a miRNA-574 and/or a miRNA-142 molecule, an equivalent such as a mimic and/or an isomiR and/or a source thereof, b) optionally at least one of miRNA-26b, miRNA-27a, miRNA-92a, miRNA-221, miRNA-222, miRNA-145 and a let7a1 molecule an equivalent such as a mimic or an isomiR or a source thereof, c) and optionally at least one antagomir of a miRNA-132, miRNA-126 and miRNA-21 or an equivalent or a source thereof.

Since not each of the identified miRNAs molecules or equivalents thereof is expected to have the same target genes, it is assumed that the use of a miRNA-9, miRNA-574, miRNA-7, miRNA-190b and/or miRNA-142 molecule or equivalent thereof or source thereof optionally combined with at least one of the miRNAs molecule, or equivalent thereof or source thereof identified above under a) and/or b) and/or at least one antagomir or equivalent or source thereof as identified above under c) allows a more effective treatment of a disease or condition associated with neo-angiogenesis. A tumor treated by a composition or a cocktail of at least a miRNA-9, miRNA-574, miRNA-7, miRNA-190b and/or miRNA-142 molecule, or equivalent or source thereof is expected to have fewer possibilities to escape or to resist said treatment. In a further preferred embodiment, it is encompassed to diagnose the expression of each of the miRNA molecules or of their target genes as identified herein and depending on the outcome to adapt the identity of the miRNA molecules used for the treatment.

When the invention relates to a composition comprising more than one miRNA molecule or equivalent thereof or source thereof or antagomir thereof it is encompassed that each miRNA molecule or equivalent thereof or source thereof or antagomir thereof may be present each in a separate composition, each composition being sequentially or simultaneously administered to a subject. Alternatively, it is also encompassed that more than one miRNA molecules or equivalents thereof or sources thereof or antagomir thereof is present in a composition as defined herein.

Therefore the invention further encompasses to use a miRNA molecule, an equivalent or a source thereof or a composition comprising said miRNA molecule or equivalent thereof or a source thereof as identified under a) and/or b) and/or an additional antagomir of a miRNA molecule or an equivalent therefore as identified under c). This preferred use:

includes increasing, preferably pharmacologically increasing an activity or the steady-state level of said miRNA molecule or equivalent thereof or of said source thereof as identified under a) and/or b) in a subject, in a cell of said subject, in a tissue of said subject or in body fluid of said subject and/or includes decreasing, preferably pharmacologically decreasing an activity or the steady-state level of said miRNA molecule or equivalent thereof or of said source thereof as identified under c) in a subject, in a cell of said subject, in a tissue of said subject or in body fluid of said subject.

In this preferred use:

an activity or steady-state level of a miRNA molecule as defined under a) and/or b) may be increased in order to exhibit a detectable anti-angiogenesis activity and/or induce a detectable decrease of neo-angiogenesis and/or an activity or steady-state level of an antagomir as defined under c) may be increased in order to exhibit a detectable anti-angiogenesis activity and/or induce a detectable decrease of neo-angiogenesis.

Ways of increasing an activity or steady state level of an antagomir have already been defined earlier herein. The assessment of an anti-angiogenesis activity and of neo-angiogenesis in a subject had been earlier defined herein.

In a further aspect, there is provided the use of a miRNA-9, miRNA-574, miRNA-7, miRNA-190b and/or miRNA-142 molecule, an equivalent or a source thereof or a composition comprising said miRNA-9, miRNA-574, miRNA-7, miRNA-190b and/or miRNA-142 an equivalent or a source thereof preferably for the manufacture of a medicament for preventing, treating, reverting, curing and/or delaying neo-angiogenesis or a disease or a condition associated with neo-angiogenesis. Each feature of this further aspect has already been described herein.

In a further aspect, there is provided a method for preventing, treating, reverting, curing and/or delaying neo-angiogenesis or a condition or disease associated with neo-angiogenesis by administering a miRNA molecule or equivalent thereof or source thereof or an antagomir thereof or a composition as earlier defined herein to a subject in the need thereof. Each feature of this further aspect has already been described herein.

In a further aspect, there is provided a method for diagnosing neo-angiogenesis or a disease or condition associated with neo-angiogenesis in a subject, the method comprising the steps of:
(a) determining the expression level of a miRNA-9, miRNA-574, miRNA-7, miRNA-190b and/or miRNA-142 molecule, an equivalent or a source thereof in a subject, and optionally
(b) comparing the expression level of said molecule or equivalent thereof or source thereof as defined in (a) with a reference value for the expression level of said molecule, equivalent or source thereof, the reference value preferably being the average value for the expression level of said molecule, equivalent or source thereof in a healthy subject.

In the context of the invention, diagnosis means either a predictive risk assessment of a subject for developing neo-angiogenesis or for developing a disease or a condition associated with neo-angiogenesis. In the context of the invention, a subject may be an animal or a human being. Preferably, a subject is a human being. In the context of the invention, the reference value assessed in (b) and the expression level of a miRNA-9, miRNA-574, miRNA-7, miRNA-190b and/or miRNA-142 molecule, an equivalent or a source thereof assessed in (a) are assessed in a corresponding or similar tissue of both subjects.

Since the expression levels of these nucleotide sequences and/or amounts of corresponding miRNA molecule or equivalent thereof or source thereof may be difficult to be measured in a subject, a sample from a subject is preferably used. According to another preferred embodiment, the expression level (of a nucleotide sequence or miRNA molecule or equivalent or source thereof) is determined ex vivo in a sample obtained from a subject. The sample preferably comprises a body fluid of a subject. A sample may be a tissue biopsy or a tumor biopsy or a cancer tissue of epithelial origin of a subject. A preferred tissue is either primary tumor tissue or metastasized tissue. A body fluid may comprise or be derived from blood, serum, sputum, plasma, CSF (Cerebrospinal Fluid), stool, urine. It is specifically contemplated that the invention can be used to evaluate or diagnose differences between stages of disease or condition associated with neo-angiogenesis, such as between pre-cancer and cancer, or between a primary tumor and a metastasized tumor.

An increase or decrease of the expression level of a nucleotide sequence (or steady state level of the encoded miRNA molecule or equivalent or source thereof) is preferably defined as being a detectable change of the expression level of a nucleotide (or steady state level of an encoded miRNA molecule or equivalent or source thereof or any detectable change in a biological activity of a miRNA molecule or equivalent or source thereof) using a method as defined earlier on as compared to the expression level of a corresponding nucleotide sequence (or steady state level of a corresponding encoded miRNA molecule or equivalent or source thereof) in a healthy subject. A preferred nucleotide sequence is a sequence encoding a precursor of a miRNA molecule or equivalent thereof. According to a preferred embodiment, an increase or decrease of a miRNA activity is quantified using a specific assay for a miRNA activity. A preferred assay is the assessment of neo-angiogenesis as earlier defined herein.

Preferably, a decrease of the expression level of a nucleotide sequence means a decrease of at least 10% of the expression level of the nucleotide sequence using arrays. More preferably, a decrease of the expression level of a nucleotide sequence means an decrease of at least 15%, even more preferably at least 20%, at least 30%, at least 40%, at least 50%, at least 70%, at least 90%, or 100%. In this case, there is no detectable expression.

Preferably, a decrease of the expression level of a miRNA molecule or equivalent or source thereof means a decrease of at least 10% of the expression level of the miRNA using qPCR, microarrays or Northern blot analysis. Preferably qPCR is stem-loop RT qPCR. More preferably, a decrease of the expression level of a miRNA molecule or equivalent or source thereof means a decrease of at least 15%, even more preferably at least 20%, at least 30%, at least 40%, at least 50%, at least 70%, at least 90%, or 100%. In this case, there is no detectable expression.

Preferably, a decrease of a miRNA activity means a decrease of at least 5% of a miRNA activity using a suitable assay. More preferably, a decrease of a miRNA activity means a decrease of at least 10%, even more preferably at least 20%, at least 30%, at least 40%, at least 50%, at least 70%, at least 90%, or 100%. In this case, there is no detectable activity.

Preferably, an increase of the expression level of a nucleotide sequence means an increase of at least 10% of the expression level of the nucleotide sequence using any of the techniques mentioned herein. More preferably, an increase of the expression level of a nucleotide sequence means an increase of at least 15%, even more preferably at least 20%, at least 30%, at least 40%, at least 50%, at least 70%, at least 90%, at least 150% or more.

Preferably, an increase of the expression level of a miRNA molecule or equivalent or source thereof means an increase of at least 10% of the expression level of the miRNA molecule or equivalent or source thereof using RT-qPCR, preferably stem-loop RT qPCR. More preferably, an increase of the expression level of a miRNA molecule or equivalent or source thereof means an increase of at least 15%, even more preferably at least 20%, at least 30%, at least 40%, at least 50%, at least 70%, at least 90%, at least 150% or more.

Preferably, an increase of a miRNA activity means an increase of at least 5% of a miRNA activity using a suitable assay. More preferably, an increase of a miRNA activity means an increase of at least 10%, even more preferably at least 20%, at least 30%, at least 40%, at least 50%, at least 70%, at least 90%, at least 150% or more.

Preferably, an expression level is determined ex vivo in a sample obtained from a subject. More preferably, the sample is as earlier defined herein and wherein subsequently, a given nucleotide sequence and/or miRNA molecule or equivalent or source thereof is extracted and purified using known methods to the skilled person. More preferably, the sample is or comprises or is derived from a tumor biopsy, blood, sputum, stool or urine.

In a diagnostic method of the invention preferably the expression level of more than one, more preferably of at least 1, 2, 3, 4, 5, 6, 7, 8, 9, 10, 11, 12, 13, 14, 15 miRNAs molecule or equivalent or source thereof and/or the steady state levels of the corresponding miRNAs molecule or equivalent or source thereof are determined Accordingly in a preferred method, in step (a) one determines the expression level of another miRNA molecule or equivalent or source thereof selected from:
 a) a miRNA-9, a miRNA-190b, miRNA-7, a miRNA-574 and/or a miRNA-142 molecule, an equivalent and/or a source thereof,
 b) optionally at least one of miRNA-26b, miRNA-27a, miRNA-92a, miRNA-221, miRNA-222, miRNA-145, let7a1, miRNA-132, miRNA-126 and miRNA-21 molecule an equivalent or a source thereof.

In a further preferred method, neo-angiogenesis or a disease or condition associated with neo-angiogenesis is diagnosed when the comparison leads to the finding of a decrease of the expression level of said miRNA-9, miRNA-574, miRNA-7, miRNA-190b and/or miRNA-142 molecule, equivalent or a source thereof.

In a further preferred method, neo-angiogenesis or a disease or condition associated with neo-angiogenesis is diagnosed when the comparison leads to the finding of a decrease of the expression level of said miRNA-9, miRNA-574, miRNA-7, miRNA-190b and/or miRNA-142 molecule, equivalent or a source thereof and a decrease of the expression level of at least one of another miRNA selected from:
 a) a miRNA-9, a miRNA-190b, miRNA-7, miRNA-574 and/or a miRNA-142 molecule, and/or an equivalent and/or a source thereof,
 b) optionally at least one of a miRNA-26b, miRNA-27a, miRNA-92a, miRNA-221, miRNA-222, miRNA-145 and a let7a1 molecule an equivalent or a source thereof.

In a further preferred embodiment, neo-angiogenesis or a disease or condition associated with neo-angiogenesis is diagnosed when the comparison leads to the finding of a decrease of the expression level of said miRNA-9, miRNA-574, miRNA-7, miRNA-190b and/or miRNA-142 molecule, equivalent or a source thereof and/or a decrease of the expression level of at an increase of the expression level of at least one of another miRNA as identified above and/or an increase of the expression level of at least one of another miRNA selected from:
 a) a miRNA-132, miRNA-126 and/or a miRNA-21 or an equivalent or a source thereof.

In a further aspect, there is provided a method for identification of a substance or a molecule capable of preventing, treating, reverting, curing and/or delaying neo-angiogenesis or a condition or disease associated with neo-angiogenesis in a subject, the method comprising the steps of:
 (a) providing a test cell population capable of expressing a miRNA-9, miRNA-574, miRNA-7, miRNA-190b and/or miRNA-142 molecule or equivalent thereof or source thereof, preferably the test population comprises cancer cells and/or the test cell population comprises mammalian cells, and/or the test cell population comprises human cells;
 (b) contacting the test cell population with the substance;
 (c) determining the expression level of said miRNA-9, miRNA-574, miRNA-7, miRNA-190b and/or miRNA-142 molecule or equivalent thereof or source thereof or the activity or steady state level of said miRNA-9, miRNA-574, miRNA-7, miRNA-190b and/or miRNA-142 molecule or equivalent thereof or source thereof in the test cell population contacted with the substance;
 (d) comparing the expression, activity or steady state level determined in (c) with the expression, activity or steady state level of said miRNA-9, miRNA-574, miRNA-7, miRNA-190b and/or miRNA-142 molecule or equivalent thereof or source thereof in a test cell population that is not contacted with the substance; and,
 (e) identifying a substance that produces a difference in expression level, activity or steady state level of said miRNA-9, miRNA-574, miRNA-7, miRNA-190b and/or miRNA-142 molecule or equivalent thereof or source thereof, between the test cell population that is contacted with the substance and the test cell population that is not contacted with the substance.

Preferably, in step a), a test cell comprises a nucleic acid construct comprising a source or a precursor of a miRNA-9, miRNA-574, miRNA-7, miRNA-190b and/or miRNA-142 molecule or equivalent thereof or a precursor of said miRNA as identified earlier herein. Preferably, in a method the expression levels, an activity or steady state levels of more than one nucleotide sequence or more than one miRNA molecule, equivalent or source thereof are compared. Preferably, in a method, a test cell population comprises mammalian cells, more preferably human cells. More preferably, a test cell is an endothelial cell. A cell line may also be used as RF24. HUVEC cells may also be used. A preferred test cell population does not express a miRNA-9, miRNA-574, miRNA-7, miRNA-190b and/or miRNA-142 molecule or equivalent thereof or source thereof or has a reduced expression compared to a normal counterpart. More preferably, a test cell population comprises an endothelial cell. More preferably, a test cell population comprises 20%, 30%, 40%, 50%, 60%, 70%, 80%, 90% or 100% of endothelial cells. Endothelial cells may be identified by their expression of CD31 and CD34 markers. Alternatively or in addition to previous mentioned cells, in one aspect the invention also pertains to a substance that is identified in the aforementioned methods.

In a preferred method, the expression levels, activities or steady state levels of at least another one miRNA molecule or equivalent or source thereof is compared, preferably wherein the other miRNA molecule or equivalent or source thereof is selected from:
 a) a miRNA-9, a miRNA-190b, a miRNA-7, a miRNA-574 and/or a miRNA-142 molecule, and/an equivalent and/or a source thereof,
 b) optionally at least one of miRNA-26b, miRNA-27a, miRNA-92a, miRNA-221, miRNA-222, miRNA-145, let7a1, miRNA-132, miRNA-126 and miRNA-21 molecule an equivalent or a source thereof.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are transcribed from non-protein-encoding genes. A precursor may have a length of at least 50, 70, 75, 80, 85, 100, 150, 200 nucleotides ore more. The precursor miRNAs have two regions of complementarity that enables them to form a stem-loop- or fold-back-like structure, which is cleaved by enzymes called Dicer and Drosha in animals. Dicer and Drosha are ribonuclease Ill-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or equivalents or source thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand.

Two designs incorporate chemical modifications of the complementary strand. The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others. The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand. Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

MiRNA Libraries

A key application for the miRNAs as identified herein is the assessment or diagnosis of the presence of one individual or groups of miRNAs in a sample. Cell populations with each of the different miRNAs can then be assayed to identify miRNAs whose presence affects a cellular phenotype (i.e. neo-angiogenesis). The number of different miRNAs in the libraries is variable. It is contemplated that there may be, be at least, or be at most 1, 2, 3, 4, 5, 6, 7, 8, 9, 10, 11, 12, 13, 14, 15, 16, 17, 18, 19, 20 or more, or any range derivable therein, different miRNA-specific molecules in the library. In specific embodiments, libraries have 1 to 20 different miRNA-specific molecules, or 5 to 20 different miRNA-specific molecules. "Different" miRNA-specific molecules refers to nucleic acids that specifically encode miRNAs with different sequences.

miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs (Peptide Nucleic Acids). Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or equivalent thereof has a sequence that derives from any of SEQ ID NOs: 22-52 (Table 5). It is particularly contemplated that nucleic acid molecules of the invention may be derived from any of the mature miRNA sequences in SEQ ID NOs: 22-52.

A miRNA molecule or equivalent thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

Libraries of the invention can contain miRNA sequences from any organism having miRNAs, specifically including but not limited to, mammals such as humans, non human primates, rats and mice. Specifically contemplated are libraries having, having at least, or having at most 1, 2, 3, 4, 5, 6, 7, 8, 9, 10, 11, 12, 13, 14, 15, 16, 17, 18, 19, or more different miRNAs (that is, miRNA-specific molecules having different sequences derived from different miRNA genes). Specifically contemplated are such libraries described in the previous sentence with respect to any of SEQ ID NOs: 22-52 particularly those corresponding to miRNA sequences (mature sequence).

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 4 indicates which SEQ ID NO corresponds to a particular precursor sequence of a miRNA (SEQ ID NO: 1-21) and Table 5 indicates which SEQ ID NO corresponds to the mature or mimic sequence of a miRNA (SEQ ID NO: 22-52. Table 6 identifies the cloned DNA sequences into the lentiviral vector (SEQ ID NO: 53-60 which were used in the functional screen as described in the examples. Tables 5 and 7 identify the preferred seed sequences (as SEQ ID NO: 348-378, 61-115 and 379-381) of each of the mature miRNAs of Table 5. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below.

Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs: 22-52 or are described in SEQ ID NOs: 116-304 and 382-396. It is contemplated that nucleic acids sequences of the invention derived from SEQ ID NO: 22-52 and/or 116-304 and/or 382-396 can have, have at least, or have at most 5, 6, 7, 8, 9, 10, 11, 12, 13, 14, 15, 16, 17, 18, 19, 20, 21, 22, 23, contiguous nucleotides from SEQ ID NOs: 22-52 or 116-304 or 382-396 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs: 22-52 or 116-304 or 382-396 or to the precursor sequence of any of SEQ ID NO: 1-21 or 53-60 or any combination or range derivable therein.

Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2' and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to,
1) ribose modifications (such as 2'F, 2' NH2, 2'N3,4' thio, or 2' O—CH3) and
2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5'OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acids

A nucleic acid may be made by any technique known to one of ordinary skill in the art, such as for example, chemical synthesis, enzymatic production or biological production. Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. Nos. 4,704,362, 5,221,619, and 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, NH2, biotin, an amine group, a lower alkylamine group, an acetyl group, 2' O-Me, DMTO, fluoroscein, a thiol, or acridine or any other group with this type of functionality.

Other sense strand modifications. The introduction of nucleotide modifications like 2'-O Me, 2'-deoxy, T-deoxy-2'-fluoro, 2'-O-methyl, 2'-O-methoxyethyl (2'-O-MOE), 2'-β-aminopropyl (2'-O-AP), 2'-O-dimethylaminoethyl (2'-O-DMAOE), 2'-β-dimethylaminopropyl (2'-O-DMAP), 2'-O— dimethylaminoethyloxyethyl (2'-β-DMAEOE), or 2'-O—N-methylacetamido (2'-0-NMA), NH2, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial or endothelial cells, stromal cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, stem cells, liver, lung, bone, breast, cervix, colon, endometrium, epithelial, esophagus, goblet cells, kidney, ovaries, pancreas, prostate, bladder, skin, small intestine, stomach, testes, heart, blood vessel.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a screening method, or it may be related to a therapeutic or diagnostic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209).

Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S., et al, Trends Mol. Med., 2009, 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonculeotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospholipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic acid to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, *Drosphila antennapedia*, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4',5,5'-hexachlorobiphenyl (Borlakoglu et al, 1990) could enhance cellular uptake, and improve nuclease resistance by promoting lipoprotein association.

Screening with miRNA Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development.

In some embodiments, there is a multi-step process for screening, in certain embodiments, there are four general steps:

(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium.

Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes. Alternative screening methods exist using batch infection.

(2) Optimize Transfection Conditions for the Desired Cells.

The first step in this process is identifying a transfection reagent and plating conditions that maximize the uptake of synthetic miRNAs while maintaining high cell viability. We find it useful to test 2-5 different transfection reagents when using cell lines or 5-10 electroporation conditions when using primary or suspension cells. Transfection can be optimized for the reagent or electroporation condition that worked best among the conditions tested. Screening miRNA-specific libraries requires conditions for high-throughput transfection. In this type of screen, lentiviral introduction rather than transfection was used. This may require alternative optimization techniques.

(3) Screen

Once the assay and transfection process have been developed, a library of synthetic miRNAs or miRNAs expressed by viruses can be introduced sequentially into cells in a 24- or 96-well plate. Duplicate or Triplicate transfections for each reagent provide enough data for reasonable statistical analysis. MTS assay as carried out in the experimental part is an example of such a screen.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed. Confirmation is slightly different from validation. Confirmation is a repeat of the miRNA-induced phenotype, whereas validation can also include reversal of the phenotype by antagonizing miRNA mediated phenotype.

Labeling and Labeling Techniques

In some embodiments, the present invention concerns miRNAs that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNAs may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and IDT. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N-(4-amino)butyl-dATP, $N^6$-(6-amino)butyl-dATP, $N^4$-[2,2-oxy-to-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled, in embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNAs is how to label the already existing molecule. To this end, we may use an enzyme capable of using a di- or tri-phosphate ribonucleotide or deoxyribonucleotide as a substrate for its addition to an miRNA, a small RNA molecule. Moreover, in specific embodiments, it involves using a modified di- or triphosphate ribonucleotide, which is added to the 3' end of an miRNA. The source of the enzyme is not limiting. Examples of sources for the enzymes include yeast, gram-negative bacteria such as E. coli, lactococcus lactis, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al, RNA, 4(2):226-30, 1998).

Terminal transferase catalyzes the addition of nucleotides to the 3' terminus of a nucleic acid.

Polynucleotide phosphorylase can polymerize nucleotide diphosphates without the need for a primer.

Labels and Tags miRNAs or miRNA probes may be labeled with a positron emitting (including radioactive), enzymatic, colorimetric (includes visible and UV spectrum, including fluorescent), luminescent or other label or tag for detection or isolation purposes. The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, AMCA, Alexa Fluor dyes, BODIPY dyes, such as BODIPY FL, BODIPY 630/650, BODIPY 650/665, BODIPY-R6G, BODIPY-TRX; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red;

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODEPY 530/550, BODEPY 558/568, BODIPY 564/570, BODDPY 576/589, BODIPY 581/591, BODEPY 630/650, BODIPY 650/655, BODIPY FL, BODIPY R6G, BODEPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODEPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP. Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODEPY FL-14-dUTP, Rhodamine Green-5-dUTP, Alexa Fluor 532-5-dUTP, BODEPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODEPY TR-14-dUTP, Alexa Fluor 594-5-dUTP, BODEPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference). Fluorescent energy transfer dyes, such as thiazole orange-ethidium heterodimer; and, TOTAB may be used.

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al, 1997, spectroscopy, capillary gel electrophoresis (Cummins et ah, 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule (Acumen [TTP Labtech] plate cytometer for example.

Array Preparation

The present invention can be employed with miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference. It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments, hi certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO03067217; WO 03066906; WO 03076928; WO 03093810; WO 03100448A1, all of which are specifically incorporated by reference.

Recently, alternative profiling methods have become availables, based on solution hybridization and subsequent immobiliztion and identification e.g. Illumina platform.

Sample Preparation

It is contemplated that the miRNA of a wide variety of samples can be analyzed using assays described herein. While endogenous miRNA is contemplated for use with some embodiments, recombinant or synthetic miRNA—including nucleic acids that are identical to endogenous miRNA or precursor miRNA—can also be handled and analyzed as described herein. Samples may be biological samples, in which case, they can be from blood, CSF, tissue, organs, tumor, semen, sputum, stool, urine, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

Cell Assays to Identify miRNAs with Ties to Disease

Specifically contemplated applications include identifying miRNAs that contribute to decrease neo-angiogenesis and/or induce anti-angiogenic activity that are themselves parts of a disease or conditions or might otherwise be associated with a particular disease state. Additionally, a contemplated application includes the identification of miRNAs that are able to decrease neo-angiogenesis and/or induce anti-angiogenic activity. Also, miRNA functions may be compared between a sample believed to be susceptible to a particular disease or condition associated with neo-angiogenesis and one believed to be not susceptible or resistant to that disease or condition. It is specifically contemplated that RNA molecules of the present invention can be used to treat any of the diseases or conditions discussed in the previous section or modulate any of the cellular pathways discussed in the previous section. Specifically contemplated applications include identifying miRNAs that contribute to neo-angiogenesis cellular processes and/or induce an anti-angiogenic activity that are themselves parts of a disease or might otherwise be associated with a particular disease state. Also, miRNA functions may be compared between a sample believed to be susceptible to a particular disease or condition associated with neo-angiogenesis and one believed to be not susceptible or resistant to that disease or condition.

The efficacy of different therapeutic drugs may be altered by miRNAs as defined and used according to the present invention. MiRNA molecule, equivalent or source thereof that decrease neo-angiogenesis and/or induce an anti-angiogenic activity may enhance susceptibility to e.g. chemo and immunotherapy. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY1 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-α, Raf and H-Ras; ribozymes such as a VEGF expression inhibitor and a HER2 expression inhibitor; vaccines such as gene therapy vaccines and pharmaceutically acceptable salts, acids or derivatives of any of the above. A list of U.S. FDA approved oncology drugs with their approved indications can be found on the World Wide Web at accessdata.fda.gov/scripts/cder/onctools/druglist.cfm. Moreover, it is contemplated that samples that have differences in the activity of certain pathways may also be compared. Such cellular pathways include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-I, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, Rho A, Rac, myosin light chain kinase, platelet-derived growth factor receptor or ezrin; any apoptosis pathway including but not limited to those involving AKT, Fas ligand, NFKB, caspase-9, PB kinase, caspase-3, caspase-7, ICAD, CAD, EndoG, Granzyme B, Bad, Bax, Bid, Bak, APAF-I, cytochrome C, p53, ATM, Bcl-2, PARP, Chk1, Chk2, Rho-21, c-Jun, Rho73, Rad51, Mdm2, Rad50, c-Abl, BRCA-I, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, H2O2, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RTP, cyclin-D1, PCNA, BcI-XL, PIP2, PIP3, PTEN, ATM, Cdc2, protein kinase C, calcineurin, IKKα, IKKβ, IKKγ, SOS-I, c-FOS, Traf-1, Traf-2, IKBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p34, p20, PP2A, angiotensin, angiotensin-converting enzyme, protease-activated receptor-1, protease-activated receptor-4, Ras, RAF-I, PLCβ, PLCγ, COX-I, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCCl, CD40, CD40 ligand, p38, DCKα, IKKβ, NFKB, TRAF2, TRAF3, TRAF5, TRAF6, IL-4, IL-4 receptor, CDK5, AP-I transcription factor, CD45, CD4, T cell receptors, MAP kinase, nerve growth factor, nerve growth factor receptor, c-Jun, c-Fos, Jun kinase, GRB2, SOS-I, ERK-I, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-I, BRCA-2, SKP1, the proteasome, CUL1, E2F, pi 07, steroid hormones, steroid hormone receptors, IκBα, IκBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCCl, Sonic Hedgehog, Crml, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, 1 KB, NFKB, RACl, RAFl, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-I receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a miRNA molecule, equivalent, mimic or source thereof inhibits, eliminate, activates, induces, increases, or otherwise modulates one or more of the above pathways or factors is contemplated as part of methods of the invention. The nucleic acid can be used to diagnosis a disease or condition based on the relation of that miRNA to any of the pathways described above.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic and Diagnostic Applications miRNAs that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with neo-angiogenesis as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention. In vivo experiments, a miRNA sequence may differ in the test animal as compared to the human sequence. In that case, a miRNA that differs from the human sequence might be used to demonstrate therapeutic effect in the animal. Results obtained with this sequence tested in an animal may be extrapolated expected results in human with a corresponding miRNA molecule.

Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the miRNA into preparations which can be used pharmaceutically. Proper formulation is dependent upon the route of administration chosen. For topical administration the miRNAs of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine. Nucleic acids may also be conjugated to a chemical moiety, such as transferrin and cholesteryls. In addition, oligonucleotides may be targeted to certain organs or tissues by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor, also called transferring modified cyclodextrin (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin A5 (targeting phophatidylserine exposing membranes, Garnier B. et al., Bioconjug Chem., 2009, 11:2114-22), WO 2009/126933 describing compositions and methods for site-specific delivery of nucleic acids by combining them with targeting ligands and endosomolytic components. Targeting ligands that are preferentially suitable are endothelial-associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

In addition to the above, a molecule of the invention may be delivered using electroporation for local or targeted treatment. Electroporation methods are known to the skilled person and are for example described in Daud et al (2008) or Bodles-Brakhop (2009). Each of these publications is incorporated by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The miRNAs may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise 2% to 75% of the weight of the unit, or 25% to 60%, for example, and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. 1, p. 1).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Kits

Any of the compositions described herein may be comprised in a kit. In a non-limiting example, individual miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the miRNA to cells.

In another non-limiting example, multiple synthetic miRNAs are included in a kit. The kit may further include one or more negative control synthetic miRNAs that can be used to control for the effects of synthetic miRNA delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: miRNA, library of miRNAs, combination library of miRNA, negative control miRNA, nuclease-free water; RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). In an embodiment, identity is assessed on a whole length of a given SEQ ID NO.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA, an equivalent, a mimic or a source or an antagomir thereof or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 3A represents the average absorbance data of plate 7 with RF24 cells while FIG. 3B represents the average absorbance data with HUVEC cells. The hits that were selected for hit-confirmation are indicated by spheres.

FIG. 12A, FIG. 12B, FIG. 12C, FIG. 12D and FIG. 12E: Tumor growth curves of Neuro2A tumor bearing mice treated locally with PBS(n=6) or with miR-scrambled (n=6) or with synthetic anti-angiogenic miRNAs or with siVEGFR2; FIG. 12A tumors treated with miR-7 (n=7); FIG. 12B tumors treated with miR-574-5p (n=7); FIG. 12C tumors treated locally with miR-27a (n=7); FIG. 12D tumors treated with the positive control siVEGFR-2 (n=7); FIG. 12E Tumors treated with miR-9* (n=8). The results depicted in FIG. 12E originate from a different mice cohort than the results depicted in FIGS. 12A-D. The PBS tumor growth curve was generated with n=8 mice, while the miR-scrambled tumor growth curve was generated with n=10 mice. Tumor volumes are depicted as mean±STDEV.

Figure 1A:
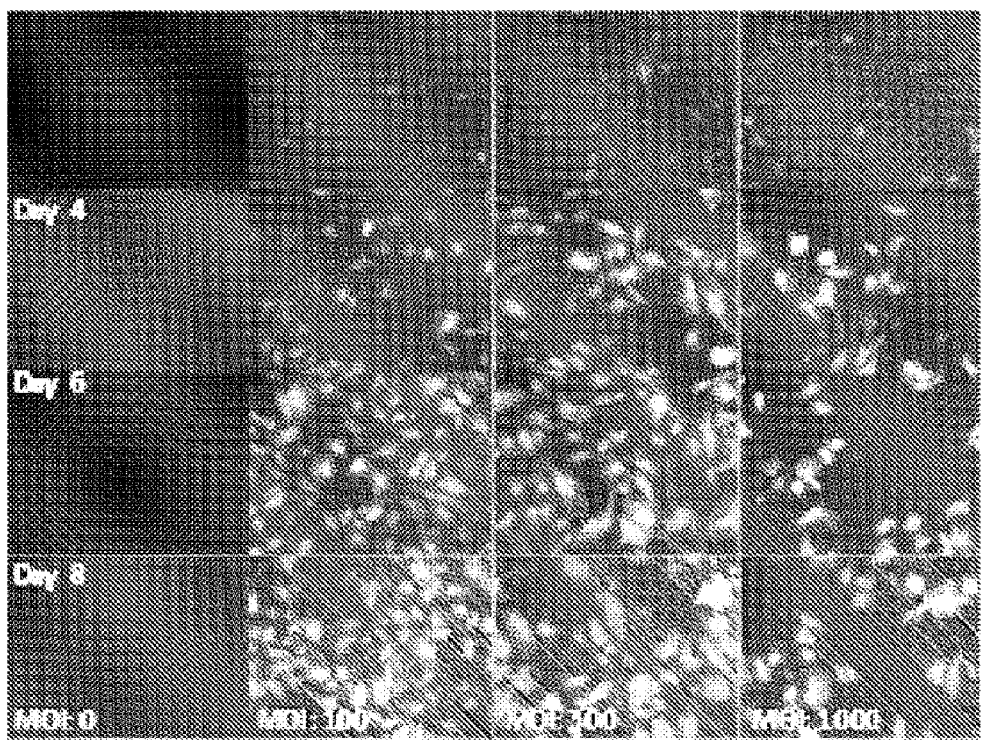
FIG. 1A and FIG. 1B provide a representative example of the transduction efficiency as a function of MOI and time after lentiviral transduction is shown for HUVEC cells with 8 µg/ml polybrene (FIG. 1A) and for RF24 cells with 6 µg/ml polybrene (FIG. 1B). These examples show that that both HUVECs and RF24 cells are highly transducable (>95%) with lenti-copGFP. To assess the angiogenic potential of miRNAs in endothelial cells, functional screens were performed by transduction of the complete lentiviral miRNA library in human umbilical vein endothelial cells (HUVECs) and RF24 cells (immortalized endothelial cell line). The following parameters were optimized for optimal assay performance using a control lentivirus with Green Fluorescent Protein (lenti-copGFP): cell number, lentivirus particle dose (MOI, for efficiency and optimal miRNA expression), time between lentiviral transduction and readout of the MTS assay.

Quantification of microvessel density (MVD) of CD31 stained Neuro2A tumors treated with PBS, miR-scrambled, miR-574-5p, miR-7, miR-27a or siVEGFR2. Data are presented as mean±STDEV. **$P<0.01$ versus miR-Scrambled. 1-way ANOVA test.

EXAMPLES

Materials and Methods
Cell Culture and Chemicals
EC-RF24 Vascular Endothelial Cells (ABM#T0003)
HUVECs (Human Umbilical Vein Endothelial Cells) P4 (Lonza#cc-2519) used throughout the examples unless otherwise indicated.
M199 medium (Gibco#22340-087)
Fetal Bovine Serum (FBS) (Sigma#F7524, Lot#059K3395)
Human Serum (HS) (Sigma#118K0494, Lot#H6914-100 ml)
10.000 U/ml Penicillin/Streptavidin (P/S) (Biochrom AG#A2213)
200 nM L-glutamin (Sigma#G7513, Lot#RNBB0722)
1% (m/V) gelatin (Sigma)
10×PBS (Gibco#14200-067)
TrypLE Express (Gibco#12605)
0.4% Trypan Blue Stain (Lonza#17-942E)
1 mg/ml polybrene (Sigma) in 1×PBS
Lentiviral-based microRNA (over)expressing library (14 plates)
CellTiter 96® AQUEOUS One Solution Cell Proliferation Assay (MTS)
(Promega#G3580)
Multifuge X3R (Thermo scientific)
Multiskan FC (Thermo Scientific)
Medium
Specific growth medium HUVECs: M199+100 U/ml P/S+2 mM L-glutamin+10% FBS+10% HS.
Specific growth medium RF24 cells: M199+100 U/ml P/S+2 mM L-glutamin+10% FBS.

Example 1

Generation of the Lentiviral Library Encoding miRNAs

Human miRNAs were selected from both the public miRNA repository (www.mirbase.org) and proprietary small RNA deep sequencing data (see WO 2007/081204). The miRNA sequences were amplified from their genomic location with amplicons containing the full-length pre-miRNA hairpin and a flanking sequence on both sides of 50-150 basepairs. The primers for the amplicons were designed using a custom implementation of the Primer3 software (www.geneious.com). If the primer design program could not find appropriate primers in the designated sequences, the requirements for the flanking sequences were adjusted to 0-200 basepairs. The designed primers were complemented with a 5' GCGC overhang and a restriction site for directional cloning. As default the primer upstream of the miRNA was complemented with a BamHI restriction site (GGATCC) and the primer downstream of the miRNA was complemented with an EcoRI restriction site (GAATTC). Primers of amplicons with internal BamHI or EcoRI restriction sites (i.e. occurring in the genomic sequence) were complemented with either a BglII site (AGATCT) or a XbaI site (TCTAGA) respectively. The miRNAs were amplified using the above-mentioned primers from human genomic DNA of a single individual in the following PCR reaction:

| constituent | concentration | volume | supplier/cat # |
|---|---|---|---|
| buffer | 10X | 1 µl | Stratagene/600159 |
| dNTPs | 10 mM each | 0.2 µl | GE Healthcare/27-18(58) 0-04 |
| fwd primer | 10 µM | 0.2 µl | Integrated DNA Technologies |
| rev primer | 10 µM | 0.2µ | IIntegrated DNA Technologie |
| gDNA | 100 ng/µl | 0.1 µl | private source |
| Pfu DNA pol | 2.5 U/µl | 0.1 µl | Stratagene/600159 |
| H₂O | | 8.2 µl | |

| temp (° C.) | time | cycles | |
|---|---|---|---|
| 95 | 2 min | — | |
| 95 | 15 s | 40 | |
| 59* | 15 s | 40 | * −0.1° C./cycle |
| 72 | 90 s | 40 | |
| 72 | 15 min | | |
| 4 | ∞ | | |

All miRNA loci were amplified in separate 10 µl PCR reactions. The products were purified using the Qiagen PCR Clean-Up buffer set and Whatman Unifilter GF/C filter plates (cat #7700-1101). DNA was eluted with 17 µl H₂0 per well. The separate eluates were used in the following restriction reaction:

| Constituent | concentration | volume | supplier/cat # |
|---|---|---|---|
| buffer | E 10X | 2 µl | Promega/R005A |
| EcoRI* | 12 U/µl | 0.1 µl | Promega/R6017 |
| BamHI* | 10 U/µl | 0.1 µl | Promega/R6025 |
| eluate | N/A | 16 µl | N/A |
| H₂O | N/A | 1.8 µl | N/A |

*Amplicons with internal restriction sites for EcoRI or BamHI were cut with XbaI or BglII respectively instead. The EcoRI + BglII reaction was done with Promega buffer D. The BamHI + XbaI reaction was done with Promega buffer E.

| constituent | concentration | volume | supplier/cat # |
|---|---|---|---|
| buffer | 10X | 2 µl | Promega/C1263 |
| T4 DNA ligase | 1-3 U/µl | 0.2 µl | Promega/M1804 |
| restricted pCDH* | 1 ng/µl | 7.8 µl | System Biosciences/CD510B-1 |
| eluate | N/A | 10 µl | N/A |
| Ligation overnight at 4° C. | | | |

*For directional cloning, pCDH was cut with both EcoRI and BamHI. An alternate construct called pCDH- was made with reversed EcoRI and BamHI restriction sites so that the amplicons with 5' BamHI and 3' EcoRI were cloned in the proper direction. The amplicons with an internal EcoRI site were cut with XbaI and ligated into a pCDH vector that was restricted with XbaI and BamHI.

The resulting ligates were transformed separately into bacteria (Promega Single Step (KRX) competent cells, cat #L3002). 50 µl competent cells was diluted with 950 µl transformation buffer II (10 mM MOPS, 75 mM CaCl₂, 10 mM RbCl, 15% glycerol, filter-sterilized). Per 20 µl ligate, 20 µl diluted competent cells was added. The mix was incubated for 15 minutes on ice, heat-shocked at 37° C. for 30 seconds, and put back on ice. After 2 minutes the transformed bacteria were reconstituted in 150 µl Luria broth (LB). The bacteria were allowed to recover for 20 minutes at 37° C. after which they were plated out separately on ampicillin-containing (50 ug/mL) LB-agar plates and grown overnight at 37° C.

Single colonies of each plate are picked and subcultured overnight in 400 µl ampicillin-containing (50 ug/mL) LB. 1 µl of subculture is lysed in 100 µl water for sequencing purposes. Bacterial lysate is used in the following PCR reaction:

| constituent | concentration | volume | supplier/cat # |
|---|---|---|---|
| buffer | 5X | 1 µl | private source |
| dNTPs | 10 mM each | 0.1 µl | GE Healthcare/27-18(5-8)0-04 |
| pCDH-fwd | 10 uM | 0.1 µl | Integrated DANN Technologies |
| pCDH-rev | 10 uM | 0.1 µl | Integrated DANN Technologies |
| lysate | 1:100 | 1 µl | N/A |
| Taq DNA pol | unknown | 0.02 µl | private source |
| H₂O | N/A | 2.68 µl | N/A |

| temp (° C.) | time | cycles | |
|---|---|---|---|
| 95 | 2 min | — | |
| 95 | 15 s | 40 | |
| 59* | 15 s | 40 | * −0.1° C./cycle |
| 72 | 90 s | 40 | |
| 72 | 15 min | | |
| 4 | ∞ | | |

(SEQ ID NOs: 311 and 312)
pCDH-fwd
CACGCTGTTTTGACCTCCATAGA pCDH-rev
CACTGACGGGCACCGGAG The PCR products were diluted 25×. 1 µl of diluted PCR product was used in the following Sanger Sequencing reaction:

| Constituent | concentration | volume | supplier/cat # |
|---|---|---|---|
| buffer | N/A | 1.9 µl | private source |
| BigDye v3.1 | N/A | 0.1 µl | ABI/4336921 |
| pCDH-seq | 10 uM | 0.1 µl | IDT (Integrated DNA Technologies) |
| PCR product | 1:25 | 1 µl | N/A |
| H₂O | N/A | 1.9 µl | N/A |

| temp (° C.) | time | cycles |
|---|---|---|
| 94 | 10 sec | — |
| 50 | 5 s | 40 |
| 60 | 2 min | 40 |
| 10 | ∞ | | pCDH-seq
(SEQ ID NO: 313)
GACCTCCATAGAAGATTCTAGAGCTAGC

30 µl precipitation mix (80% ethanol, 50 mM sodium acetate pH 5.5) was added to each of the sequencing reaction products. The mixes were vortexed for 10 seconds and spun down at 5000 rcf (relative centrifugal force) for 45 minutes at 4° C. Supernatant was aspirated and DNA pellets were washed with 30 µl ice cold 80% ethanol and spun at 5000 rcf for 5 minutes at 4° C. Supernatant was aspirated and the DNA pellet was dried on a heat block for 10 minutes. The dry DNA pellet was dissolved in 10 µl H₂O. The resulting DNA solution was sequenced on an ABI 3730XL DNA Analyzer. Sequences were compared to the expected genomic sequences. Correct clones were added to the library. For incorrect clones an additional 4 bacterial colonies were picked, and analyzed for insert sequence.

Library constructs were subcultured overnight in 50 mL ampicillin-containing (100 ug/mL) LB and isolated with the Qiagen QIAfilter Plasmid Midi Kit (cat #12245) supplemented with the Qiagen EndoFree Plasmid Buffer Set (cat #19048) according to the instructions of the manufacturer. DNA was dissolved in the supplied TE buffer and brought to a final concentration of 500 ng/µl.

We ordered constructs that we were not able to clone ourselves as minigenes from Integrated DNA Technologies. In these cases, the full-length hairpin plus 20 basepairs flanking each site were cloned into our vector as a service by IDT.

Packaging and virus production was performed by System Biosciences as described in the user manual of CD-500B1-CD523-A1.

Example 2

Viral Transduction and Screening

Day-8: Start cell growth of RF24 cells and HUVECs in a T25 culture flask Coat a T25 culture flask per cell type with 2 ml 1% gelatin for an hour at 37° C. Thaw cells (these cells were frozen in 95% corresponding medium and 5% DMSO) obtained from the −80° C. deep freezer at 37° C. in a water bath. Clean the vial with 70% ethanol and transfer the cells in the culture flasks with 5 ml of the appropriate growth medium and place at 37° C., 95% humidity and 5% $CO_2$. 4 hours after seeding, the DMSO containing medium must be replaced by fresh warm culture medium. The cells are subsequently incubated for three days at 37° C., 95% humidity and 5% $CO_2$.

Day-5: Transfer of RF24 cells and HUVECs to a T75 culture flask

Coat a T75 culture flask per cell line with 6 ml 1% gelatin for an hour at 37° C.

Remove gelatin.

Wash the T25 culture flask with cells once with 1×PBS.

Spread 0.5 ml TrypLE Express evenly over the cell surface and remove the excess.

Incubate at room temperature until all cells have detached.

Resuspend the cells in 15 ml cell specific growth medium (as done before) and incubate the cells in a T75 culture flask at 37° C., 95% humidity and 5% $CO_2$.

Day-1: Seeding of RF24 cells and HUVECs in 96 well plates

Protocol per plate (everything is performed in duplo):

Coat the 96 well plates with 30 µl/well 1% gelatin for an hour at 37° C.

Wash the T75 culture flask with cells once with 1×PBS.

Spread 1.0 ml TrypLE Express evenly over the cell surface and remove the excess.

Incubate at room temperature until all cells have detached.

Inactivate the trypsin process through addition of 5 ml/T75 fresh specific growth medium.

Add 20 µl 0.4% trypan blue solution to the same volume of cell suspension and count the cells using the Fuchs-Rosenthal chamber. This is done by counting 3 of the 16 squares consisting of 16 squares each. To calculate the amount of cells (n) per ml the average cell number is corrected for dilution and multiplied by 5000 (c/ml=n×2× 5000).

To seed one 96 well plate with RF24 cells at a concentration of 1500 cells/well, 1.8E+5 cells need to be suspended in an end volume of 18 ml. 150 µl suspension is to be added to each well.

To seed one 96 well plate with HUVECs at a concentration of 2000 cells/well, 2.4E+5 cells need to be suspended in an end volume of 18 ml. 150 µl suspension is to be added to each well.

The plated cells will be incubated at 37° C., 95% humidity and 5% $CO_2$ overnight.

Note: one seeded plate will be taken into the screen without transducing the cells, to get a better understanding of plate effects.

Day 0: Transduction of RF24 cells and HUVECs in the morning

First polybrene is added to the 96 well plates. HUVECs will be exposed to 6 µg/ml and RF24 cells to 8 µg/ml polybrene in PBS.

Per plate:

HUVECs: To 1270 µl PBS, 200 µl polybrene (1 mg/ml in PBS) is added to get 136 µg/ml polybrene. 10*136=170*8. End concentration: 8 µg/ml polybrene in 170 µl.

Figure 1B:
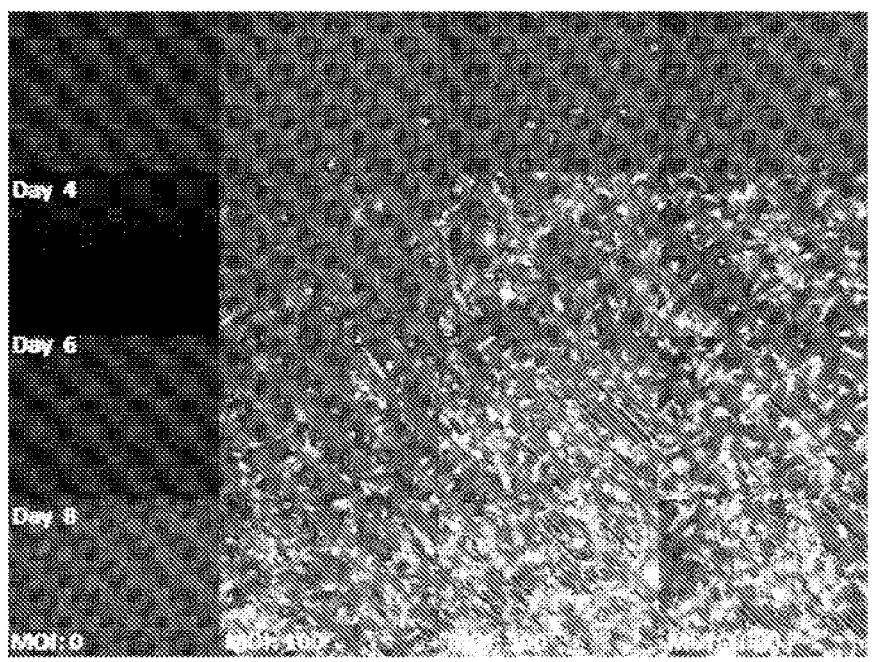
Figure 2A:
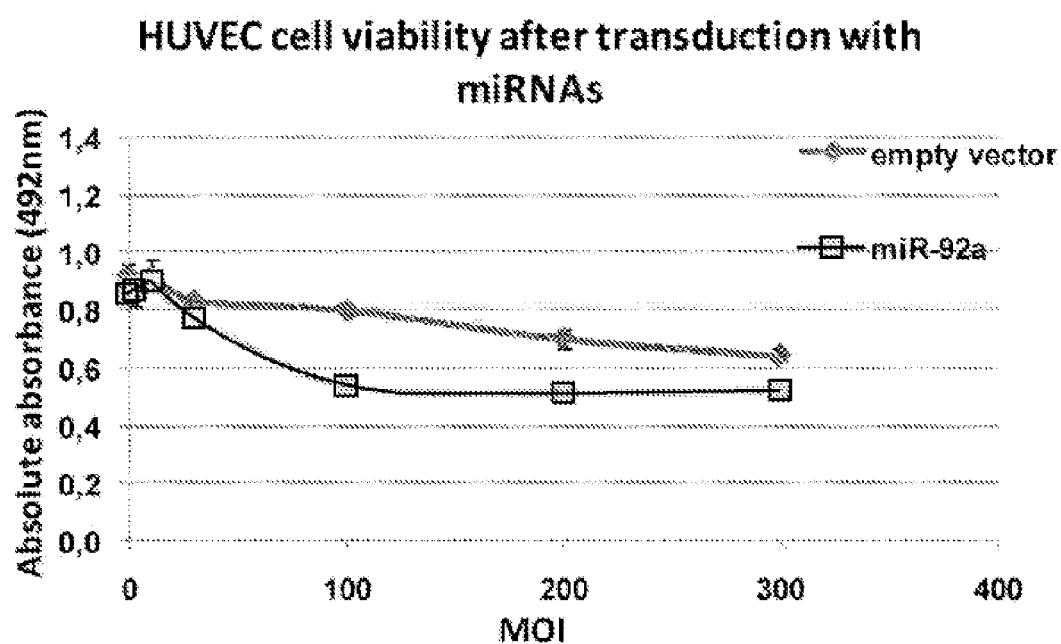
FIG. 2A and FIG. 2C show that the largest window between positive and negative control is observed between MOI of 30 and 100 for both RF24 cells (FIG. 2D) and HUVECs (FIG. 2B). The optimal assay conditions (assay-window; Z' factor) were established using the pCDH-CMV-MCS-EF1-Puro vector expressing miR-92a (proliferation/survival) as a positive control, and an empty pCDH-CMV-MCS-EF1-Puro vector as a negative control.
Figure 2B:
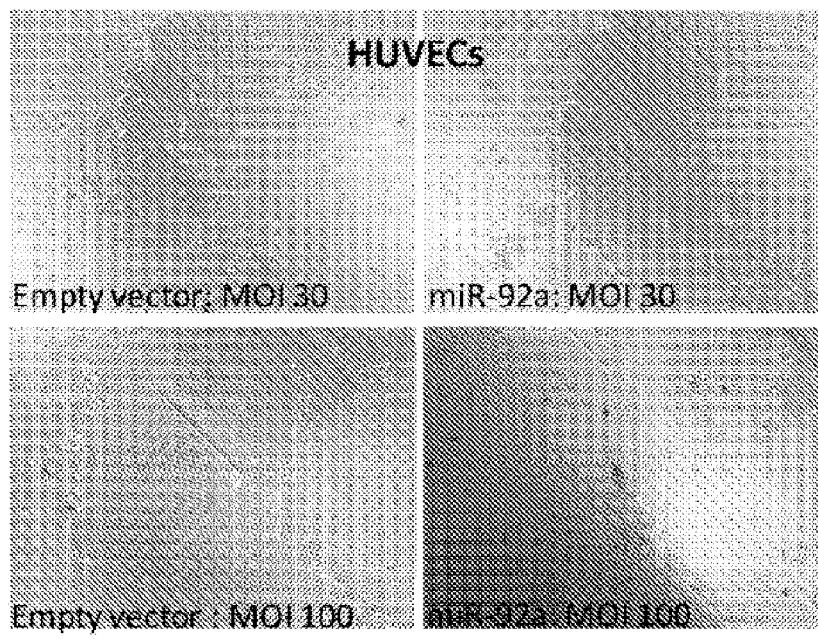
Figure 2C:
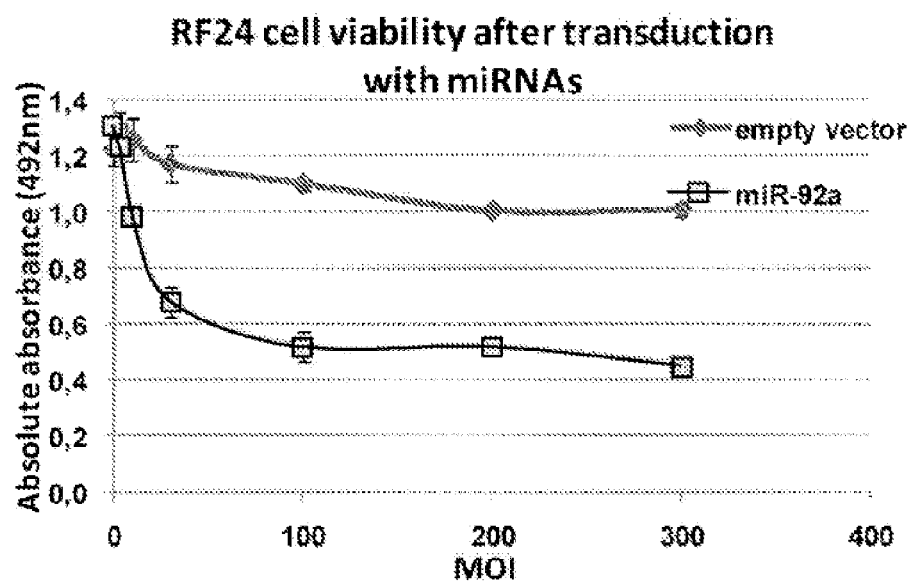
Figure 2D:
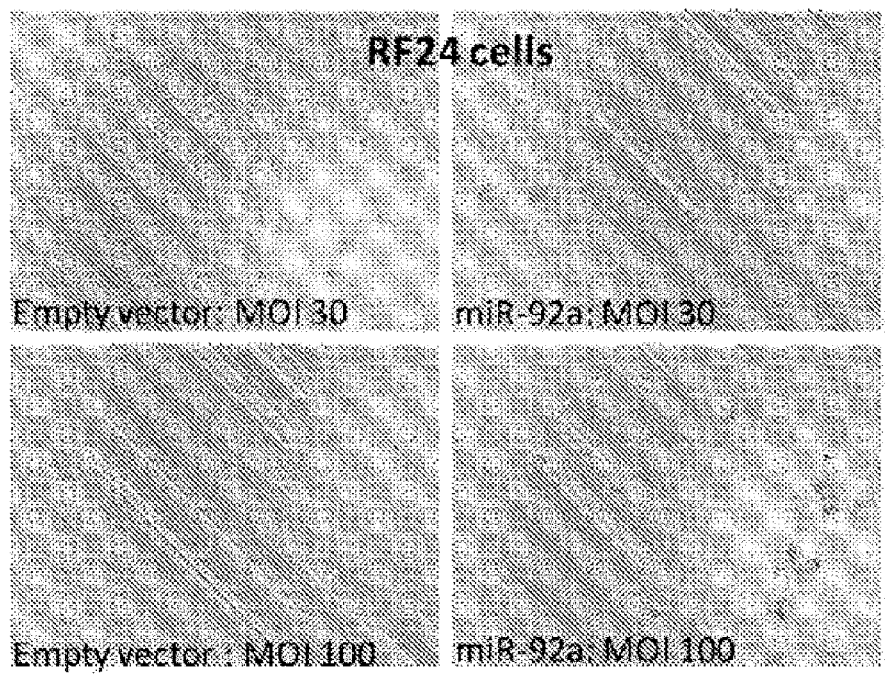

RF24 cells: To 1320 µl PBS, 150 µl polybrene (1 mg/ml in PBS) is added to get 96 µg/ml polybrene. 10*102=170*6. End concentration: 6 µg/ml polybrene in 170 µl. For every one of the 14 virus plates, depending on the titer, a specific volume will be added to the cells. This differs per cell line due to difference in seeding concentration. Ideally the amount of virus added should be around a Multiplicity of infection (MOI) of no more than 100 and no less than 50 in both cell lines (see FIGS. 1 and 2). Because every plate contains an array of totally different titers, the MOI should be no less than 50. All plates will be diluted 10 times in 1×PBS before addition. This is done to minimize pipetting errors. Because the polybrene concentration is set for a volume of 170 µl, and the volume will differ slightly per well, slight polybrene concentration differences will be unavoidable.

Add x µl virus to the cells (two plates per virus) to facilitate an MOI of 50 or higher and incubate at 37° C., 95% humidity and 5% $CO_2$ for 24 hours.

After transduction disinfect the flow cabinet by means of UV radiation before handling cells again.

As a control for plate effects, two non-treated plates will be incubated for 8 days together with the transduced plates.

Day 1: Medium refreshment of RF24 cells and HUVECs 24 hours after transduction Remove all virus containing medium using a multichannel and dispose of it according to the MLII procedure.

Add 150 µl fresh and warm (37° C.) medium to the cells and incubate at 37° C., 95% humidity and 5% $CO_2$. Also refresh medium untransduced plate(s).

Day 4: Medium refreshment of RF24 cells and HUVECs 96 hours after transduction Remove 100 µl virus containing medium using a multichannel and dispose of it according to the MLII protocols.

Add 100 µl fresh and warm (37° C.) medium to the cells and incubate at 37° C., 95% humidity and 5% $CO_2$.

Also refresh medium untransduced plate(s).

Day 7: Medium refreshment of RF24 cells and HUVECs 168 hours after transduction Remove all virus containing medium using a multichannel and dispose of it according to the MLII protocols.

Add 150 µl fresh and warm (37° C.) medium to the cells and incubate at 37° C., 95% humidity and 5% $CO_2$.

Also refresh medium untransduced plate(s).

Day 8: Cell viability assay, 8 days after transduction using MTS

Add 20 µl/well MTS solution to 150 µl medium.

Incubate at 37° C., 95% humidity and 5% $CO_2$ for 4 hours. Shake the plates so that all non dissolved crystals dissolve and measure the absorbance at 492 nm using the Multiskan FC.

Example 3

Hit Selection & Confirmation

To select the miRNAs that affect cell growth, the Z-score was chosen. To evaluate the normal distribution per plate and of combined plates, a distribution plot was made with the calculated median and standard deviation and with the actual values.

Several methods to calculate the Z-score were evaluated with different cut-offs:

Method 1:

This method calculates the individual miRNA Z-score per plate. The standard Z-score uses the mean and the SD of the miRNA population.

Method 2:

This method calculates the individual miRNA Robust Z-score per plate. The Robust Z-score uses the median and instead of the SD the median absolute deviation (MAD) multiplied with a given number (1.48) to simulate a normal population (Chung N. et al., J Biomol Screen 13:149-58, 2008).

The abovementioned methods were used to select the significant inhibitors and significant stimulators for the MTS screen. To evaluate the normal distribution per plate and of combined plates a distribution plot was made with the calculated median and standard deviation and with the actual values. The correlation between the individual MTS results of the duplicate tests was 0.85 and hit selection was performed using the average value.

Figure 3A:
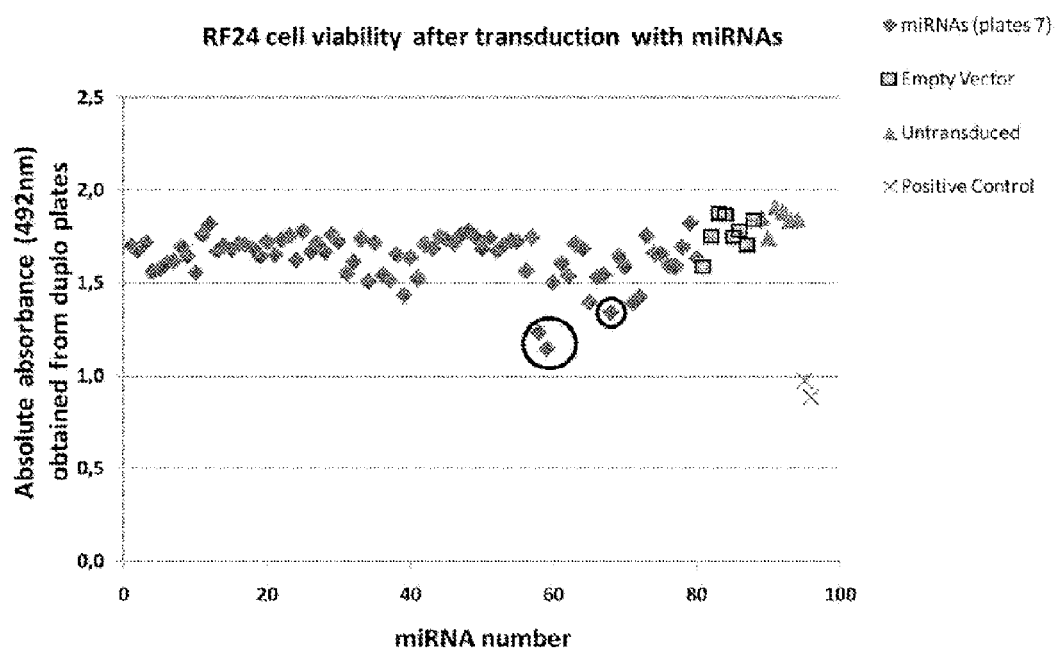
FIG. 3A and FIG. 3B represent an example of the screenings results by showing the average MTS absorbance data from plate 7.
Figure 3B:
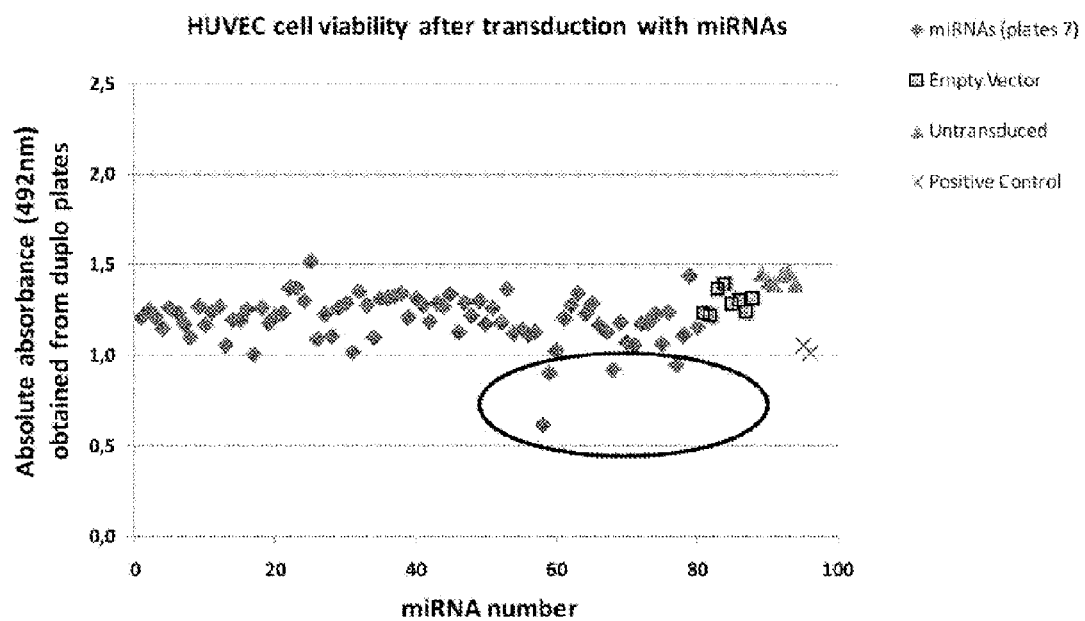

The library contains approximately 1120 miRNAs. All miRNAs were plated in fourteen 96-well plates, leaving the outer columns 1 and 12 vacant for positive (miR-92a-1) and an empty pCDH-CMV-MCS-EF1-Puro vector as a negative control. The library was screened in-duplo with a threshold of MOI 50 with HUVEC and RF24 endothelial cell line (FIG. 3). A total of 110 hits were selected. The next step was performing the hit confirmation with normalized titers per plate. This resulted in 39 reconfirmed hits, of which 6 were pro-proliferative. These hits were again confirmed by normalizing the titers per miRNA (MOI 100 and 200) to exclude viral toxicity or dose-dependent effects of individual miRNA's. In this experiment we used a control group of different empty vector population and non-responsive miR-NAs, in duplo and mirrored at plates, to further exclude plate effects. This resulted in the final miRNA hits which regulate proliferation in HUVEC and RF24 cells (Table 1).

TABLE 1 miRNA hits from normalized MTS assay depicted in delta absorbance. Population of Empty vector was used as control group.

| miRNA | Effect | HUVEC Delta Absorbance MOI 100 | HUVEC Delta Absorbance MOI 200 | RF24 Delta Absorbance MOI 100 | RF24 Delta Absorbance MOI 200 |
|---|---|---|---|---|---|
| hsa-mir-7-3 | Inhibitory | −0.73 | −0.79 | −0.82 | −0.90 |
| hsa-mir-26b | Inhibitory | −0.53 | −0.64 | −0.49 | −0.68 |
| hsa-mir-574 | Inhibitory | −0.52 | −0.54 | −0.13 | −0.02 |
| hsa-mir-27a | Inhibitory | −0.07 | −0.17 | −0.21 | −0.26 |
| hsa-mir-92a-1 | Inhibitory | 0.36 | −0.22 | 0.65 | 0.30 |
| hsa-mir-190b | Inhibitory | −0.49 | −0.56 | −0.43 | −0.45 |
| hsa-mir-142 | Inhibitory | −0.64 | −0.72 | −0.21 | −0.30 |
| hsa-mir-9-2 | Inhibitory | −0.52 | −0.59 | −0.26 | −0.56 |

Example 4

Total RNA Isolation

HUVEC and RF24 cells were seeded in a 24-well plate and were transduced at a MOI of 50 according to previous transduction protocols. At day 8 cells, cells were washed with ice cold PBS, 1 ml of PBS was added and the plate was put on ice. Cells were collected using a cell scraper and pipetted in an eppendorf tube. Cells were pelleted, PBS was aspirated and cells were frozen at −80° C.

For RNA isolation, cells were thawed on ice, 200 µl Trizol (Invitrogen, 15596-026) was added followed by a 5 minute incubation at room temperature. 40 µl Chloroform was added and tubes were shaken and incubated for 3 minutes. Samples were centrifuged at 12000×g for 15 minutes at 4° C. and two thirds of the upper aqueous layer was transferred to a non-stick RNAse free tube. The remaining aqueous layer was transferred to a different tube as back up.

1 µl of Glycoblue (Applied Biosystems, AM9510) was added to all samples together with 100 µl RNAse free iso-propanol and the RNA was precipitated at −20° C. overnight for the first batch and for two weeks for the backup batch. Samples were centrifuged at max speed for minimally 45 minutes at 4° C. and the pellet was washed with 200 µl 70% RNAse free ethanol. Samples were centrifuged at 7400×g for 5 minutes at 4° C. and supernatant was removed. The pellet was dried and dissolved in 25 µl $H_2O$ for the first batch and 15 µl nuclease free $H_2O$ for the backup batch.

The RNA kit for the Qubit (Invitrogen) was used according to protocol to measure the final RNA concentration.

Example 5

Stem-Loop RT-PCR and qPCR

MicroRNA expression was determined by stem-loop RT-PCR as described (Chen, C. et al Nucleic Acids Res. 33: e179 (2005)). For the stem loop RT-PCR, stem loop primers were designed for each individual miRNA according to the mature sequences in mirBase 15 and 16 and if present an isoform thereof. For the qPCR individual forward primers were designed also according to the mature miRNA sequence in mirBase 15 and 16 (see below). The universal reverse primer was designed for the stem-loop sequence (see below). As a household gene U6 was used.

```
SL-hsa-miR-7
                                            (SEQ ID NO: 314)
GTCGTATCCAGTGCAGGGTCCGAGGTATTCGCACTGGATACGAACAACA forward hsa-miR-7
                                            (SEQ ID NO: 315)
GCCCGCTTGGAAGACTAGTGATTTTG SLhsa-miR-26b
                                            (SEQ ID NO: 316)
GTCGTATCCAGTGCAGGGTCCGAGGTATTCGCACTGGATACGACACCTAT forward hsa-miR-26b
                                            (SEQ ID NO: 317)
TGCCAGTTCAAGTAATTCAGGAT SLhsa-miR-26b*
                                            (SEQ ID NO: 318)
GTCGTATCCAGTGCAGGGTCCGAGGTATTCGCACTGGATACGACGAGCCA forward_hsa-miR-26b*
                                            (SEQ ID NO: 319)
TGCCAGCCTGTTCTCCATTACTTG SLhsa-miR-574-5p
                                            (SEQ ID NO: 320)
GTCGTATCCAGTGCAGGGTCCGAGGTATTCGCACTGGATACGACACACAC forward_hsa-miR-574-5p
                                            (SEQ ID NO: 321)
TGCCAGTGAGTGTGTGTGTGAGT SLhsa-miR-574-3p
                                            (SEQ ID NO: 322)
GTCGTATCCAGTGCAGGGTCCGAGGTATTCGCACTGGATACGACTGTGGG forwardhsa-miR-574-3p
                                            (SEQ ID NO: 323)
TGCCAGCACGCTCATGCACACACC SLhsa-miR-27a
                                            (SEQ ID NO: 324)
GTCGTATCCAGTGCAGGGTCCGAGGTATTCGCACTGGATACGACGCGGAA forward hsa-miR-27a
                                            (SEQ ID NO: 325)
TGCCAGTTCACAGTGGCTAAGTT SLhsa-miR-27a*
                                            (SEQ ID NO: 326)
GTCGTATCCAGTGCAGGGTCCGAGGTATTCGCACTGGATACGACTGCTCA forwardhsa-miR-27a*
                                            (SEQ ID NO: 327)
TGCCAGAGGGCTTAGCTGCTTGTG SL hsa-miR-92a-1
                                            (SEQ ID NO: 328)
GTCGTATCCAGTGCAGGGTCCGAGGTATTCGCACTGGATACGAACAGGC forward hsa-miR-92a-1
                                            (SEQ ID NO: 329)
TGCCAGTATTGCACTTGTCCCGGC SLhsa-miR-190b
                                            (SEQ ID NO: 330)
GTCGTATCCAGTGCAGGGTCCGAGGTATTCGCACTGGATACGAAACCCA forward hsa-miR-190b
                                            (SEQ ID NO: 331)
GCCCGCTAAGCCCTTACCCCAAAAA SL_hsa-miR-142-5p
                                            (SEQ ID NO: 332)
GTCGTATCCAGTGCAGGGTCCGAGGTATTCGCACTGGATACGACAGTAGT forward_hsa-miR-142-5p
                                            (SEQ ID NO: 333)
GCCCGCCATAAAGTAGAAAGCAC SL_hsa-miR-142-3p
                                            (SEQ ID NO: 334)
GTCGTATCCAGTGCAGGGTCCGAGGTATTCGCACTGGATACGACTCCATA forward_hsa-miR-142-3p
                                            (SEQ ID NO: 335)
TGCCAGTGTAGTGTTTCCTACTTTA SLhsa-miR-9
                                            (SEQ ID NO: 336)
GTCGTATCCAGTGCAGGGTCCGAGGTATTCGCACTGGATACGACTCATAC forward hsa-miR-9
                                            (SEQ ID NO: 337)
TGCCAGTCTTTGGTTATCTAGCTGT SLhsa-miR-9*
                                            (SEQ ID NO: 338)
GTCGTATCCAGTGCAGGGTCCGAGGTATTCGCACTGGATACGACACTTTC forward_hsa-miR-9*
                                            (SEQ ID NO: 339)
TGCCAGATAAAGCTAGATAACCGA qPCR Reverse
                                            (SEQ ID NO: 340)
GTGCAGGGTCCGAGGT U6 stem loop primer
                                            (SEQ ID NO: 341)
GTCATCCTTGCGCAGG U6 forward primer
                                            (SEQ ID NO: 342)
CGCTTCGGCAGCACATATAC U6 reverse primer
                                            (SEQ ID NO: 343)
AGGGGCCATGCTAATCTTCT
```

For the qPCR 1 μl of RT-PCR product was used in a reaction with 25 pmol forward en reverse primer, $H_2O$ and 2×iQ SYBR Green supermix (Bio-rad, 170-8880). PCR reaction was done on a BioRad CFX96 with a initial 5 minute step of 95° C., 45 cycli of 10 seconds 95° C., 20 seconds 60° C. and 10 seconds 72° C., after which a melting curve analysis was preformed. Relative miRNA expression levels were calculated. CT values for miRNA induced and empty vector samples were obtained and the corresponding U6 CT value was subtracted. The difference between empty vector miRNA levels and miRNA levels in transduced samples were calculated as a measure for over-expression. Calculations ΔCt:
1. The ΔCt=average Ct of miRNA−average Ct of U6 control gene.
2. Calculate ΔΔCt (The ΔΔCt=ΔCt transduced−ΔCt untransduced)

3. These calculations can produce negative or positive numbers.
4. Calculate fold change: If ΔΔCt is negative, there is a fold change increase and the equation is: 2^−[average ΔΔCt] OR if ΔΔCt is positive, there is a fold change decrease and the equation is: −(2^[average ΔΔCt]).

The final hits were reconfirmed by qPCR. HUVECs were transduced with lenti-viral miRNA with a MOI of 50. RNA was isolated and stemloop RT and qPCR was performed. The results are depicted in Table 2.

TABLE 2

Final hits confirmed by qPCR in HUVEC.
Results are depicted in fold increase.

| HUVEC | Fold Increase |
|---|---|
| miR-7 | 248.46 |
| Untransduced miR-7 | 1.00 |
| miR-26b | 7.47 |
| Untransduced miR-26 | 1.00 |
| miR-26b* | 0.00 |
| Untransduced miR-26b* | 1.00 |
| miR-142-5p | 224.64 |

TABLE 2-continued

Final hits confirmed by qPCR in HUVEC.
Results are depicted in fold increase.

| HUVEC | Fold Increase |
|---|---|
| Untransduced miR-142-5p | 1.00 |
| miR-142-3p | 1727.70 |
| Untransduced miR-142-3p | 1.00 |
| miR-574-5p | 48.17 |
| Untransduced miR-574-5p | 1.00 |
| miR-574-3p | 1.60 |
| Untransduced miR-574-3p | 1.00 |
| miR-9 | 1048.5 |
| Untransduced miR-9 | 1.00 |
| miR-9* | 2864.33 |
| Untransduced miR-9* | 1.00 |
| miR-92a-1 | 2.55 |
| Untransduced miR-92a-1 | 1 |
| miR-92a-1 VIAL | 0.90 |
| Untransduced miR-92a-1 | 1 |
| miR-27a | 81.70 |
| Untransduced miR-27a | 1 |
| hsa-miR-27a* | 1.58 |
| Untransduced miR-27a* | 1.00 |
| miR-190b | 694760 |
| Untransduced miR-190b | 1 |

Example 6

DNA Sequence Analysis

The sequence of the cloned miRNAs in the lentiviral vectors for the hits was verified as follows. Proviral DNA was amplified by PCR on the fraction of genomic DNA in the RNA samples, using 1 µl RNA sample as input, and pCDH 15 lentiviral vector-specific primers (forward: 5'-CACGCTGTTTTGACCTCCATAGA-3', reverse: 5'-CACTGACGGGCACCGGAG-3', (SEQ ID NO's: 344, 345)) for 30 cycles at an annealing temperature of 58° C. DNA sequence analysis was performed using 0.1-1 µl of PCR product, 0.5 ul of 10 uM pCDH-specific primer (5'-GACCTCCATAGAAGATTCTAGAGCTAGC-3', (SEQ ID NO: 313)), and the Big Dye v3.1 kit (Applied Biosystems). Products were analyzed on a 3730 DNA Analyzers (Applied Biosystems). Data were collected using the Collection Software v3.0 and analyzed using the Sequencing Analysis v5.3.1 program (Applied Biosystems). This Sanger DNA sequence confirmed the sequence of the miRNA transduced into the cells (Table 3).

TABLE 3

Sanger DNA sequence of lentivirus transduced in HUVEC.

| HUVEC | Accession | ID | Query start | Query end | Subject start | Subject end | Strand | Score | Evalue |
|---|---|---|---|---|---|---|---|---|---|
| hsa-mir-7-3 | MI0000265 | hsa-mir-7-3 | 30 | 139 | 1 | 110 | + | 550 | 5.00E−39 |
| hsa-mir-26b | MI0000084 | hsa-mir-26b | 10 | 86 | 1 | 77 | + | 385 | 2.00E−25 |
| hsa-mir-574 | MI0003581 | hsa-mir-574 | 32 | 127 | 1 | 96 | + | 480 | 3.00E−33 |
| hsa-mir-27a | MI0000085 | hsa-mir-27a | 44 | 120 | 1 | 78 | + | 341 | 1.00E−21 |
| hsa-mir-92a-1 | MI0000093 | hsa-mir-92a-1 | 50 | 127 | 1 | 78 | + | 390 | 8.00E−26 |
| hsa-mir-190b | MI0005545 | hsa-mir-190b | 10 | 88 | 1 | 79 | + | 395 | 3.00E−26 |
| hsa-mir-142 | MI0000458 | hsa-mir-142 | 55 | 141 | 1 | 87 | + | 435 | 2.00E−29 |
| hsa-mir-9-2 | MI0000467 | hsa-mir-9-2 | 5 | 91 | 1 | 87 | + | 435 | 1.00E−29 |

Example 7

Synthetic Mimic Transfection

To validate the selected miRNAs, transfection using a synthetic mimic was performed using X-tremeGENE (Roche,04476093001) according to manufacturers protocol (0.5 µl X-tremeGENE for each 96-well). Mimics (Pre-miR™ miRNA Precursors) and siRNA's (ON-TARGET plus SMARTpool) were ordered from respectively Ambion and Dharmacon and tested at different concentrations. Mimic sequences used are mature sequences of corresponding miRNA molecules as identified in Table 5. Cell viability was determined with the MTS assay as described above.

Materials:
Ambion® Pre-miR™ miRNA Precursors hsa-miR-574-5p (PM13081)
Ambion® Pre-miR™ miRNA Precursors hsa-miR-7 (PM10047)
Ambion® Pre-miR™ miRNA Precursors hsa-miR-190b (PM13035)
Ambion® Pre-miR™ miRNA Precursors hsa-miR-142-3p (PM10398)
Ambion® Pre-miR™ miRNA Precursors hsa-miR-142-5p (PM10979)
Pre-miR™ miRNA Precursor Negative Control #1 (AM17110)
PLK1 ON-TARGETplus SMARTpool (L-003290-00-0005)

Figure 4:
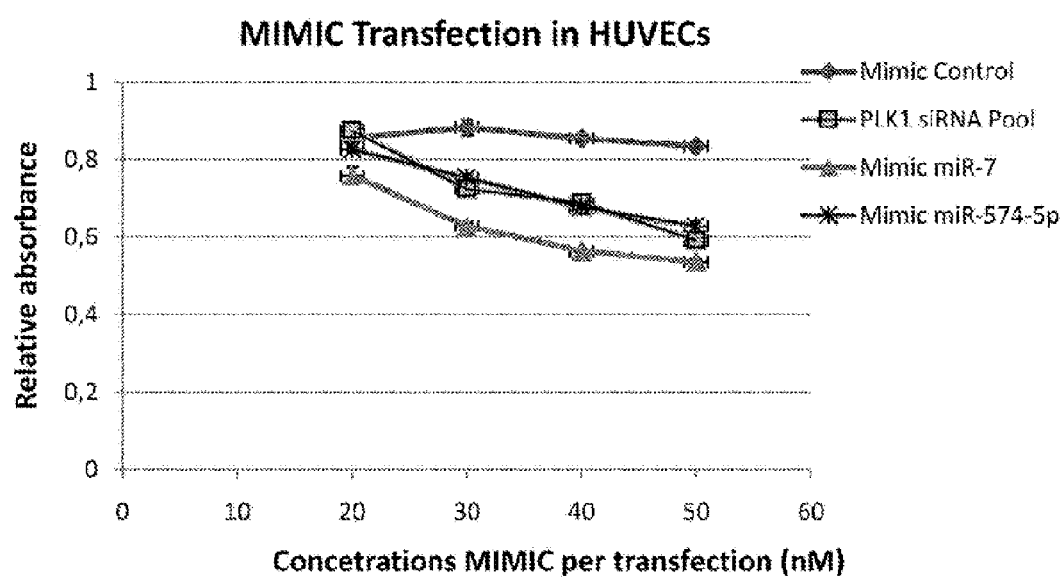
FIG. 4: Transfection in HUVECs with mimics of miRNA-7 (miR-7) and miRNA-574 (miR-574-5p) shows a dose-dependent decrease in cell viability as represented by a decrease in absorbance in the MTS read-out (n=3 per condition; +/−sd). Positive control is siRNA PLK1 (PLK1 is a kinase with anti-proliferation activity). Negative control is indicated by the mimic control, a miRNA with scrambled nucleotide sequence.
Figure 5:
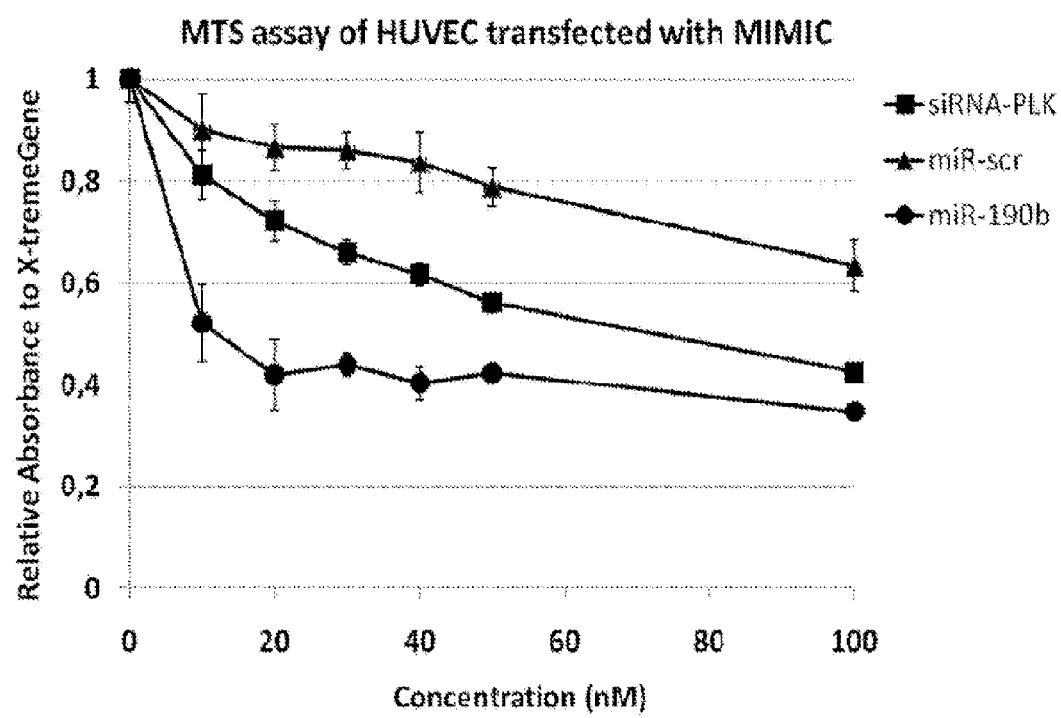
FIG. 5: Transfection in HUVECs with mimics of miRNA-190b (miR-190b) shows a dose-dependent decrease in cell viability as represented by a decrease in absorbance in the MTS read-out (n=3 per condition; +/−sd). Positive control is siRNA PLK1 (PLK1 is a kinase with anti-proliferation activity). Negative control is indicated by the mimic control, a miRNA with scrambled nucleotide sequence.
Figure 6:
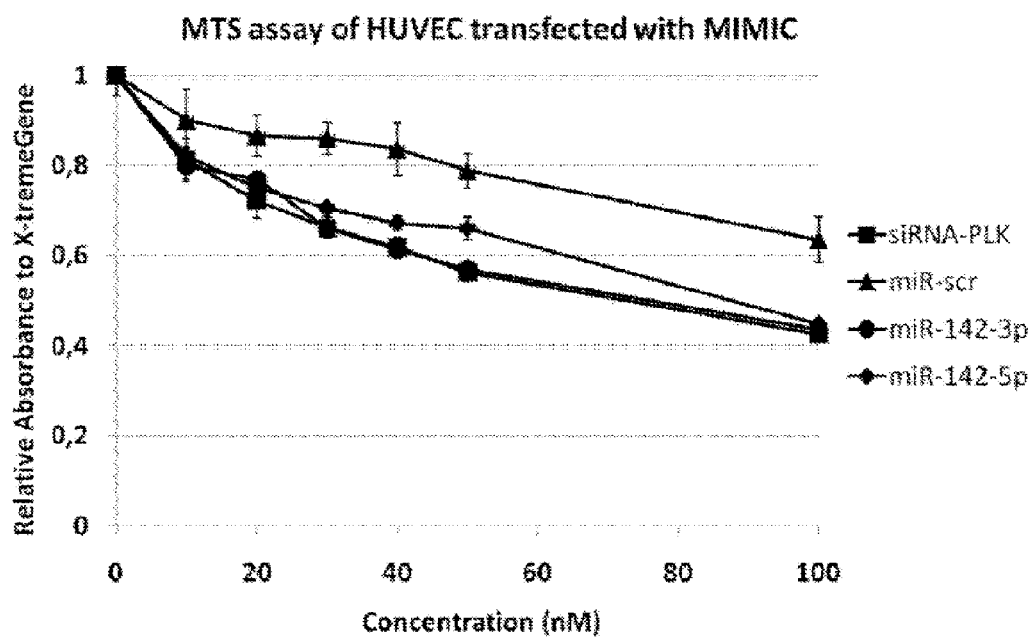
FIG. 6: Transfection in HUVECs with mimics of miRNA-142-3p and miR-142-5p show that miR-142-3p has a stronger dose-dependent decrease in cell viability compared to miR-142-5p as represented by a decrease in absorbance in the MTS read-out (n=3 per condition; +/−sd). Positive control is siRNA PLK1 (PLK1 is a kinase with anti-proliferation activity). Negative control is indicated by the mimic control, a miRNA with scrambled nucleotide sequence.

To further validate the function of the selected miRNAs, a synthetic mimic molecule for miR-7, miR-574-5p, miR-190b, miR-142-3p and miR-142-5p was used. In the same MTS assay, a synthetic mimic as well as a control miRNA and, as a positive control, a PLK1 siRNA was added to HUVEC cells in increasing concentrations (FIGS. 4, 5 and 6). The negative miRNA control showed no effect on cell growth. The siRNA for PLK1 showed an inhibition of cell viability in a dose dependent manner. Similarly, the mimic for miR-7, miR-574-5p, miR-190b, miR-142-3p and miR-142-5p also showed a reduction of cell growth in a dose dependent manner. Furthermore, the results for miR-190b, miR-142-3p and miR-142-5p are depicted in Table 9.

TABLE 9

HUVECs transfected with mimics in a MTS assay depicted in relative absorbance to X-tremeGene. Average relative absorbance ± standard deviation.

| Concentration (nM) | miRNA scrambled | siRNA-PLK | miR-190b | miR-142-3p | miR-142-5p |
|---|---|---|---|---|---|
| 10 | 0.90 ± 0.07 | 0.81 ± 0.05 | 0.52 ± 0.08 | 0.8 ± 0.03 | 0.82 ± 0.02 |
| 30 | 0.86 ± 0.04 | 0.66 ± 0.02 | 0.44 ± 0.02 | 0.66 ± 0.01 | 0.71 ± 0.01 |
| 50 | 0.79 ± 0.04 | 0.56 ± 0.02 | 0.42 ± 0.01 | 0.57 ± 0.01 | 0.66 ± 0.03 |

Example 8

Tube Formation (Matrigel) Assay

Figure 7:
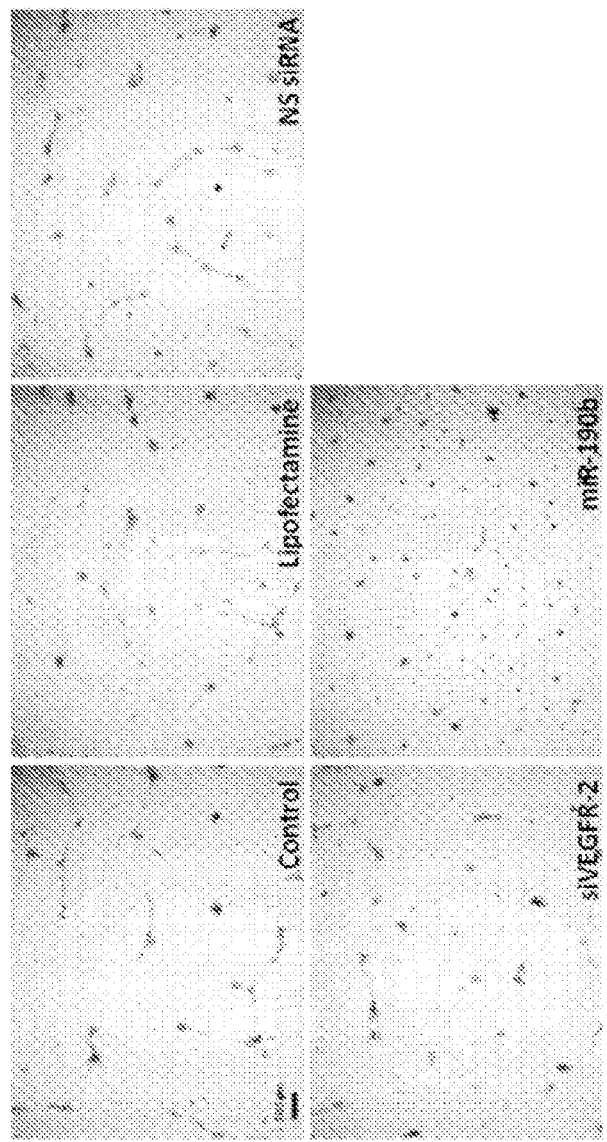
FIG. 7: In vitro endothelial tube formation assays employed Matrigel™ as a three-dimensional extracellular matrix. HUVEC in complete growth medium ($7.5 \times 10^4$) were seeded onto 96-well plates containing Matrigel™ (5 mg/ml). Naive HUVEC seeded in complete growth medium display robust tube formation, as well as cells treated with lipofectamine and scrambled-siRNA. Cells transfected with siRNA-VEGFR2 and miRNA-190b show a markedly abrogated spontaneous tube formation of HUVEC seeded in complete growth medium.
Figure 8:
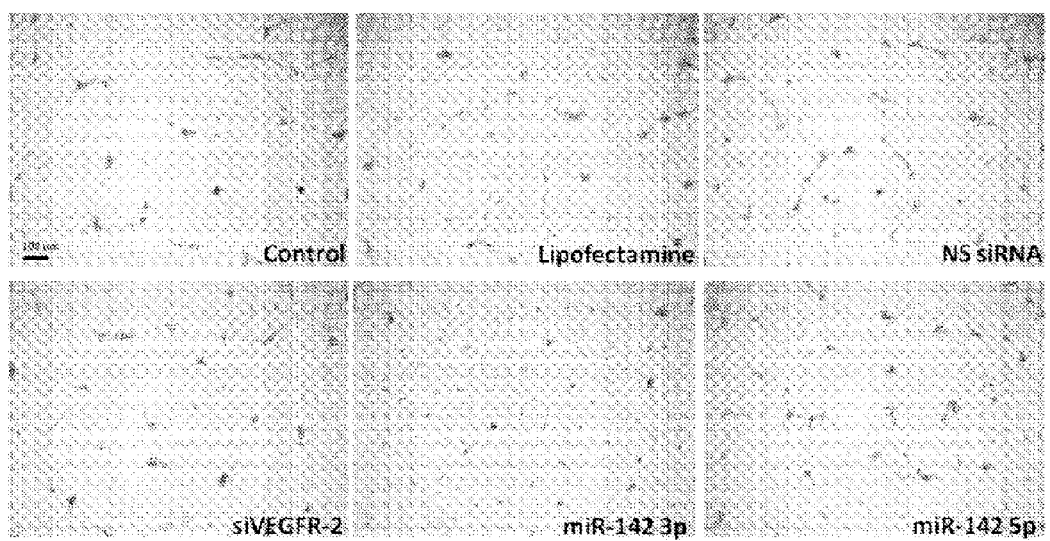
FIG. 8: In vitro endothelial tube formation assays employed Matrigel™ as a three-dimensional extracellular matrix. HUVEC in complete growth medium ($7.5 \times 10^4$) were seeded onto 96-well plates containing Matrigel™ (5 mg/ml). Naive HUVEC seeded in complete growth medium display robust tube formation, as well as cells treated with lipofectamine and scrambled-siRNA. Cells transfected with siRNA-VEGFR2, miR-142-3p show a clearly abrogated spontaneous tube formation of HUVEC seeded in complete growth medium. The inhibition of tube formation after transfection with miR-142-3p shows a much stronger phenotypic effect compared to miR-142-5p.

To confirm the anti-angiogenic effect of miR-190b, miR-142-3p and miR-142-5p, we performed a tube formation assay with HUVECs, since HUVECs form blood vessel-like capillaries on Matrigel. As shown in FIGS. 7 and 8, miR-190b, miR-142-3p and miR-142-5p inhibit the capillary tube formation by HUVECs compared to the control groups, Lipofectamine and scrambled-miRNA.
Materials & Methods:
BD Matrigel Matrix Basement Membrane; BD Bioscience Catalog Number 356237
HUVECs were seeded in a 12 well plate (45000 cells per well) and transfected the day after with XtremeGene and corresponding mimic. Cells were incubated for 48 hours. While the Matrigel coated plate incubates for 30 minutes at 37° C., the transfected HUVECs were counted and prepared in a cell suspension of 7500 cells/100 µl in complete HUVEC growth medium. 100 µl of cell suspension was added to each Matrigel coated well of a 96-well. The plate was incubated in a humidified 37° C. with 5% CO2.
The plates were examined after 3 hours. The cultures were scored at this time for capillary tube formation, and again after 16-20 hours. Data in FIGS. 7 and 8 represent tube formation after 16-20 hours.

Example 9

Tube Formation (Matrigel) Assay with HUVEC Transfected with Synthetic Mimic

To validate the selected miRNAs, transfection using a synthetic mimic was performed using X-tremeGENE (Roche, 04476093001) according to manufacturers protocol (6 µl X-tremeGENE for each 12-well). Mimics (Pre-miR™ miRNA Precursors) and siRNA's (ON-TARGET plus SMARTpool) were ordered from Ambion and Dharmacon, respectively. Mimic sequences used are mature sequences of corresponding miRNA molecules as identified in Table 5.

Figure 9:
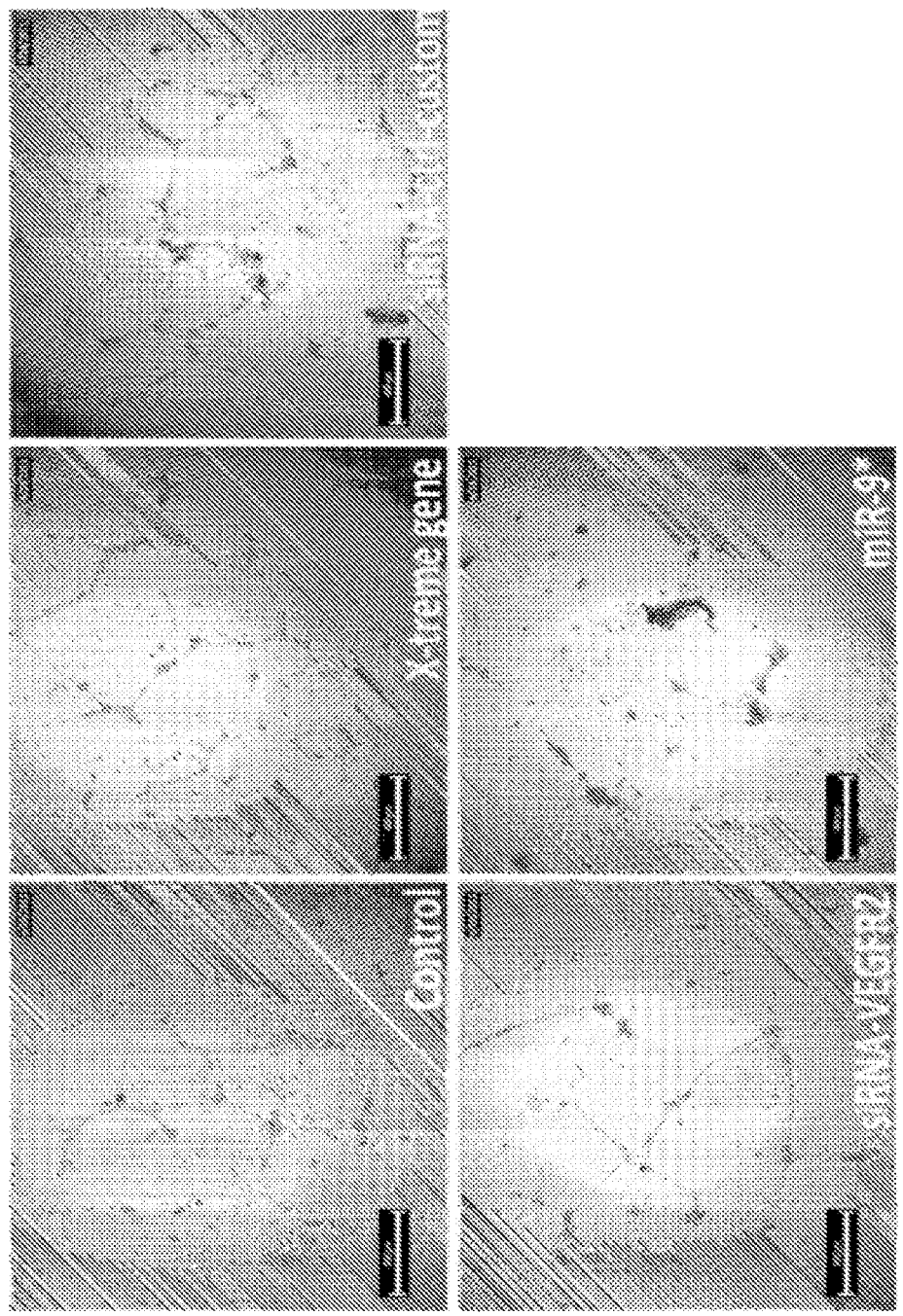
FIG. 9: In vitro endothelial tube formation assays employed Matrigel™ as a three-dimensional extracellular matrix. HUVEC in complete growth medium ($7.5 \times 10^4$) were seeded onto 96-well plates containing Matrigel™ (5 mg/ml). Naive HUVEC seeded in complete growth medium display robust tube formation, as well as cells treated with X-tremeGene and scrambled-siRNA. Cells transfected with miR-9* show a markedly abrogated spontaneous tube formation of HUVEC seeded in complete growth medium compared to cells treated only with X-tremeGene. The abrogation of spontaneous tube formation by miR-9* is stronger than the abrogation of tube formation by siRNA-VEGFR2. Bar is 400 nm.

To confirm the anti-angiogenic effect of a miR-9 such as a miR-9*, we performed a tube formation assay with HUVECs, since they form blood vessel-like capillaries on Matrigel. HUVECs were seeded in a 12 well plate (45000 cells per well) and transfected the day after with X-tremeGene and corresponding MIMIC or siRNA. Cells were incubated for 48 hours.
While the Matrigel coated plate incubates for 30 minutes at 37° C., the transfected HUVECs were counted and prepared in a cell suspension of 7500 cells/100 µl in complete HUVEC growth medium. 100 µl of cell suspension was added to each Matrigel coated well of a 96-well. The plate was incubated in a humidified 37° C. with 5% CO2 and after three hours it was examined. The cultures were scored at this time for capillary tube formation, and again after 16-20 hours.
As shown in FIG. 9, miR-9* strongly inhibits the capillary tube formation by HUVECs compared to the control groups, X-tremeGene and scrambled-siRNA. This assay shows that miR-9* shows a strong inhibition of tube formation.
Materials & Methods:
BD Matrigel Matrix Basement Membrane; BD Bioscience Catalog Number 356237
Ambion® Pre-miR™ miRNA Precursors hsa-miR-9* (PM13072)
Custom made siRNA Negative Control (Ambion)

```
Sense:
                              (SEQ ID NO: 346)
CAUCGUCGAUCGUAGCGCAtt

Antisense:
                              (SEQ ID NO: 347)
UGCGCUACGAUCGACGAUGtt
```

PLK1 ON-TARGETplus SMARTpool (L-003290-00-0005)

Example 10

Synthetic Mimic Transfection

To further confirm the results described in Example 9, showing that miR-9* inhibits tube formation in vitro, a MTS cell viability assay was performed.
Materials and Methods:
HUVECs cultured in EGM-2 medium were transfected with a synthetic mimic using X-tremeGENE (Roche, 04476093001) according to manufacturers protocol (0.5 µl X-tremeGENE for each 96-well). Mimics (Pre-miR™ miRNA Precursors) and siRNA's (ON-TARGET plus SMARTpool) were ordered from respectively Ambion and Dharmacon and tested at different concentrations. Mimic sequences used are mature sequences of corresponding miRNA molecules as identified in Table 5. Cell viability was determined with the MTS assay as described above.

Materials:
Ambion® Pre-miR™ miRNA Precursors hsa-miR-9* (PM13072)
Pre-miR™ miRNA Precursor Negative Control #1 (AM17110)
siRNA scrambled ON-TARGETplus SMARTpool (D-001810-10-05)
PLK1 ON-TARGETplus SMARTpool (L-003290-00-0005)
EGM-2 medium, Lonza (CC-3162)

Figure 10:
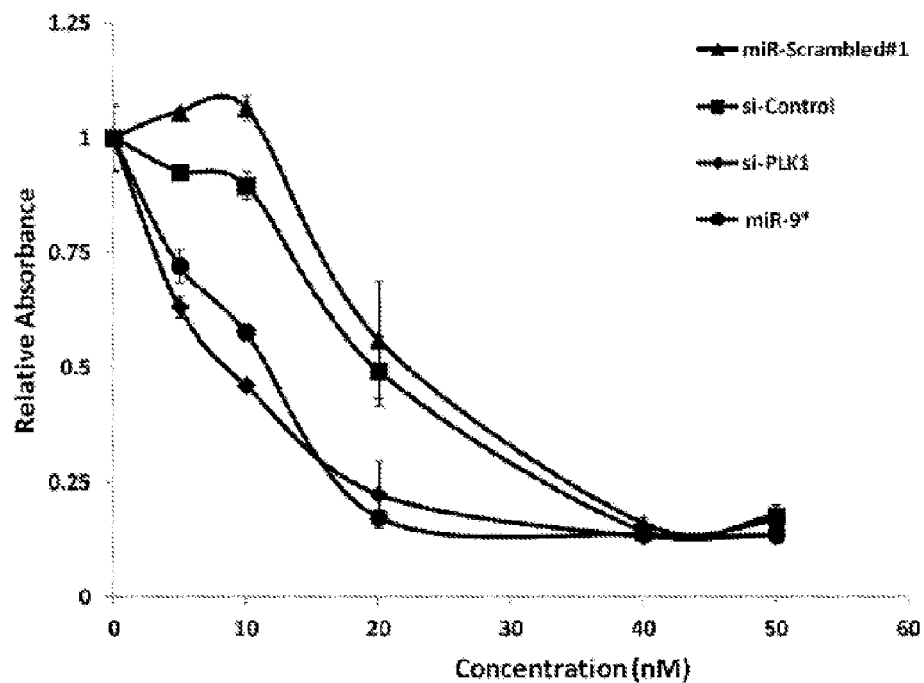
FIG. 10: Transfection in HUVECs with mimics of miRNA-9* (miR-9*) shows a dose-dependent decrease in cell viability as represented by a decrease in absorbance in the MTS read-out (n=3 per condition; +/−sd). Positive control is siRNA PLK1 (PLK1 is a kinase with anti-proliferation activity). Negative control is indicated by the mimic control, a miRNA with scrambled nucleotide sequence (miR-scrambled) and by the siRNA control, a siRNA pool with scrambled nucleotide sequence)

Results:
FIG. 10 shows that the cell viability of HUVEC is dose dependently inhibited by miR-9*. In the same MTS assay, a synthetic mimic, a control miRNA and a positive control, a PLK1 siRNA was added to HUVEC cells in increasing concentrations. The negative miRNA control and siRNA control showed no effect on cell growth up to a concentration of 15 nM. Treatment with siRNA for PLK1 inhibits cell viability in a dose dependent manner. Similarly, treatment with the mimic for miR-9* shows a reduction of cell viability similar to the inhibition of cell viability by siPLK1.

Example 11

In vitro Angiogenesis Assay: Sprouting Assay

The three-dimensional endothelial cell sprouting assay was used as a model to investigate the role of miR-7 and miR-574-5p in endothelial cell proliferation and migration. We transfected HUVEC with mimics and harvested the cells four days after transfection to form spheroids overnight with the hanging drop method. The spheroids were placed in a gel and stimulated with bFGF to actively form capillary sprouts.

Materials and Methods:
HUVEC were transfected with 50 nM of mimics (see Example 7) and were suspended in culture medium containing 20% (v/v) methocel and 10% heat inactivated human serum, at a final density of 40000 cells/ml. The methocel was diluted from a stock solution obtained by dissolving 6 g of carboxymethylcellulose (viscosity 4000 cp; Sigma-Aldrich) in 500 ml of medium 199.

A single spheroid is prepared from 1000 endothelial cells. A drop of 25 µl is pipetted on the inside of the inverted lid of a square 12×12 cm petri-dish. The lid is carefully placed in its normal position over the dish containing 10 ml PBS and placed overnight in an incubator at 37° C. (5% CO2). Drops are pipetted with a multichannel pipette to ensure equal size spheroids and a maximum of 100-120 spheroids are placed on the inside of one dish.

The spheroids were harvested by rinsing the lid gently with 2×5 ml PBS containing 10% heat-inactivated FCS, collected in 15 ml tubes and centrifuged at 300 g for 5 min. Medium is aspirated and the spheroid pellet is gently loosened by scraping over a rough surface.

Collagen gels for embedding of spheroids were prepared from PureCol bovine type I collagen (Nutacon) in medium 199, pH 7.4, by combining, on ice, 2/3 end volume Collagen and 1/12 end volume 10×M199, which is neutralized with ice-cold 0.2M NaOH (solution A). In another tube (B), NBCS (1/10 end volume) and Heparin (0.1% end volume) are mixed with methocell stock (15% of end volume). Subsequently, A and B are gently mixed and used to overlay the spheroids.

HUVEC spheroids were taken up in this complete mix. Then, 400 µl gel was aliquoted into prewarmed µ-slides (Ibidi, Germany) and left to incubate for 30 minutes at 37° C. (5% CO2) for the gels to polymerize. After this step, 100 µl overlay medium containing bFGF (100 ng/ml; 20 ng/ml end concentration) was added for incubation overnight at 37° C. (5% CO2). Approximately 20 spheroids should be present in one well.

Phase-contrast images were captured using a camera (Hitachi GiGE, 1.4 MB) linked to an inverted microscope (Leica DMI3000). In vitro capillary sprouting was quantified by measuring the cumulative sprout length and the number of sprouts per spheroid using ImageJ software. For each treatment group the mean cumulative sprout length and the mean number of sprouts was calculated by averaging these parameters over 10 speroids.

Figure 11A:
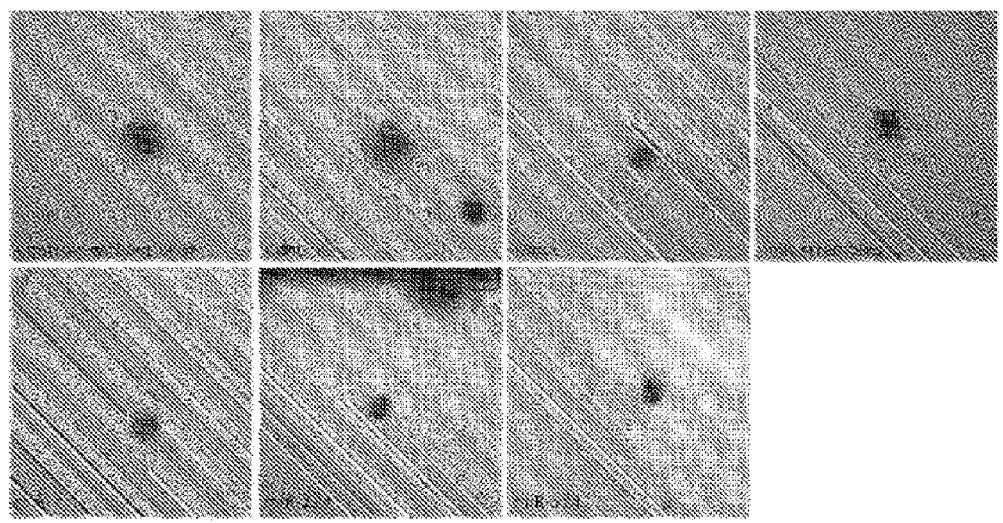
FIG. 11A shows bFGF-induced in-vitro sprouting angiogenesis assay performed with spheroids of HUVEC which are untreated or transfected with a mimic—From left to right and from top to bottom: phase-contrast images of spheroids of untransfected HUVEC; untransfected HUVEC stimulated with bFGF; untransfected HUVEC treated with Xtremegene and bFGF; miR-scrambled transfected HUVEC treated with bFGF; miR-7 HUVEC treated with bFGF; miR-27a transfected HUVEC treated with bFGF; and miR-574-5p transfected HUVEC treated with bFGF.
Figure 11B:
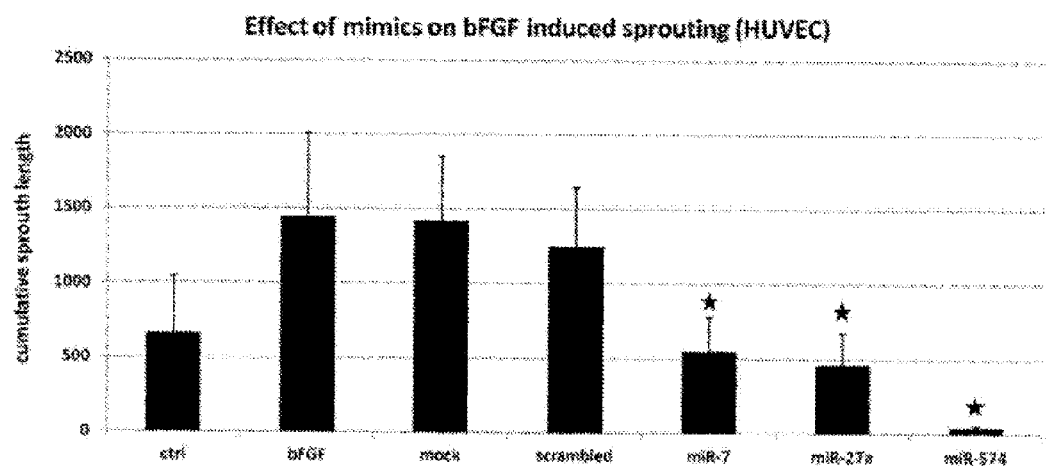
FIG. 11B shows the cumulative sprout length per spheroid from 10 spheroids per treatment group as listed in FIG. 11A.
Figure 11C:
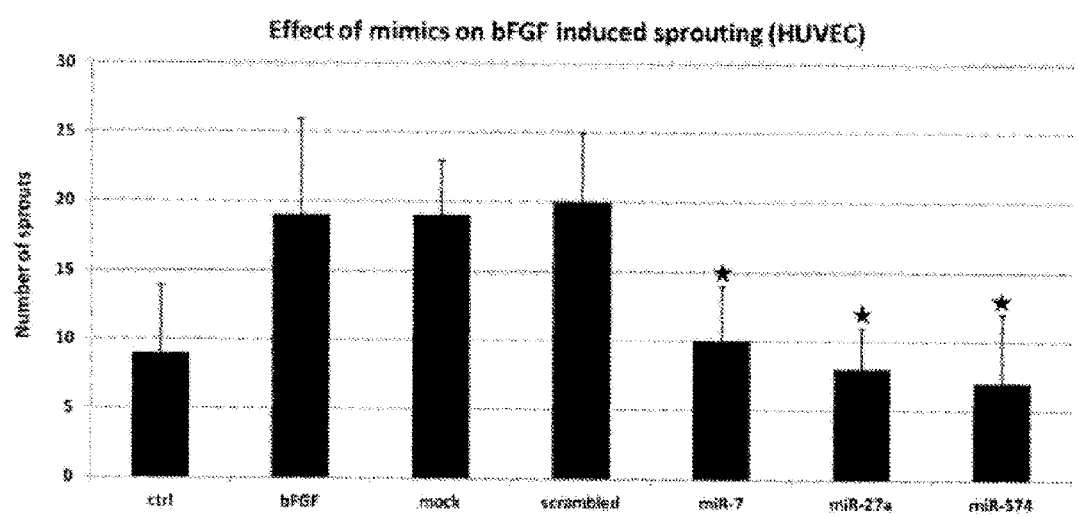
FIG. 11C shows the mean number of sprouts per spheroid from 10 spheroids per treatment group as listed in FIG. 11A. Error bars, SD; (*) $P<0.001$, ANOVA test.

Results:
FIG. 11A shows an example of the images that were used for the quantification of the sprouting properties of HUVEC spheroid. The images show that bFGF induced sprout formation. The images also show that HUVEC spheroids generated from HUVEC that have been treated with miR-7, miR-574-5p and miR-27a form less and short sprouts as compared to the control HUVEC treated with X-tremegene (mock) or miR-scrambled. FIGS. 11B and C depict the quantification of the sprouts per treatment group and shows that miR-7, miR-574-5p and miR-27a significantly inhibit sprout formation and sprout length ($p<0.001$ one-way Anova). miR-27a was used as positive control since this miRNA has been described in literature to be involved in the angiogenesis process.

Example 12

In Vivo Testing of miRNAs in the N2a Tumor Model

Materials and Methods:
To test the efficacy of the anti-proliferative miRNAs in vivo, we used an in-vivo set up adapted from Vader et al. (Angiogenesis. 2011 (4):457-66). Six to eight weeks old normal male A/J mice (Harlan, the Netherlands) were injected subcutaneously with 100 µl Neuro2A cells ($1\times10^7$ cells/ml). Tumor sizes were measured daily with a digital caliper and tumor volume was calculated by using the following formula: Length×width$^2$×0.52. Treatment started with a tumor volume between 40-70 mm$^3$ by intratumoral injection of 10 µg of miRNA or siRNA on days 1, 3, 5, 7, 9, 11 followed by electroporation at a setting of 200V/cm using an ECM 830 electroporator (BTX, San Diego, Calif.) set to deliver 2×2 pulses at perpendicular angles. On day 12 mice were scarified and the tumors were excised. miRNA mimics were ordered from Ambion based on the sequence listed in Table 5. miR-scrambled was ordered from Ambion as described in Example 7. siVEGFR2 was ordered from Ambion and contained the following sequence:

```
Sense:
                                    (SEQ ID NO: 397)
5'-CCGGAAAUCUGGAGAAUCAtt-3'

Anti-sense
                                    (SEQ ID NO: 398)
5'-UGAUUCUCCAGAUUUCCGGtt-3'
```

MiRNAs and siRNA were dissolved in phosphate buffer (PBS).

Figure 12E:
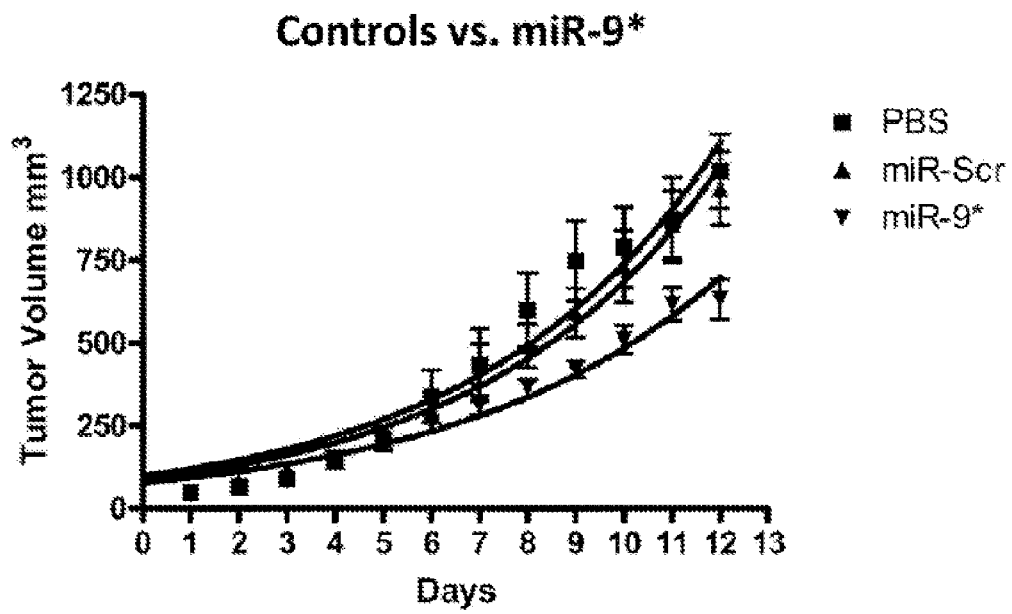

Results:
FIG. 12 shows the tumor growth curves for animal groups that were treated with phosphate buffer (PBS), miR-scrambled, miR-7, miR-574-5p, miR-9*, miR-27a or siVEGFR-2. The curves show that the tumor growth curve of the miR-scrambled (n=6) treated animals is similar to that of PBS treated animals (n=6), indicating low toxicity of non-functional miRNA. The curves also show that animals treated with miR-7 (n=7) show a reduced tumor growth of approximately 50% compared to the miR-Scrambled (n=6) treated group (FIG. 12A). The same effect was observed between day 6 and 10 for mice (n=7) treated with miR-574-5p mimic (FIG. 12B). Strikingly, animals treated with the reference anti-angiogenic miRNA miR-27a (n=7, FIG. 12C), showed less reduction in tumor growth compared to miR-7 and miR-574-5p. As a positive control within the in vivo experiment animals were treated with siVEGFR-2 (n=7, FIG. 12D). This group showed a significant tumor growth repression from day 7 until the end of the experiment compared to PBS (n=6) and miR-Scrambled (n=6) groups. The tumor growth curves in FIG. 12E were generated using a different cohort of mice. Tumors treated with mimic miR-9* (n=8) show a significant tumor growth repression from day 7 until the end of the experiment compared to PBS (n=8) and miR-Scrambled (n=10) treated mice.

Example 13

Immunohistochemistry: CD31 Antibody Staining

To examine whether the inhibition of tumor growth (see Example 12) can be ascribed to a decrease in tumor vasculature, tumors were stained with the endothelial cell marker CD31. Microvascular density (MVD) was calculated by quantification of the CD31 staining.
Materials and Methods:
Paraffin embedded tumor sections of 6 μm were immunostained for CD-31. The paraffin-embedded tumor sections were deparaffinized in xylene and hydrated in a graded series of alcohol baths. After washing the sections in demineralized water, the sections were boiled for 15 min in 10 mM Citrate buffer (pH 6). After reaching room temperature, the sections were washed with 1×PBS followed by incubating them in 5% normal goat serum (Dako x090710) in 1% BSA/PBS for 30 min at RT. Then the tissues were incubated with primary antibody rabbit anti-mouse CD31 in 1% BSA/PBS at 4° C. overnight. Next day after reaching room temperature the tissues were washed 3× with PBS. To inactivate the endogenous peroxidase the tumor tissues were incubated in 0.3% $H_2O_2$/PBS (1 part 30% $H_2O_2$ en 9 parts PBS) for 30 min at RT. After washing 3× with PBS the sections were incubated with Bright Vision polyHRP goat anti-rabbit (Immunologic) for 30 min at RT. The slides were washed again and subsequently incubated in DAB (3,3'-diaminobenzidine) solution (500 μg/ml) for 1 min followed by washing twice with demineralized water. The slides were transferred in Hematoxylin (Mayers, J. T. Baker, the Netherlands) for 15 sec followed by another 2 washing steps with demineralized water and finally with tap water. The slides were dehydrated again by transferring them subsequently into 70%, 90%, 95%, and 100% ethanol and Xylene. The sections were dried followed by addition of 3 drops of Pertex on the slide and covered with cover glass for further analysis.

Figure 13:
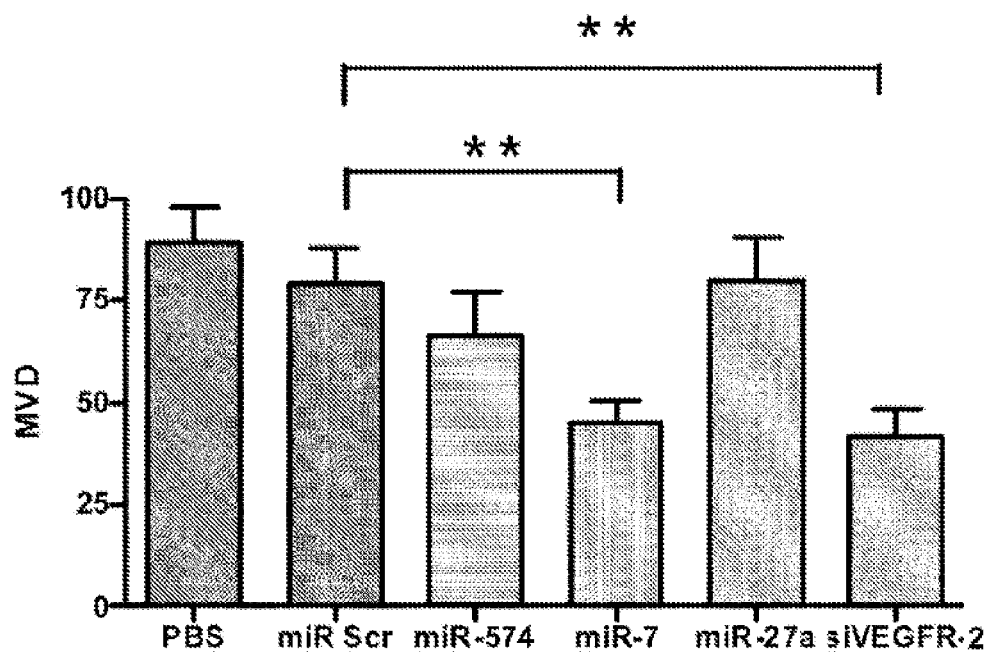
FIG. 13

Quantification of microvessel density (MVD) was done by counting the positively stained luminal structures in four to five representative images per animal Four animals were analysed per treatment group.
Results:
CD31 staining of tumor tissues treated with miR-7 shows a significant reduction in MVD compared to miR-Scrambled treated tumors (FIG. 13). The reduction in MVD is similar to that observed upon treatment with siVEGFR2. This shows that miRNA-7 inhibits microvascularization and acts as an anti-angiogenic miRNA,

TABLE 4

Precursor sequences of miRNAs identified in screening or referred to in the application
List of miRNA precursor sequences (5' to 3' direction). All sequences were obtained from miRBase (release 16: Sept 2010; www.mirbase.org).

| SEQ ID NO | miRNA | Precursor sequence |
|---|---|---|
| 1 | hsa-mir-7-1 | UUGGAUGUUGGCCUAGUUCUGUGUGGAAGACUAGUGAUUUUGUUG UUUUUAGAUAACUAAAUCGACAACAAAUCACAGUCUGCCAUAUGG CACAGGCCAUGCCUCUACAG |
| 2 | hsa-mir-7-2 | CUGGAUACAGAGUGGACCGGCUGGCCCCAUCUGGAAGACUAGUGA UUUUGUUGUUGUCUUACUGCGCUCAACAACAAAUCCCAGUCUACCU AAUGGUGCCAGCCAUCGCA |
| 3 | hsa-mir-7-3 | AGAUUAGAGUGGCUGUGGUCUAGUGCUGUGUGGAAGACUAGUGAU UUUGUUGUUCUGAUGUACUACGACAACAAGUCACAGCCGGCCUCAU AGCGCAGACUCCCUUCGAC |
| 4 | hsa-mir-26b | CCGGGACCCAGUUCAAGUAAUUCAGGAUAGGUUGUGUGCUGUCCA GCCUGUUCUCCAUUACUUGGCUCGGGGACCGG |
| 5 | hsa-mir-574 | GGGACCUGCGUGGGUGCGGGCGUGUGAGUGUGUGUGUGAGUGU GUGUCGCUCCGGGUCCACGCUCAUGCACACACCCACACGCCCACAC UCAGG |
| 6 | hsa-mir-27a | CUGAGGAGCAGGGCUUAGCUGCUUGUGAGCAGGGUCCACACCAAG UCGUGUUCACAGUGGCUAAGUUCCGCCCCCCAG |
| 7 | hsa-mir-92a-1 | CUUUCUACACAGGUUGGGAUCGGUUGCAAUGCUGUGUUUCUGUAU GGUAUUGCACUUGUCCCGGCCUGUUGAGUUUGG |

TABLE 4-continued

Precursor sequences of miRNAs identified in screening or referred to in the application
List of miRNA precursor sequences (5' to 3' direction). All sequences were obtained from miRBase (release 16: Sept 2010; www.mirbase.org).

| SEQ ID NO | miRNA | Precursor sequence |
|---|---|---|
| 8 | hsa-mir-132 | CCGCCCCCGCGUCUCCAGGGCAACCGUGGCUUUCGAUUGUUACUGU GGGAACUGGAGGUAACAGUCUACAGCCAUGGUCGCCCCGCAGCACG CCCACGCGC |
| 9 | hsa-mir-126 | CGCUGGCGACGGGACAUUAUUACUUUUGGUACGCGCUGUGACACU UCAAACUCGUACCGUGAGUAAUAAUGCGCCGUCCACGGCA |
| 10 | hsa-mir-21 | UGUCGGGUAGCUUAUCAGACUGAUGUUGACUGUUGAAUCUCAUGG CAACACCAGUCGAUGGGCUGUCUGACA |
| 11 | hsa-mir-145 | CACCUUGUCCUCACGGUCCAGUUUUCCCAGGAAUCCCUUAGAUGCU AAGAUGGGGAUUCCUGGAAAUACUGUUCUUGAGGUCAUGGUU |
| 12 | hsa-let-7a-1 | UGGGAUGAGGUAGUAGGUUGUAUAGUUUUAGGGUCACACCCACCA CUGGGAGAUAACUAUACAAUCUACUGUCUUUCCUA |
| 13 | hsa-let-7a-2 | AGGUUGAGGUAGUAGGUUGUAUAGUUUAGAAUUACAUCAAGGGAG AUAACUGUACAGCCUCCUAGCUUUCCU |
| 14 | hsa-let-7a-3 | GGGUGAGGUAGUAGGUUGUAUAGUUUGGGGCUCUGCCCUGCUAUG GGAUAACUAUACAAUCUACUGUCUUUCCU |
| 15 | hsa-mir-221 | UGAACAUCCAGGUCUGGGGCAUGAACCUGGCAUACAAUGUAGAUU UCUGUGUUCGUUAGGCAACAGCUACAUUGUCUGCUGGGUUUCAGG CUACCUGGAAACAUGUUCUC |
| 16 | hsa-mir-222 | GCUGCUGGAAGGUGUAGGUACCCUCAAUGGCUCAGUAGCCAGUGU AGAUCCUGUCUUUCGUAAUCAGCAGCUACAUCUGGCUACUGGGUCU CUGAUGGCAUCUUCUAGCU |
| 17 | hsa-mir-190b | UGCUUCUGUGUGAUAUGUUUGAUAUUGGGUUGUUUAAUUAGGAAC CAACUAAAUGUCAAACAUAUUCUUACAGCAGCAG |
| 18 | hsa-mir-142 | GACAGUGCAGUCACCCAUAAAGUAGAAAGCACUACUAACAGCACUG GAGGGUGUAGUGUUUCCUACUUUAUGGAUGAGUGUACUGUG |
| 19 | hsa-mir-9-1 | CGGGGUUGGUUGUUAUCUUUGGUUAUCUAGCUGUAUGAGUGGUGU GGAGUCUUCAUAAAGCUAGAUAACCGAAAGUAAAAAUAACCCCA |
| 20 | hsa-mir-9-2 | GGAAGCGAGUUGUUAUCUUUGGUUAUCUAGCUGUAUGAGUGUAUU GGUCUUCAUAAAGCUAGAUAACCGAAAGUAAAAACUCCUUCA |
| 21 | hsa-mir-9-3 | GGAGGCCCGUUUCUCUCUUUGGUUAUCUAGCUGUAUGAGUGCCAC AGAGCCGUCAUAAAGCUAGAUAACCGAAAGUAGAAAUGAUUCUCA |

TABLE 5

Mature and mimic sequences of miRNAs identified in screening or referred to in the application
List of mature miRNA sequences (5' to 3' direction). All sequences were obtained from miRBase (release 16: Sept 2010; www.mirbase.org).

| microRNA | mature miRNA | Seed (SEQ ID NO) | SEQ mature miRNA (SEQ ID) |
|---|---|---|---|
| hsa-mir-7-1 hsa-mir-7-2 hsa-mir-7-3 | hsa-miR-7 | GGAAGAC (348) | UGGAAGACUAGUGAUUUUGUUGU (22) |
| hsa-mir-7-1 | hsa-miR-7-1* | AACAAAU (349) | CAACAAAUCACAGUCUGCCAUA (23) |
| hsa-mir-7-2 | hsa-miR-7-2* | AACAAAU (350) | CAACAAAUCCCAGUCUACCUAA (24) |
| hsa-mir-26b | hsa-miR-26b | UCAAGUA (351) | UUCAAGUAAUUCAGGAUAGGU (25) |

TABLE 5-continued

Mature and mimic sequences of miRNAs identified in screening or referred to in the application
List of mature miRNA sequences (5' to 3' direction). All sequences were obtained from miRBase (release 16: Sept 2010; www.mirbase.org).

| microRNA | mature miRNA | Seed (SEQ ID NO) | SEQ mature miRNA (SEQ ID) |
|---|---|---|---|
| hsa-mir-26b | hsa-miR-26b* | CUGUUCU (352) | CCUGUUCUCCAUUACUUGGCUC (26) |
| hsa-mir-574 | hsa-miR-574-5p | GAGUGUG (353) | UGAGUGUGUGUGUGUGAGUGUGU (27) |
| hsa-mir-574 | hsa-miR-574-3p | ACGCUCA (354) | CACGCUCAUGCACACACCCACA (28) |
| hsa-mir-27a | hsa-miR-27a | UCACAGU (355) | UUCACAGUGGCUAAGUUCCGC (29) |
| hsa-mir-27a | hsa-miR-27a* | GGGCUUA (356) | AGGGCUUAGCUGCUUGUGAGCA (30) |
| hsa-mir-92a-1 hsa-mir-92a-2 | hsa-miR-92a | AUUGCAC (357) | UAUUGCACUUGUCCCGGCCUGU (31) |
| hsa-mir-92a-1 | hsa-miR-92a-1* | GGUUGGG (358) | AGGUUGGGAUCGGUUGCAAUGCU (32) |
| hsa-mir-132 | hsa-miR-132 | AACAGUC (359) | UAACAGUCUACAGCCAUGGUCG (33) |
| hsa-mir-132 | hsa-miR-132* | CCGUGGC (360) | ACCGUGGCUUUCGAUUGUUACU (34) |
| hsa-mir-126 | hsa-miR-126 | CGUACCG (361) | UCGUACCGUGAGUAAUAAUGCG (35) |
| hsa-mir-126 | hsa-miR-126* | AUUAUUA (362) | CAUUAUUACUUUUGGUACGCG (36) |
| hsa-mir-21 | hsa-miR-21 | AGCUUAU (363) | UAGCUUAUCAGACUGAUGUUGA (37) |
| hsa-mir-21 | hsa-miR-21* | AACACCA (364) | CAACACCAGUCGAUGGGCUGU (38) |
| hsa-mir-145 | hsa-miR-145 | UCCAGUU (365) | GUCCAGUUUUCCCAGGAAUCCCU (39) |
| hsa-mir-145 | hsa-miR-145* | GAUUCCU (366) | GGAUUCCUGGAAAUACUGUUCU (40) |
| hsa-let-7a-1 hsa-let-7a-2 hsa-let-7a-3 | hsa-let-7a | GAGGUAG (367) | UGAGGUAGUAGGUUGUAUAGUU (41) |
| hsa-let-7a-1 hsa-let-7a-3 | hsa-let-7a* | UAUACAA (368) | CUAUACAAUCUACUGUCUUUC (42) |
| hsa-let-7a-2 | hsa-let-7a-2* | UGUACAG (369) | CUGUACAGCCUCCUAGCUUUCC (43) |
| hsa-mir-221 | hsa-miR-221 | GCUACAU (370) | AGCUACAUUGUCUGCUGGGUUUC (44) |
| hsa-mir-221 | hsa-miR-221* | CCUGGCA (371) | ACCUGGCAUACAAUGUAGAUUU (45) |
| hsa-mir-222 | hsa-miR-222 | GCUACAU (372) | AGCUACAUCUGGCUACUGGGU (46) |
| hsa-mir-222 | hsa-miR-222* | UCAGUAG (373) | CUCAGUAGCCAGUGUAGAUCCU (47) |
| hsa-mir-190b | hsa-miR-190b | GAUAUGU (374) | UGAUAUGUUUGAUAUUGGGUU (48) |
| hsa-mir-142 | hsa-miR-142-5p | AUAAAGU (375) | CAUAAAGUAGAAAGCACUACU (49) |
| hsa-mir-142 | hsa-miR-142-3p | GUAGUGU (376) | UGUAGUGUUUCCUACUUUAUGGA (50) |

TABLE 5-continued

Mature and mimic sequences of miRNAs identified in screening or referred to in the application
List of mature miRNA sequences (5' to 3' direction). All sequences were obtained from miRBase (release 16: Sept 2010; www.mirbase.org).

| microRNA | mature miRNA | Seed (SEQ ID NO) | SEQ mature miRNA (SEQ ID) |
|---|---|---|---|
| hsa-mir-9-1<br>hsa-mir-9-2<br>hsa-mir-9-3 | hsa-miR-9 | CUUUGGU (377) | UCUUUGGUUAUCUAGCUGUAUGA (51) |
| hsa-mir-9-1<br>hsa-mir-9-2<br>hsa-mir-9-3 | hsa-miR-9* | UAAAGCU (378) | AUAAAGCUAGAUAACCGAAAGU (52) |

TABLE 6

DNA Sequences of miRNAs identified in screening (see Table 1)

| Seq ID | miRNA | Cloned sequence in lentiviral vector |
|---|---|---|
| 53 | hsa-mir-7-3 | TCATAGCTTGGCTCAGGTGAGAAGGAGGAGCTGGGCAGGGGTCTCAGA<br>CATGGGGCAGAGGGTGGTGAAGAAGATTAGAGTGGCTGTGGTCTAGTG<br>CTGTGTGGAAGACTAGTGATTTTGTTGTTCTGATGTACTACGACAACAA<br>GTCACAGCCGGCCTCATAGCGCAGACTCCCTTCGACCTTCGCCTTCAAT<br>GGGCTGGCCAGTGGGGGAGAACCGGGGAGGTCGGGGAAGAATCGCTT<br>CCACTCGGAGTGGGGGGGCTGGCTCACTCCAGGCGATACAG |
| 54 | hsa-mir-26b | GGGCTCCTCCTCTAGGCTCCCCCGTGCTGTGCTCCCTCGCCCCACCCTG<br>CCCGGGACCCAGTTCAAGTAATTCAGGATAGGTTGTGTGCTGTCCAGC<br>CTGTTCTCCATTACTTGGCTCGGGGACCGGTGCCCTGCAGCCTTGGGGT<br>GAGGGGGCTGCCCCTGGATTCCTGCACTAGGCTGAGGTTGAGGCAGGG<br>GAAGGGATTGGGAATTAGGGACCTC |
| 55 | hsa-mir-574 | TCTGCGTTAGTGAGAAGCAGTGGTCAGGGAGGACCCGGCTCTGGGGTG<br>AGGGTCTGGGGCGGCGCGGCCGAGGGACCTGCGTGGGTGCGGGCGTGT<br>GAGTGTGTGTGTGAGTGTGTGTCGCTCCGGGTCCACGCTCATGCACA<br>CACCCACACGCCCACACTCAGGGTCTGCCCCCTCGGCCTGCGTGAACCT<br>CCGCGGAGCCTGCCTGGATCTCCCAAAGTATCC |
| 56 | hsa-mir-27a | CCTGTCACAAATCACATTGCCAGGGATTTCCAACCGACCCTGAGCTCTG<br>CCACCGAGGATGCTGCCCGGGGACGGGGTGGCAGAGAGGCCCCGAAG<br>CCTGTGCCTGGCCTGAGGAGCAGGGCTTAGCTGCTTGTGAGCAGGGTC<br>CACACCAAGTCGTGTTCACAGTGGCTAAGTTCCGCCCCCCAGGCCCTCA<br>CCTCCTCTGGCCTTGCCGCCTGTCCCCTGCTGCCGCCTGTCTGCCTGCCA<br>TCCTGCTGCCTGGCCTCCCTGGGCTCTGCCTCCCGTGCCTACTGAGCTG<br>AAACACA |
| 57 | hsa-mir-92a-1 | CCAGCTGTGTGATATTCTGCTGTGCAAATCCATGCAAAACTGACTGTGG<br>TAGTGAAAAGTCTGTAGAAAAGTAAGGGAAACTCAAACCCCTTTCTAC<br>ACAGGTTGGGATCGGTTGCAATGCTGTGTTTCTGTATGGTATTGCACTT<br>GTCCCGGCCTGTTGAGTTTGGTGGGGATTGTGACCAGAAGATTTTGAA<br>AATTAAATATTACTGAAGATTTCGACTTCCACT |
| 58 | hsa-mir-190b | TCTTTGCAACTGGAAGGAAGGCAGATGACCCCCAAAGCTCTCCTGCCT<br>GCTTCTGTGTGATATGTTTGATATTGGGTTGTTTAATTAGGAACCAACT<br>AAATGTCAAACATATTCTTACAGCAGCAGGTGATTCAGCACCACCCTCT<br>TTCATACTTCAATCTCTGGGGCTCCTGTCTCTTTTACTGAACCTCTTCTC<br>TCCAGG |
| 59 | hsa-mir-142 | TCTTAGGAAGCCACAAGGAGGGCTGGGGGGCTCTTGGAGCAGGAGTCA<br>GGAGGCCTGGGCAGCCTGAAGAGTACACGCCGACGGACAGACAGACA<br>GTGCAGTCACCCATAAAGTAGAAAGCACTACTAACAGCACTGGAGGGT<br>GTAGTGTTTCCTACTTTATGGATGAGTGTACTGTGGGCTTCGGAGATCA<br>CGCCACTGCTGCCGCCCGCTGCCCGCCACCATCTTCCTCGGCGCTCGGG<br>GACCTCGTGTGACAGGTGA |
| 60 | hsa-mir-9-2 | ATCAGGACCTGGAGTCTGGCAAGAGGAAGACAGAGGCCTGTGTGGGA<br>AGCGAGTTGTTATCTTTGGTTATCTAGCTGTATGAGTGTATTGGTCTTC<br>ATAAAGCTAGATAACCGAAAGTAAAAACTCCTTCAAGATCGCCGGGGA<br>GCGTGTGAGAATGAAAGACTACAGCCG |

TABLE 7

IsomiR and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR-7 | GGAAGAC (61) | UGGAAGACUAGUGAUUUUGUUGUU (116) |
| | GAAGACU (62) | UGGAAGACUAGUGAUUUUGUUG (117) |
| | AAGACUA (63) | UGGAAGACUAGUGAUUUUGU (118) |
| | AGACUAG (64) | UGGAAGACUAGUGAUUUUGUUGUUU (119) |
| | GACUAGU (65) | UGGAAGACUAGUGAUUUUGUU (120) |
| | ACUAGUG (66) | GGAAGACUAGUGAUUUUGUUGUU (121) |
| | CUAGUGA (67) | GGAAGACUAGUGAUUUUGUUGU (122) |
| | UGGAAGA (68) | UGGAAGACUAGUGAUUUUG (123) |
| | GUGGAAG (69) | UGGAAGACUAGUGAUUUUGUUGUUC (124) |
| | | UGGAAGACUAGUGAUUUU (125) |
| | | GAAGACUAGUGAUUUUGUUGUU (126) |
| | | GAAGACUAGUGAUUUUGUUGU (127) |
| | | UGGAAGACUAGUGAUUUUGUUGUUUU (128) |
| | | GGAAGACUAGUGAUUUUGUUGUUU (129) |
| | | GAAGACUAGUGAUUUUGUUGUUG (130) |
| | | AAGACUAGUGAUUUUGUUGUU (131) |
| | | AGACUAGUGAUUUUGUUGUU (132) |
| | | AAGACUAGUGAUUUUGUUGU (133) |
| | | GACUAGUGAUUUUGUUGUUUU (134) |
| | | GACUAGUGAUUUUGUUGUU (135) |
| | | GGAAGACUAGUGAUUUUGUUG (136) |
| | | UGGAAGACUAGUGAUUUUGUUGUUGU (137) |
| | | UGGAAGACUAGUGAUUUUGUUGUUCUG (138) |
| | | UGGAAGACUAGUGAUUUUGUUGUUCUGA (139) |
| | | AGACUAGUGAUUUUGUUGU (140) |
| | | GGAAGACUAGUGAUUUUGUU (141) |
| | | GACUAGUGAUUUUGUUGUUUUA (142) |
| | | GACUAGUGAUUUUGUUGU (143) |
| | | GACUAGUGAUUUUGUUGUUU (144) |
| | | GUGGAAGACUAGUGAUUUUGUU (145) |
| | | GAAGACUAGUGAUUUUGUUGUUU (146) |
| | | GUGGAAGACUAGUGAUUUUGUUGUU (147) |
| | | GACUAGUGAUUUUGUUGUUUU (148) |
| | | AAGACUAGUGAUUUUGUUGUUU (149) |
| | | AACAAAUCACAGUCUGCCAU (150) |
| | | GUGGAAGACUAGUGAUUUUGUUGU (151) |
| | | UGGAAGACUAGUGAUUUUGUUGUUUU (152) |
| | | AAGACUAGUGAUUUUGUUGUUUU (153) |
| | | ACUAGUGAUUUUGUUGUU (154) |
| | | GGAAGACUAGUGAUUUUGUUGUUG (155) |
| | | GAAGACUAGUGAUUUUGUUG (156) |
| | | AAGACUAGUGAUUUUGUUGUUG (157) |
| | | UGUGGAAGACUAGUGAUUUUGUUGU (158) |
| | | UGUGGAAGACUAGUGAUUUUGU (159) |
| | | CUGGAAGACUAGUGAUUUUGUUGU (160) |
| | | GGAAGACUAGUGAUUUUGUUGUUUU (161) |
| | | GGAAGACUAGUGAUUUUGU (162) |
| | | GAAGACUAGUGAUUUUGUUGUUUU (163) |
| | | AGACUAGUGAUUUUGUUG (164) |
| | | AAGACUAGUGAUUUUGUUGUUUU (165) |
| | | AGACUAGUGAUUUUGUUGUUU (166) |
| hsa-miR-7-1* | AACAAAU (70) | AACAAAUCACAGUCUGCCAUA (167) |
| | CAAAUCA (71) | CAACAAAUCACAGUCUGCCAU (168) |
| | ACAAAUC (72) | CAACAAGUCACAGCCGGCCUCA (169) |
| | AACAAGU (73) | CAACAAAUCACAGUCUGCCA (170) |
| | ACAAGUC (74) | AACAAAUCACAGUCUGCCAUAU (171) |
| | | AACAAAUCACAGUCUGCCAU (172) |
| | | CAACAAGUCACAGCCGGCCUCAU (173) |
| | | CAACAAAUCACAGUCUGCCAUAU (174) |
| | | ACAAAUCACAGUCUGCCAUAU (175) |
| | | CAACAAGUCACAGCCGGCCUC (176) |
| | | AACAAGUCACAGCCGGCCUCA (177) |
| hsa-miR-26b | UCAAGUA (75) | UUCAAGUAAUUCAGGAUAGGUU (178) |
| | CAAGUAA (76) | UCAAGUAAUUCAGGAUAGGUU (179) |
| | | UUCAAGUAAUUCAGGAUAGG (180) |

TABLE 7-continued

IsomiR and seed sequences of miRNAs identified in screening
(see Table 1) or referred to in the application.
These isomiR sequences have been derived from small RNA
high-throughput deep sequencing analyses, and were obtained
after combining the data of 87 human tissue samples.

| Mature miRNA | Seed (SEQ ID NO) | IsomiR sequence (SEQ ID NO) |
| --- | --- | --- |
| hsa-miR-574-5p | GAGUGUG (77)<br>AGUGUGU (78)<br>UGAGUGU (79)<br>UGCGUGG (80) | UGAGUGUGUGUGUGAGUGU (181)<br>UGAGUGUGUGUGUGAGUGUGU (182)<br>UGAGUGUGUGUGUGAGUGUG (183)<br>UGAGUGUGUGUGUGAGUGUG (184)<br>UGAGUGUGUGUGUGAGUG (185)<br>UGAGUGUGUGUGUGAGU (186)<br>GAGUGUGUGUGUGAGUGUGU (187)<br>GAGUGUGUGUGUGAGUGU (188)<br>GUGAGUGUGUGUGUGAGUGU (189)<br>GAGUGUGUGUGUGAGUGUGUU (190)<br>GAGUGUGUGUGUGAGUGUG (191)<br>GUGAGUGUGUGUGUGAGUGUGU (192)<br>GAGUGUGUGUGUGAGUGUGUG (193)<br>UGAGUGUGUGUGUGAG (194)<br>CUGCGUGGGUGCGGGCGUG (195)<br>GAGUGUGUGUGUGAGU (196) |
| hsa-miR-574-3p | ACGCUCA (81)<br>CGCUCAU (82)<br>GCUCAUG (83)<br>CACGCUC (84) | CACGCUCAUGCACACACCCAC (197)<br>CACGCUCAUGCACACACCCA (198)<br>ACGCUCAUGCACACACCCACA (199)<br>CACGCUCAUGCACACACCC (200)<br>CACGCUCAUGCACACACCCACAC (201)<br>CACGCUCAUGCACACACC (202)<br>CGCUCAUGCACACACCCACA (203)<br>ACGCUCAUGCACACACCCAC (204)<br>CCACGCUCAUGCACACACCCAC (205) |
| hsa-miR-27a | UCACAGU (85) | UUCACAGUGGCUAAGUUCCG (206)<br>UUCACAGUGGCUAAGUUCC (207)<br>UUCACAGUGGCUAAGUUC (208)<br>UUCACAGUGGCUAAGUU (209) |
| hsa-miR-92a | AUUGCAC (86) | UAUUGCACUUGUCCCGGCCUG (210)<br>UAUUGCACUUGUCCCGGCCU (211) |
| hsa-miR-132 | AACAGUC (87)<br>ACAGUCU (88) | UAACAGUCUACAGCCAUGGUC (212)<br>UAACAGUCUACAGCCAUGGU (213)<br>AACAGUCUACAGCCAUGGUCG (214)<br>UAACAGUCUACAGCCAUGG (215) |
| hsa-miR-126 | GUACCGU (89) | CGUACCGUGAGUAAUAAUGCG (216) |
| hsa-miR-21 | AGCUUAU (90) | UAGCUUAUCAGACUGAUGUUGAC (217)<br>UAGCUUAUCAGACUGAUGUUG (218) |
| hsa-miR-145 | UCCAGUU (91) | GUCCAGUUUUCCCAGGAAUCCC (219)<br>GUCCAGUUUUCCCAGGAAUCC (220)<br>GUCCAGUUUUCCCAGGAAUC (221)<br>GUCCAGUUUUCCCAGGAAU (222) |
| hsa-miR-221 | GCUACAU (92) | AGCUACAUUGUCUGCUGGGUUU (223)<br>AGCUACAUUGUCUGCUGGGUU (224)<br>AGCUACAUUGUCUGCUGGG (225) |
| hsa-miR-222 | GCUACAU (93) | AGCUACAUCUGGCUACUGGGUCU (226)<br>AGCUACAUCUGGCUACUGGGUCUC (227)<br>AGCUACAUCUGGCUACUGGGUCUCU (228)<br>AGCUACAUCUGGCUACUGGG (229)<br>AGCUACAUCUGGCUACUGGGUC (230) |
| Let-7a | GAGGUAG (94) | UGAGGUAGUAGGUUGUAUAGU (231)<br>UGAGGUAGUAGGUUGUAUAG (232)<br>UGAGGUAGUAGGUUGUAUAGUUU (233) |
| hsa-miR-190b | GAUAUGU (95)<br>AUAUGUU (96) | UGAUAUGUUUGAUAUUGGGUUG (234)<br>UGAUAUGUUUGAUAUUGGGUUGU (235)<br>UGAUAUGUUUGAUAUUGGGU (236)<br>GAUAUGUUUGAUAUUGGGUUG (237)<br>UGAUAUGUUUGAUAUUGGG (238)<br>GAUAUGUUUGAUAUUGGGUUGU (239)<br>GAUAUGUUUGAUAUUGGGUU (240) |

TABLE 7-continued

IsomiR and seed sequences of miRNAs identified in screening
(see Table 1) or referred to in the application.
These isomiR sequences have been derived from small RNA
high-throughput deep sequencing analyses, and were obtained
after combining the data of 87 human tissue samples.

| Mature miRNA | Seed (SEQ ID NO) | IsomiR sequence (SEQ ID NO) |
| --- | --- | --- |
| hsa-miR-142-5p | CCAUAAA (97) | CCCAUAAAGUAGAAAGCACUA (241) |
| | AUAAAGU (98) | CCCAUAAAGUAGAAAGCACU (242) |
| | UAAAGUA (99) | CAUAAAGUAGAAAGCACUA (243) |
| | CAUAAAG (100) | CAUAAAGUAGAAAGCACUACUA (244) |
| | AAAGUAG (101) | CCCAUAAAGUAGAAAGCACUAC (245) |
| | CCCAUAA (102) | AUAAAGUAGAAAGCACUACUAA (246) |
| | AGUAGAA (103) | CAUAAAGUAGAAAGCACUAC (247) |
| | AAGUAGA (104) | CAUAAAGUAGAAAGCACUACUAA (248) |
| | | AUAAAGUAGAAAGCACUACUA (249) |
| | | CCCAUAAAGUAGAAAGCAC (250) |
| | | CCCAUAAAGUAGAAAGCA (251) |
| | | CAUAAAGUAGAAAGCACU (252) |
| | | AUAAAGUAGAAAGCACUACU (253) |
| | | UAAAGUAGAAAGCACUACUAA (254) |
| | | CCAUAAAGUAGAAAGCACUA (255) |
| | | CCAUAAAGUAGAAAGCACUAC (256) |
| | | AUAAAGUAGAAAGCACUA (257) |
| | | CCAUAAAGUAGAAAGCACU (258) |
| | | ACCCAUAAAGUAGAAAGCACUA (259) |
| | | UAAAGUAGAAAGCACUACUA (260) |
| | | CCCAUAAAGUAGAAAGCACUACU (261) |
| | | AUAAAGUAGAAAGCACUAC (262) |
| | | ACCCAUAAAGUAGAAAGCACU (263) |
| | | UAAAGUAGAAAGCACUACU (264) |
| | | CAUAAAGUAGAAAGCACUACUAAC (265) |
| | | AAAGUAGAAAGCACUACUAA (266) |
| | | AUAAAGUAGAAAGCACUACUAAC (267) |
| | | AAGUAGAAAGCACUACUA (268) |
| hsa-miR-142-3p | UAGUGUU (105) | GUAGUGUUUCCUACUUUAUGGA (269) |
| | AGUGUUU (106) | UGUAGUGUUUCCUACUUUAUGG (270) |
| | GUGUUUC (107) | GUAGUGUUUCCUACUUUAUGG (271) |
| | GAGUGUA (108) | UGUAGUGUUUCCUACUUUAUG (272) |
| | UGAGUGU (109) | UGUAGUGUUUCCUACUUUAU (273) |
| | UGUAGUG (110) | GUAGUGUUUCCUACUUUAUG (274) |
| | GUAGUGU (111) | UAGUGUUUCCUACUUUAUGGA (275) |
| | | UGUAGUGUUUCCUACUUU (276) |
| | | UGUAGUGUUUCCUACUUUA (277) |
| | | UAGUGUUUCCUACUUUAUGG (278) |
| | | GUAGUGUUUCCUACUUUAUGGAU (279) |
| | | UGAGUGUACUGUGGGCUUCGG (280) |
| | | GUAGUGUUUCCUACUUUAU (281) |
| | | AGUGUUUCCUACUUUAUGGAU (282) |
| | | AGUGUUUCCUACUUUAUGGA (283) |
| | | UGAGUGUACUGUGGGCUUCGGA (284) |
| | | GUGUAGUGUUUCCUACUUUAUG (285) |
| | | AUGAGUGUACUGUGGGCUUCGGA (286) |
| | | UAGUGUUUCCUACUUUAUG (287) |
| | | AGUGUUUCCUACUUUAUGGAUGA (288) |
| | | AGUGUUUCCUACUUUAUGGAUG (289) |
| hsa-miR-9 | CUUUGGU (112) | UCUUUGGUUAUCUAGCUGUAUG (290) |
| | UUUGGUU (379) | UCUUUGGUUAUCUAGCUGUA (291) |
| | UUGGUUA (380) | UCUUUGGUUAUCUAGCUGUAU (292) |
| | UCUUUGG (381) | UCUUUGGUUAUCUAGCUGU (382) |
| | | CUUUGGUUAUCUAGCUGUAUGA (383) |
| | | UCUUUGGUUAUCUAGCUG (384) |
| | | UCUUUGGUUAUCUAGCUGUAUGAG (385) |
| | | CUUUGGUUAUCUAGCUGUAUG (386) |
| | | UUUGGUUAUCUAGCUGUAUGA (387) |
| | | CUUUGGUUAUCUAGCUGUAU (388) |
| | | CUUUGGUUAUCUAGCUGUA (389) |
| | | CUUUGGUUAUCUAGCUGUAUGAG (390) |
| | | AUCUUUGGUUAUCUAGCUGUAUG (391) |
| | | UUUGGUUAUCUAGCUGUAUGAG (392) |
| | | AUCUUUGGUUAUCUAGCUGUAUGA (393) |
| | | CUUUGGUUAUCUAGCUGU (394) |
| | | UCUUUGGUUAUCUAGCUGUAUGAGU (395) |
| | | AUCUUUGGUUAUCUAGCUGUA (396) |

TABLE 7-continued

IsomiR and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR- 9* | UAAAGCU (113)<br>AAAGCUA (114)<br>AAGCUAG (115) | UAAAGCUAGAUAACCGAAAGUA (293)<br>UAAAGCUAGAUAACCGAAAGU (294)<br>UAAAGCUAGAUAACCGAAAGUAA (295)<br>AUAAAGCUAGAUAACCGAAAGUA (296)<br>AUAAAGCUAGAUAACCGAAAG (297)<br>AUAAAGCUAGAUAACCGAAA (298)<br>AUAAAGCUAGAUAACCGAAAGUAA (299)<br>UAAAGCUAGAUAACCGAAAG (300)<br>UAAAGCUAGAUAACCGAAAGUAAA (301)<br>UAAAGCUAGAUAACCGAAA (302)<br>UAAAGCUAGAUAACCGAAAGUAG (303)<br>AAAGCUAGAUAACCGAAAGU (304) |

TABLE 8

Sequences of Anti-miRNAs (5' to 3' direction) based on mature miRNA sequences (5' to 3' direction) obtained from miRBase (release 16: Sept 2010; www.mirbase.org).

| microRNA | mature miRNA | SEQ ID NO | SEQ Anti-miRNA (5'-3') |
|---|---|---|---|
| hsa-mir-132 | hsa-miR-132 | 305 | CGACCAUGGCUGUAGACUGUUA |
| hsa-mir-132 | hsa-miR-132* | 306 | AGUAACAAUCGAAAGCCACGGU |
| hsa-mir-126 | hsa-miR-126 | 307 | CGCAUUAUUACUCACGGUACGA |
| hsa-mir-126 | hsa-miR-126* | 308 | CGCGUACCAAAAGUAAUAAUG |
| hsa-mir-21 | hsa-miR-21 | 309 | UCAACAUCAGUCUGAUAAGCUA |
| hsa-mir-21 | hsa-miR-21* | 310 | ACAGCCCAUCGACUGGUGUUG |

Reference List

Adams R. H. and Alitalo K. Molecular regulation of angiogenesis and lymphangiogenesis. Nat Rev Mol Cell Biol 8(6):464-478, 2007.

Anand S., Majeti B. K., Acevedo L. M., Murphy E. A., Mukthavaram R., Scheppke L., Huang M., Shields D. J., Lindquist J. N., Lapinski P. E., King P. D., Weis S. M. and Cheresh D. A. MicroRNA-132-mediated loss of p120RasGAP activates the endothelium to facilitate pathological angiogenesis. Nat Med 16(8):909-914, 2010.

Aravin, A. & Tuschl, T. Identification and characterization of small RNAs involved in RNA silencing. FEBS Lett 579:5830-40, 2005.

Asahara T., Masuda H., Takahashi T., Kalka C., Pastore C., Silver M., Kearne M., Magner M. and Isner J. M. Bone marrow origin of endothelial progenitor cells responsible for postnatal vasculogenesis in physiological and pathological neovascularization. Circ Res 85(3):221-228, 1999.

Beijnum, J. R., Rousch, M., Castermans, K., van der Linden, E & Griffioen, A W. Isolation of endothelial cells from fresh tissues, Nature Protocols 3(6):1085-1091, 2008.

Berezikov, E., Cuppen, E., and Plasterk, R. H. Approaches to microRNA discovery, Nat Genet. 38 Suppl, S2-7, 2006.

Berezikov, E., Liu, N., Flynt, A. S., Hodges, E., Rooks, M., Hannon, G. J., and Lai, E. C. Evolutionary flux of canonical microRNAs and mirtrons in Drosophila, Nat Genet. 42,:6-9; author reply 9-10, 2010.

Berezikov, E., Robine, N., Samsonova, A., Westholm, J. O., Naqvi, A., Hung, J. H., Okamura, K., Dai, Q., Bortolamiol-Becet, D., Martin, R., Zhao, Y., Zamore, P. D., Hannon, G. J., Marra, M. A., Weng, Z., Perrimon, N., and Lai, E. C. Deep annotation of Drosophila melanogaster microRNAs yields insights into their processing, modification, and emergence, Genome Res 21:203-215, 2011.

Bodles-Brakhop A M, Heller R and Draghia-Akli R. Electroporation for the Delivery of DNA-based Vaccines and Immunotherapeutics: Current Clinical Developments. Molecular Therapy vol. 17 no. 4:585-592, April 2009

Bonnet, E., Wuyts, J., Rouze, P. and Van De, P. e. Y. Evidence that microRNA precursors, unlike other non-coding RNAs, have lower folding free energies than random sequences. Bioinformatics 20:2911-2917, 2004.

Carmeliet P. Angiogenesis in life, disease and medicine. Nature 438(7070):932-936, 2005.

Carmeliet P. Mechanisms of angiogenesis and arteriogenesis. Nat Med 6(4):389-395, 2000.

Carmeliet P. and Jain R. K. Angiogenesis in cancer and other diseases. Nature 407(6801):249-257, 2000.

Chang T. C. and Mendell J. T. microRNAs in vertebrate physiology and human disease. Annu Rev Genomics Hum Genet. 8:215-239, 2007.

Chen C. Z., Li L., Lodish H. F. and Bartel D. P. MicroRNAs modulate hematopoietic lineage differentiation. Science 303(5654):83-86, 2004.

Creighton, C J., Reid, J G. and Gunaratne, P H. Expression profiling of microRNAs by deep sequencing. Briefings in Bioinformatics. VOL 10. NO 5:490-497, 2009.

Daud, A. I., DeConti, R. C., Andrews, S., Urbas, P., Riker, A. I., Sondak, V. K., Munster, P. N., Sullivan, D. M., Ugen, K. E., Messina, J. L. and Heller, R. Phase I Trial of Interleukin-12 Plasmid Electroporation in Patients With Metastatic Melanoma. Journal of clinical oncology 26(36):5896-903, 2008.

Fish J. E., Santoro M. M., Morton S. U., Yu S., Yeh R. F., Wythe J. D., Ivey K. N., Bruneau B. G., Stainier D. Y. and Srivastava D. miR-126 regulates angiogenic signaling and vascular integrity. Dev Cell 15(2):272-284, 2008.

Folkman J. Tumor angiogenesis: therapeutic implications. N Engl J. Med. 285, 21:1182-1186, 1971.

Folkman J. Angiogenesis in cancer, vascular, rheumatoid and other disease. Nat Med 1(1):27-31, 1995.

Folkman J. Angiogenesis: an organizing principle for drug discovery? Nat Rev Drug Discov 6(4):273-286, 2007.

Folkman J. Role of angiogenesis in tumor growth and metastasis. Semin Oncol 29(6 Suppl 16):15-18, 2002.

Griffioen A. W. and Molema G. Angiogenesis: potentials for pharmacologic intervention in the treatment of cancer, cardiovascular diseases, and chronic inflammation. Pharmacol Rev 52(2):237-268, 2000.

Hanahan D. and Folkman J. Patterns and emerging mechanisms of the angiogenic switch during tumorigenesis. Cell 86(3):353-364, 1996.

Harris T. A., Yamakuchi M., Ferlito M., Mendell J. T. and Lowenstein C. J. MicroRNA-126 regulates endothelial expression of vascular cell adhesion molecule 1. Proc Natl Acad Sci USA 105(5):1516-1521, 2008.

Helisch A. and Schaper W. Arteriogenesis: the development and growth of collateral arteries. Microcirculation 10(1): 83-97, 2003.

Heusschen R, van Gink M, Griffioen A W, Thijssen V L. MicroRNAs in the tumor endothelium: novel controls on the angioregulatory switchboard. Biochim Biophys Acta. 1805, 1:87-96, 2010

Hofacker, I. L. Vienna RNA secondary structure server. Nucleic Acids Res 31:3429-31, 2003. Kuehbacher A., Urbich C., Zeiher A. M. and Dimmeler S. Role of Dicer and Drosha for endothelial microRNA expression and angiogenesis. Circ Res 101(1):59-68, 2007.

le Sage C., Nagel R., Egan D. A., Schrier M., Mesman E., Mangiola A., Anile C., Maira G., Mercatelli N., Clafre S. A., Farace M. G. and Agami R. Regulation of the p27 (Kip1) tumor suppressor by miR-221 and miR-222 promotes cancer cell proliferation. EMBO J. 26(15):3699-3708, 2007.

Linsen, S E V., de Wit, E., de Bruijn, E.& Cuppen, E. Small RNA expression and strain specificity in the rat. BMC Genomics 11:249, 2010.

Miki K., Miki A., Matsuoka M., Muramatsu D., Hackett S. F., Campochiaro P. A. Effects of Intraocular Ranibizumab and Bevacizumab in Transgenic Mice Expressing Human Vascular Endothelial Growth Factor. Ophthalmology 116 (9):1748-1754, September 2009.

Obad, S., dos Santos, C. O., Petri, A., Heidenblad, M., Broom, 0., Ruse, C., Fu, C., Lindow, M., Stenvang, M., Straarup, E. M., Frydenlund Hansen, F., Koch, T., Pappin, D., Hannon, G. J., and Kauppinen, S. Silencing of microRNA families by seed-targeting tiny LNAs. Nature Genetics 43,371-378, 2011.

Poliseno L., Tuccoli A., Mariani L., Evangelista M., Citti L., Woods K., Mercatanti A., Hammond S, and Rainaldi G. MicroRNAs modulate the angiogenic properties of HUVECs. Blood 108(9):3068-3071, 2006.

Poy M. N., Eliasson L., Krutzfeldt J., Kuwajima S., Ma X., Macdonald P. E., Pfeffer S., Tuschl T., Rajewsky N., Rorsman P. and Stoffel M. A pancreatic islet-specific microRNA regulates insulin secretion. Nature 432(7014): 226-230, 2004.

Ribatti D., Vacca A. and Presta M. The discovery of angiogenic factors: a historical review. Gen Pharmacol 35(5): 227-231, 2000.

van Rooij E., Sutherland L. B., Qi X., Richardson J. A., Hill J. and Olson E. N. Control of stress-dependent cardiac growth and gene expression by a microRNA. Science 316(5824):575-579, 2007.

Shen et al. Suppression of ocular neovascularization with siRNA targeting VEGF receptor 1. Gene therapy 13:225-234, 2006.

Steffen P., Voss B., Rehmsmeier M., Reeder J., Giegerich R. RNAshapes: an integrated RNA analysis package based on abstract shapes. Bioinformatics, 22:500-503, 2006

Suarez Y., Fernandez-Hernando C., Pober J. S, and Sessa W. C. Dicer dependent microRNAs regulate gene expression and functions in human endothelial cells. Circ Res 100 (8):1164-1173, 2007.

Vader P, van der Meel R, Symons M H, Fens M H, Pieters E, Wilschut K J, Storm G, Jarzabek M, Gallagher W M, Schiffelers R M, Byrne A T. Examining the role of Rac1 in tumor angiogenesis and growth: a clinically relevant RNAi-mediated approach. Angiogenesis. 2011 December; 14(4):457-66, 2011.

Wang S., Aurora A. B., Johnson B. A., Qi X., McAnally J., Hill J. A., Richardson J. A., Bassel-Duby R. and Olson E. N. The endothelial-specific microRNA miR-126 governs vascular integrity and angiogenesis. Dev Cell 15(2):261-271, 2008.

de Wit, E., Linsen, S. E., Cuppen, E., and Berezikov, E. Repertoire and evolution of miRNA genes in four divergent nematode species, Genome Res 19:2064-2074, 2009.

The invention claimed is:

1. A method for preventing, treating, reverting, and/or delaying neo-angiogenesis or a condition or disease associated with neo-angiogenesis in a subject in need thereof by administering to the subject at least one miRNA molecule or a composition comprising said miRNA molecule, wherein said miRNA molecule is selected from the group consisting of:

an miRNA molecule from 6 to 30 nucleotides comprising at least 6 of the nucleotides present in seed sequence SEQ ID NO: 377, 378, 379, 380, 381, 114 or 115 and having at least 70% identity with SEQ ID NO: 51, 52, 290-304, 382-395 or 396 (miRNA-9), an miRNA molecule from 6 to 30 nucleotides comprising at least 6 of the nucleotides present in seed sequence SEQ ID NO: 77-80, 82-84, 353 or 354 and having at least 70% identity with SEQ ID NO: 27, 28, 181-204 or 205 (miRNA-574), an miRNA molecule from 6 to 30 nucleotides comprising at least 6 of the nucleotides present in seed sequence SEQ ID NO: 62-69, 71-73, 74, 348, 349 or 350 and having at least 70% identity with SEQ ID NO: 22, 23, 24, 116-176 or 177 (miRNA-7), an miRNA molecule from 6 to 30 nucleotides comprising at least 6 of the nucleotides present in seed sequence SEQ ID NO: 96 or 374 and having at least 70% identity with SEQ ID NO: 48, 234-239 or 240 (miRNA-190b), an miRNA molecule from 6 to 30 nucleotides comprising at least 6 of the nucleotides present in seed sequence SEQ ID NO: 97, 99-110, 375 or 376 and having at least 70% identity with SEQ ID NO: 49, 50, 241-288 or 289 (miRNA-142), and/or a precursor of said miRNA molecule.

2. A method according to claim 1, wherein the disease or condition associated with neo-angiogenesis is a cancer.

3. A method according to claim 1, comprising administering to the subject a miRNA-9 molecule, an isomiR or a precursor thereof or a composition comprising said miRNA-9, isomiR or precursor thereof according to claim 1, wherein said miRNA-9 is from 6 to 30 nucleotides, comprises at least 6 of the nucleotides present in seed sequence SEQ ID NO: 378, 114 or 115 and has at least 70% identity with SEQ ID NO: 52 or 293-304.

4. A method according to claim 1, further comprising administering to the subject another miRNA molecule, an isomiR or precursor thereof selected from:

a) a miRNA-9, a miRNA-190b, a miRNA-7, a miRNA-574 and/or a miRNA-142 molecule, and/or an isomiR and/or a precursor thereof, and b) optionally at least one of miRNA-27a, an isomiR and/or a precursor thereof.

5. The method according to claim 1, comprising administering to the subject a miRNA-7 molecule, an isomiR or a precursor thereof or a composition comprising said miRNA-7, isomiR or precursor thereof.

* * * * *

SEQUENCE LISTING

<160> NUMBER OF SEQ ID NOS: 398

<210> SEQ ID NO 1
<211> LENGTH: 110
<212> TYPE: RNA
<213> ORGANISM: Artificial
<220> FEATURE:
<223> OTHER INFORMATION: Precursor sequence

<400> SEQUENCE: 1 uggauguug gccuaguucu guguggaaga cuagugauuu uguuguuuuu agauaacuaa    60
aucgacaaca aaucacaguc ugccauaugg cacaggccau gccucuacag    110

<210> SEQ ID NO 2
<211> LENGTH: 110
<212> TYPE: RNA
<213> ORGANISM: Artificial
<220> FEATURE:
<223> OTHER INFORMATION: Precursor sequence

<400> SEQUENCE: 2
cuggauacag aguggaccgg cuggccccau cuggaagacu agugauuuug uuguugucuu    60
acugcgcuca acaacaaauc ccagucuacc uaaugguugcc agccaucgca    110

<210> SEQ ID NO 3
<211> LENGTH: 110
<212> TYPE: RNA
<213> ORGANISM: Artificial
<220> FEATURE:
<223> OTHER INFORMATION: Precursor sequence

<400> SEQUENCE: 3
agauuagagu ggcugugguc uagugcugug uggaagacua gugauuuugu uguucugaug    60
uacuacgaca acaagucaca gccggccuca uagcgcagac ucccuucgac    110

<210> SEQ ID NO 4
<211> LENGTH: 77
<212> TYPE: RNA
<213> ORGANISM: Artificial
<220> FEATURE:
<223> OTHER INFORMATION: Precursor sequence

<400> SEQUENCE: 4
ccgggaccca guucaaguaa uucaggauag guugugugcu guccagccug uucuccauua    60
cuuggcucgg ggaccgg    77

<210> SEQ ID NO 5
<211> LENGTH: 96
<212> TYPE: RNA
<213> ORGANISM: Artificial
<220> FEATURE:
<223> OTHER INFORMATION: Precursor sequence

<400> SEQUENCE: 5
gggaccugcg ugggugcggg cgugugagug uguguguguug agugugugc gcuccgggc    60 cacgcucaug cacacaccca cacgcccaca cucagg    96

<210> SEQ ID NO 6
<211> LENGTH: 78
<212> TYPE: RNA
<213> ORGANISM: Artificial
<220> FEATURE:
<223> OTHER INFORMATION: Precursor sequence

<400> SEQUENCE: 6
cugaggagca gggcuuagcu gcuugugagc agguccaca ccaagucgug uucacagugg    60
cuaaguuccg cccccccag    78

<210> SEQ ID NO 7
<211> LENGTH: 78
<212> TYPE: RNA

```
<213> ORGANISM: Artificial
<220> FEATURE:
<223> OTHER INFORMATION: Precursor sequence

<400> SEQUENCE: 7
cuuucuacac agguugggau cgguugcaau gcuguguuuc uguauggau ugcacuuguc    60 ccggccuguu gaguuugg                                                78

<210> SEQ ID NO 8
<211> LENGTH: 101
<212> TYPE: RNA
<213> ORGANISM: Artificial
<220> FEATURE:
<223> OTHER INFORMATION: Precursor sequence

<400> SEQUENCE: 8
ccgcccccgc gucuccaggg caaccguggc uuucgauugu acuguggga acuggaggua    60 acagucuaca gccauggucg ccccgcagca cgcccacgcg c                      101

<210> SEQ ID NO 9
<211> LENGTH: 85
<212> TYPE: RNA
<213> ORGANISM: Artificial
<220> FEATURE:
<223> OTHER INFORMATION: Precursor sequence

<400> SEQUENCE: 9
cgcuggcgac gggacauuau uacuuuuggu acgcgcugug acacuucaaa cucguaccgu    60
gaguaauaau gcgccgucca cggca                                        85

<210> SEQ ID NO 10
<211> LENGTH: 72
<212> TYPE: RNA
<213> ORGANISM: Artificial
<220> FEATURE:
<223> OTHER INFORMATION: Precursor sequence

<400> SEQUENCE: 10
ugucggguag cuuaucagac ugauguugac uguugaaucu cauggcaaca ccagucgaug    60
ggcugucuga ca                                                      72

<210> SEQ ID NO 11
<211> LENGTH: 88
<212> TYPE: RNA
<213> ORGANISM: Artificial
<220> FEATURE:
<223> OTHER INFORMATION: Precursor sequence

<400> SEQUENCE: 11
caccuugucc ucacggucca guuuucccag gaaucccuua gaugcuaaga uggggauucc    60
uggaaauacu guucuugagg ucaugguu                                     88

<210> SEQ ID NO 12
<211> LENGTH: 80
<212> TYPE: RNA
<213> ORGANISM: Artificial
<220> FEATURE:
<223> OTHER INFORMATION: Precursor sequence

<400> SEQUENCE: 12
ugggaugagg uaguagguug uauaguuuua gggucacacc caccacuggg agauaacuau    60
acaaucuacu gucuuuccua                                              80
```

<210> SEQ ID NO 13
<211> LENGTH: 72
<212> TYPE: RNA
<213> ORGANISM: Artificial
<220> FEATURE:
<223> OTHER INFORMATION: Precursor sequence

<400> SEQUENCE: 13
agguugaggu aguagguugu auaguuuaga auuacaucaa gggagauaac uguacagccu    60
ccuagcuuuc cu                                                        72

<210> SEQ ID NO 14
<211> LENGTH: 74
<212> TYPE: RNA
<213> ORGANISM: Artificial
<220> FEATURE:
<223> OTHER INFORMATION: Precursor sequence

<400> SEQUENCE: 14
gggugaggua guagguugua aguuugggg cucugcccug cuagggaua acuauacaau      60 cuacugucuu uccu                                                      74

<210> SEQ ID NO 15
<211> LENGTH: 110
<212> TYPE: RNA
<213> ORGANISM: Artificial
<220> FEATURE:
<223> OTHER INFORMATION: Precursor sequence

<400> SEQUENCE: 15
ugaacaucca ggucuggggc augaaccugg cauacaaugu agauuucugu guucguuagg    60
caacagcuac auugucugcu ggguuucagg cuaccuggaa acauguucuc               110

<210> SEQ ID NO 16
<211> LENGTH: 110
<212> TYPE: RNA
<213> ORGANISM: Artificial
<220> FEATURE:
<223> OTHER INFORMATION: Precursor sequence

<400> SEQUENCE: 16
gcugcuggaa gguguaggua cccucaaugg cucaguagcc aguguagauc cugucuuucg    60
uaaucagcag cuacaucugg cuacuggguc ucgauggca ucuucuagcu                110

<210> SEQ ID NO 17
<211> LENGTH: 79
<212> TYPE: RNA
<213> ORGANISM: Artificial
<220> FEATURE:
<223> OTHER INFORMATION: Precursor sequence

<400> SEQUENCE: 17
ugcuucugug ugauauguuu gauauugggu uguuuaauua ggaaccaacu aaaugucaaa    60
cauauucuua cagcagcag                                                 79

<210> SEQ ID NO 18
<211> LENGTH: 87
<212> TYPE: RNA
<213> ORGANISM: Artificial
<220> FEATURE:
<223> OTHER INFORMATION: Precursor sequence

```
<400> SEQUENCE: 18
gacagugcag ucacccauaa aguagaaagc acuacuaaca gcacuggagg guguagyguu    60
uccuacuuua uggaugagug uacugug                                       87

<210> SEQ ID NO 19
<211> LENGTH: 89
<212> TYPE: RNA
<213> ORGANISM: Artificial
<220> FEATURE:
<223> OTHER INFORMATION: Precursor sequence

<400> SEQUENCE: 19
cggggugggu uguuaucuuu gguuaucuag cuguaugagu ggugugggagu cuucauaaag    60 cuagauaacc gaaaguaaaa auaacccca                                     89

<210> SEQ ID NO 20
<211> LENGTH: 87
<212> TYPE: RNA
<213> ORGANISM: Artificial
<220> FEATURE:
<223> OTHER INFORMATION: Precursor sequence

<400> SEQUENCE: 20
ggaagcgagu uguuaucuuu gguuaucuag cuguaugagu guauuggucu ucauaaagcu    60
agauaaccga aaguaaaaac uccuuca                                       87

<210> SEQ ID NO 21
<211> LENGTH: 90
<212> TYPE: RNA
<213> ORGANISM: Artificial
<220> FEATURE:
<223> OTHER INFORMATION: Precursor sequence

<400> SEQUENCE: 21
ggaggcccgu uucucucuuu gguuaucuag cuguaugagu gccacagagc cgucauaaag    60
cuagauaacc gaaaguagaa augauucuca                                    90

<210> SEQ ID NO 22
<211> LENGTH: 23
<212> TYPE: RNA
<213> ORGANISM: Artificial
<220> FEATURE:
<223> OTHER INFORMATION: Mature sequence

<400> SEQUENCE: 22
uggaagacua gugauuuugu ugu                                           23

<210> SEQ ID NO 23
<211> LENGTH: 22
<212> TYPE: RNA
<213> ORGANISM: Artificial
<220> FEATURE:
<223> OTHER INFORMATION: Mature sequence

<400> SEQUENCE: 23
caacaaauca cagucugcca ua                                            22

<210> SEQ ID NO 24
<211> LENGTH: 22
<212> TYPE: RNA
<213> ORGANISM: Artificial
<220> FEATURE:
<223> OTHER INFORMATION: Mature sequence
```

```
<400> SEQUENCE: 24
caacaaaucc cagucuaccu aa                                        22

<210> SEQ ID NO 25
<211> LENGTH: 21
<212> TYPE: RNA
<213> ORGANISM: Artificial
<220> FEATURE:
<223> OTHER INFORMATION: Mature sequence

<400> SEQUENCE: 25
uucaaguaau ucaggauagg u                                         21

<210> SEQ ID NO 26
<211> LENGTH: 22
<212> TYPE: RNA
<213> ORGANISM: Artificial
<220> FEATURE:
<223> OTHER INFORMATION: Mature sequence

<400> SEQUENCE: 26
ccuguucucc auuacuuggc uc                                        22

<210> SEQ ID NO 27
<211> LENGTH: 23
<212> TYPE: RNA
<213> ORGANISM: Artificial
<220> FEATURE:
<223> OTHER INFORMATION: Mature sequence

<400> SEQUENCE: 27
ugagugugug ugugagug ugu                                         23

<210> SEQ ID NO 28
<211> LENGTH: 22
<212> TYPE: RNA
<213> ORGANISM: Artificial
<220> FEATURE:
<223> OTHER INFORMATION: Mature sequence

<400> SEQUENCE: 28
cacgcucaug cacacaccca ca                                        22

<210> SEQ ID NO 29
<211> LENGTH: 21
<212> TYPE: RNA
<213> ORGANISM: Artificial
<220> FEATURE:
<223> OTHER INFORMATION: Mature sequence

<400> SEQUENCE: 29
uucacagugg cuaaguuccg c                                         21

<210> SEQ ID NO 30
<211> LENGTH: 22
<212> TYPE: RNA
<213> ORGANISM: Artificial
<220> FEATURE:
<223> OTHER INFORMATION: Mature sequence

<400> SEQUENCE: 30
agggcuuagc ugcuugugag ca                                        22

<210> SEQ ID NO 31
```

```
<211> LENGTH: 22
<212> TYPE: RNA
<213> ORGANISM: Artificial
<220> FEATURE:
<223> OTHER INFORMATION: Mature sequence

<400> SEQUENCE: 31
uauugcacuu gucccggccu gu                                            22

<210> SEQ ID NO 32
<211> LENGTH: 23
<212> TYPE: RNA
<213> ORGANISM: Artificial
<220> FEATURE:
<223> OTHER INFORMATION: Mature sequence

<400> SEQUENCE: 32
agguugggau cgguugcaau gcu                                           23

<210> SEQ ID NO 33
<211> LENGTH: 22
<212> TYPE: RNA
<213> ORGANISM: Artificial
<220> FEATURE:
<223> OTHER INFORMATION: Mature sequence

<400> SEQUENCE: 33
uaacagucua cagccauggu cg                                            22

<210> SEQ ID NO 34
<211> LENGTH: 22
<212> TYPE: RNA
<213> ORGANISM: Artificial
<220> FEATURE:
<223> OTHER INFORMATION: Mature sequence

<400> SEQUENCE: 34
accguggcuu ucgauuguua cu                                            22

<210> SEQ ID NO 35
<211> LENGTH: 22
<212> TYPE: RNA
<213> ORGANISM: Artificial
<220> FEATURE:
<223> OTHER INFORMATION: Mature sequence

<400> SEQUENCE: 35
ucguaccgug aguaauaaug cg                                            22

<210> SEQ ID NO 36
<211> LENGTH: 21
<212> TYPE: RNA
<213> ORGANISM: Artificial
<220> FEATURE:
<223> OTHER INFORMATION: Mature sequence

<400> SEQUENCE: 36
cauuauuacu uuugguacgc g                                             21

<210> SEQ ID NO 37
<211> LENGTH: 22
<212> TYPE: RNA
<213> ORGANISM: Artificial
<220> FEATURE:
<223> OTHER INFORMATION: Mature sequence

<400> SEQUENCE: 37
```
uagcuuauca gacugauguu ga                                          22

<210> SEQ ID NO 38
<211> LENGTH: 21
<212> TYPE: RNA
<213> ORGANISM: Artificial
<220> FEATURE:
<223> OTHER INFORMATION: Mature sequence

<400> SEQUENCE: 38
caacaccagu cgaugggcug u                                           21

<210> SEQ ID NO 39
<211> LENGTH: 23
<212> TYPE: RNA
<213> ORGANISM: Artificial
<220> FEATURE:
<223> OTHER INFORMATION: Mature sequence

<400> SEQUENCE: 39
guccaguuuu cccaggaauc ccu                                         23

<210> SEQ ID NO 40
<211> LENGTH: 22
<212> TYPE: RNA
<213> ORGANISM: Artificial
<220> FEATURE:
<223> OTHER INFORMATION: Mature sequence

<400> SEQUENCE: 40 ggauccugg aaauacuguu cu                                           22

<210> SEQ ID NO 41
<211> LENGTH: 22
<212> TYPE: RNA
<213> ORGANISM: Artificial
<220> FEATURE:
<223> OTHER INFORMATION: Mature sequence

<400> SEQUENCE: 41
ugagguagua gguuguauag uu                                          22

<210> SEQ ID NO 42
<211> LENGTH: 21
<212> TYPE: RNA
<213> ORGANISM: Artificial
<220> FEATURE:
<223> OTHER INFORMATION: Mature sequence

<400> SEQUENCE: 42
cuauacaauc uacugucuuu c                                           21

<210> SEQ ID NO 43
<211> LENGTH: 22
<212> TYPE: RNA
<213> ORGANISM: Artificial
<220> FEATURE:
<223> OTHER INFORMATION: Mature sequence

<400> SEQUENCE: 43
cuguacagcc uccuagcuuu cc                                          22

<210> SEQ ID NO 44
<211> LENGTH: 23
<212> TYPE: RNA

```
<213> ORGANISM: Artificial
<220> FEATURE:
<223> OTHER INFORMATION: Mature sequence

<400> SEQUENCE: 44
agcuacauug ucugcugggu uuc                                          23

<210> SEQ ID NO 45
<211> LENGTH: 22
<212> TYPE: RNA
<213> ORGANISM: Artificial
<220> FEATURE:
<223> OTHER INFORMATION: Mature sequence

<400> SEQUENCE: 45
accuggcaua caauguagau uu                                           22

<210> SEQ ID NO 46
<211> LENGTH: 21
<212> TYPE: RNA
<213> ORGANISM: Artificial
<220> FEATURE:
<223> OTHER INFORMATION: Mature sequence

<400> SEQUENCE: 46
agcuacaucu ggcuacuggg u                                            21

<210> SEQ ID NO 47
<211> LENGTH: 22
<212> TYPE: RNA
<213> ORGANISM: Artificial
<220> FEATURE:
<223> OTHER INFORMATION: Mature sequence

<400> SEQUENCE: 47
cucaguagcc aguguagauc cu                                           22

<210> SEQ ID NO 48
<211> LENGTH: 21
<212> TYPE: RNA
<213> ORGANISM: Artificial
<220> FEATURE:
<223> OTHER INFORMATION: Mature sequence

<400> SEQUENCE: 48
ugauauguuu gauauugggu u                                            21

<210> SEQ ID NO 49
<211> LENGTH: 21
<212> TYPE: RNA
<213> ORGANISM: Artificial
<220> FEATURE:
<223> OTHER INFORMATION: Mature sequence

<400> SEQUENCE: 49
cauaaaguag aaagcacuac u                                            21

<210> SEQ ID NO 50
<211> LENGTH: 23
<212> TYPE: RNA
<213> ORGANISM: Artificial
<220> FEATURE:
<223> OTHER INFORMATION: Mature sequence

<400> SEQUENCE: 50
uguaguguuu ccuacuuuau gga                                          23
```

<210> SEQ ID NO 51
<211> LENGTH: 23
<212> TYPE: RNA
<213> ORGANISM: Artificial
<220> FEATURE:
<223> OTHER INFORMATION: Mature sequence

<400> SEQUENCE: 51
ucuuugguua ucuagcugua uga                                              23

<210> SEQ ID NO 52
<211> LENGTH: 22
<212> TYPE: RNA
<213> ORGANISM: Artificial
<220> FEATURE:
<223> OTHER INFORMATION: Mature sequence

<400> SEQUENCE: 52
auaaagcuag auaaccgaaa gu                                               22

<210> SEQ ID NO 53
<211> LENGTH: 282
<212> TYPE: DNA
<213> ORGANISM: Artificial
<220> FEATURE:
<223> OTHER INFORMATION: Sequence cloned in lentiviral vector

<400> SEQUENCE: 53
tcatagcttg gctcaggtga aaggaggag ctgggcaggg gtctcagaca tggggcagag        60
ggtggtgaag aagattagag tggctgtggt ctagtgctgt gtggaagact agtgattttg      120
ttgttctgat gtactacgac aacaagtcac agccggcctc atagcgcaga ctcccttcga      180
ccttcgcctt caatgggctg gccagtgggg gagaaccggg gaggtcgggg aagaatcgct      240
tccactcgga gtgggggggc tggctcactc caggcgatac ag                         282

<210> SEQ ID NO 54
<211> LENGTH: 219
<212> TYPE: DNA
<213> ORGANISM: Artificial
<220> FEATURE:
<223> OTHER INFORMATION: Sequence cloned in lentiviral vector

<400> SEQUENCE: 54
gggctcctcc tctaggctcc cccgtgctgt gctccctcgc cccaccctgc ccgggaccca       60
gttcaagtaa ttcaggatag gttgtgtgct gtccagcctg ttctccatta cttggctcgg     120
ggaccggtgc cctgcagcct tggggtgagg gggctgcccc tggattcctg cactaggctg     180
aggttgaggc aggggaaggg attgggaatt agggacctc                            219

<210> SEQ ID NO 55
<211> LENGTH: 227
<212> TYPE: DNA
<213> ORGANISM: Artificial
<220> FEATURE:
<223> OTHER INFORMATION: Sequence cloned in lentiviral vector

<400> SEQUENCE: 55
tctgcgttag tgagaagcag tggtcaggga ggacccggct ctggggtgag ggtctggggc       60
ggcgcggccg agggacctgc gtgggtgcgg gcgtgtgagt gtgtgtgtgt gagtgtgtgt     120
cgctccgggt ccacgctcat gcacacaccc acacgcccac actcagggtc tgcccctcg      180

-continued gcctgcgtga acctccgcgg agcctgcctg gatctcccaa agtatcc        227

<210> SEQ ID NO 56
<211> LENGTH: 299
<212> TYPE: DNA
<213> ORGANISM: Artificial
<220> FEATURE:
<223> OTHER INFORMATION: Sequence cloned in lentiviral vector

<400> SEQUENCE: 56
cctgtcacaa atcacattgc cagggatttc caaccgaccc tgagctctgc caccgaggat        60
gctgcccggg gacggggtgg cagagaggcc ccgaagcctg tgcctggcct gaggagcagg       120
gcttagctgc ttgtgagcag ggtccacacc aagtcgtgtt cacagtggct aagttccgcc       180
ccccaggccc tcacctcctc tggccttgcc gcctgtcccc tgctgccgcc tgtctgcctg       240
ccatcctgct gcctggcctc cctgggctct gcctcccgtg cctactgagc tgaaacaca        299

<210> SEQ ID NO 57
<211> LENGTH: 227
<212> TYPE: DNA
<213> ORGANISM: Artificial
<220> FEATURE:
<223> OTHER INFORMATION: Sequence cloned in lentiviral vector

<400> SEQUENCE: 57
ccagctgtgt gatattctgc tgtgcaaatc catgcaaaac tgactgtggt agtgaaaagt        60
ctgtagaaaa gtaagggaaa ctcaaacccc tttctacaca ggttgggatc ggttgcaatg       120
ctgtgtttct gtatggtatt gcacttgtcc cggcctgttg agtttggtgg ggattgtgac       180
cagaagattt tgaaaattaa atattactga agatttcgac ttccact                    227

<210> SEQ ID NO 58
<211> LENGTH: 202
<212> TYPE: DNA
<213> ORGANISM: Artificial
<220> FEATURE:
<223> OTHER INFORMATION: Sequence cloned in lentiviral vector

<400> SEQUENCE: 58
tctttgcaac tggaaggaag gcagatgacc cccaaagctc tcctgcctgc ttctgtgtga        60
tatgtttgat attgggttgt ttaattagga accaactaaa tgtcaaacat attcttacag       120
cagcaggtga ttcagcacca ccctctttca tacttcaatc tctgggctc ctgtctcttt       180
tactgaacct cttctctcca gg                                                202

<210> SEQ ID NO 59
<211> LENGTH: 260
<212> TYPE: DNA
<213> ORGANISM: Artificial
<220> FEATURE:
<223> OTHER INFORMATION: Sequence cloned in lentiviral vector

<400> SEQUENCE: 59
tcttaggaag ccacaaggag ggctgggggg ctcttggagc aggagtcagg aggcctgggc        60
agcctgaaga gtacacgccg acggacagac agacagtgca gtcacccata agtagaaag       120
cactactaac agcactggag ggtgtagtgt ttcctacttt atggatgagt gtactgtggg       180
cttcggagat cacgccactg ctgccgcccg ctgcccgcca ccatcttcct cggcgctcgg       240
ggacctcgtg tgacaggtga                                                   260

-continued

<210> SEQ ID NO 60
<211> LENGTH: 171
<212> TYPE: DNA
<213> ORGANISM: Artificial
<220> FEATURE:
<223> OTHER INFORMATION: Sequence cloned in lentiviral vector

<400> SEQUENCE: 60
atcaggacct ggagtctggc aagaggaaga cagaggcctg tgtgggaagc gagttgttat      60
ctttggttat ctagctgtat gagtgtattg gtcttcataa agctagataa ccgaaagtaa     120
aaactccttc aagatcgccg gggagcgtgt gagaatgaaa gactacagcc g              171

<210> SEQ ID NO 61
<211> LENGTH: 7
<212> TYPE: RNA
<213> ORGANISM: Artificial
<220> FEATURE:
<223> OTHER INFORMATION: Seed sequence

<400> SEQUENCE: 61 ggaagac                                                                 7

<210> SEQ ID NO 62
<211> LENGTH: 7
<212> TYPE: RNA
<213> ORGANISM: Artificial
<220> FEATURE:
<223> OTHER INFORMATION: Seed sequence

<400> SEQUENCE: 62 gaagacu                                                                 7

<210> SEQ ID NO 63
<211> LENGTH: 7
<212> TYPE: RNA
<213> ORGANISM: Artificial
<220> FEATURE:
<223> OTHER INFORMATION: Seed sequence

<400> SEQUENCE: 63 aagacua                                                                 7

<210> SEQ ID NO 64
<211> LENGTH: 7
<212> TYPE: RNA
<213> ORGANISM: Artificial
<220> FEATURE:
<223> OTHER INFORMATION: Seed sequence

<400> SEQUENCE: 64 agacuag                                                                 7

<210> SEQ ID NO 65
<211> LENGTH: 7
<212> TYPE: RNA
<213> ORGANISM: Artificial
<220> FEATURE:
<223> OTHER INFORMATION: Seed sequence

<400> SEQUENCE: 65 gacuagu                                                                 7

<210> SEQ ID NO 66
<211> LENGTH: 7
<212> TYPE: RNA

```
<213> ORGANISM: Artificial
<220> FEATURE:
<223> OTHER INFORMATION: Seed sequence

<400> SEQUENCE: 66 acuagug                                                            7

<210> SEQ ID NO 67
<211> LENGTH: 7
<212> TYPE: RNA
<213> ORGANISM: Artificial
<220> FEATURE:
<223> OTHER INFORMATION: Seed sequence

<400> SEQUENCE: 67 cuaguga                                                            7

<210> SEQ ID NO 68
<211> LENGTH: 7
<212> TYPE: RNA
<213> ORGANISM: Artificial
<220> FEATURE:
<223> OTHER INFORMATION: Seed sequence

<400> SEQUENCE: 68 uggaaga                                                            7

<210> SEQ ID NO 69
<211> LENGTH: 7
<212> TYPE: RNA
<213> ORGANISM: Artificial
<220> FEATURE:
<223> OTHER INFORMATION: Seed sequence

<400> SEQUENCE: 69 guggaag                                                            7

<210> SEQ ID NO 70
<211> LENGTH: 7
<212> TYPE: RNA
<213> ORGANISM: Artificial
<220> FEATURE:
<223> OTHER INFORMATION: Seed sequence

<400> SEQUENCE: 70 aacaaau                                                            7

<210> SEQ ID NO 71
<211> LENGTH: 7
<212> TYPE: RNA
<213> ORGANISM: Artificial
<220> FEATURE:
<223> OTHER INFORMATION: Seed sequence

<400> SEQUENCE: 71 caaauca                                                            7

<210> SEQ ID NO 72
<211> LENGTH: 7
<212> TYPE: RNA
<213> ORGANISM: Artificial
<220> FEATURE:
<223> OTHER INFORMATION: Seed sequence

<400> SEQUENCE: 72 acaaauc                                                            7
```

<210> SEQ ID NO 73
<211> LENGTH: 7
<212> TYPE: RNA
<213> ORGANISM: Artificial
<220> FEATURE:
<223> OTHER INFORMATION: Seed sequence

<400> SEQUENCE: 73 aacaagu                                                                  7

<210> SEQ ID NO 74
<211> LENGTH: 7
<212> TYPE: RNA
<213> ORGANISM: Artificial
<220> FEATURE:
<223> OTHER INFORMATION: Seed sequence

<400> SEQUENCE: 74 acaaguc                                                                  7

<210> SEQ ID NO 75
<211> LENGTH: 7
<212> TYPE: RNA
<213> ORGANISM: Artificial
<220> FEATURE:
<223> OTHER INFORMATION: Seed sequence

<400> SEQUENCE: 75 ucaagua                                                                  7

<210> SEQ ID NO 76
<211> LENGTH: 7
<212> TYPE: RNA
<213> ORGANISM: Artificial
<220> FEATURE:
<223> OTHER INFORMATION: Seed sequence

<400> SEQUENCE: 76 caaguaa                                                                  7

<210> SEQ ID NO 77
<211> LENGTH: 7
<212> TYPE: RNA
<213> ORGANISM: Artificial
<220> FEATURE:
<223> OTHER INFORMATION: Seed sequence

<400> SEQUENCE: 77 gagugug                                                                  7

<210> SEQ ID NO 78
<211> LENGTH: 7
<212> TYPE: RNA
<213> ORGANISM: Artificial
<220> FEATURE:
<223> OTHER INFORMATION: Seed sequence

<400> SEQUENCE: 78 agugugu                                                                  7

<210> SEQ ID NO 79
<211> LENGTH: 7
<212> TYPE: RNA
<213> ORGANISM: Artificial
<220> FEATURE:

<223> OTHER INFORMATION: Seed sequence

<400> SEQUENCE: 79 ugagugu                                                                    7

<210> SEQ ID NO 80
<211> LENGTH: 7
<212> TYPE: RNA
<213> ORGANISM: Artificial
<220> FEATURE:
<223> OTHER INFORMATION: Seed sequence

<400> SEQUENCE: 80 ugcgugg                                                                    7

<210> SEQ ID NO 81
<211> LENGTH: 7
<212> TYPE: RNA
<213> ORGANISM: Artificial
<220> FEATURE:
<223> OTHER INFORMATION: Seed sequence

<400> SEQUENCE: 81 acgcuca                                                                    7

<210> SEQ ID NO 82
<211> LENGTH: 7
<212> TYPE: RNA
<213> ORGANISM: Artificial
<220> FEATURE:
<223> OTHER INFORMATION: Seed sequence

<400> SEQUENCE: 82 cgcucau                                                                    7

<210> SEQ ID NO 83
<211> LENGTH: 7
<212> TYPE: RNA
<213> ORGANISM: Artificial
<220> FEATURE:
<223> OTHER INFORMATION: Seed sequence

<400> SEQUENCE: 83 gcucaug                                                                    7

<210> SEQ ID NO 84
<211> LENGTH: 7
<212> TYPE: RNA
<213> ORGANISM: Artificial
<220> FEATURE:
<223> OTHER INFORMATION: Seed sequence

<400> SEQUENCE: 84 cacgcuc                                                                    7

<210> SEQ ID NO 85
<211> LENGTH: 7
<212> TYPE: RNA
<213> ORGANISM: Artificial
<220> FEATURE:
<223> OTHER INFORMATION: Seed sequence

<400> SEQUENCE: 85 ucacagu                                                                    7

```
<210> SEQ ID NO 86
<211> LENGTH: 7
<212> TYPE: RNA
<213> ORGANISM: Artificial
<220> FEATURE:
<223> OTHER INFORMATION: Seed sequence

<400> SEQUENCE: 86 auugcac                                                                 7

<210> SEQ ID NO 87
<211> LENGTH: 7
<212> TYPE: RNA
<213> ORGANISM: Artificial
<220> FEATURE:
<223> OTHER INFORMATION: Seed sequence

<400> SEQUENCE: 87 aacaguc                                                                 7

<210> SEQ ID NO 88
<211> LENGTH: 7
<212> TYPE: RNA
<213> ORGANISM: Artificial
<220> FEATURE:
<223> OTHER INFORMATION: Seed sequence

<400> SEQUENCE: 88 acagucu                                                                 7

<210> SEQ ID NO 89
<211> LENGTH: 7
<212> TYPE: RNA
<213> ORGANISM: Artificial
<220> FEATURE:
<223> OTHER INFORMATION: Seed sequence

<400> SEQUENCE: 89 guaccgu                                                                 7

<210> SEQ ID NO 90
<211> LENGTH: 7
<212> TYPE: RNA
<213> ORGANISM: Artificial
<220> FEATURE:
<223> OTHER INFORMATION: Seed sequence

<400> SEQUENCE: 90 agcuuau                                                                 7

<210> SEQ ID NO 91
<211> LENGTH: 7
<212> TYPE: RNA
<213> ORGANISM: Artificial
<220> FEATURE:
<223> OTHER INFORMATION: Seed sequence

<400> SEQUENCE: 91 uccaguu                                                                 7

<210> SEQ ID NO 92
<211> LENGTH: 7
<212> TYPE: RNA
<213> ORGANISM: Artificial
<220> FEATURE:
<223> OTHER INFORMATION: Seed sequence
```

```
<400> SEQUENCE: 92 gcuacau                                                                  7

<210> SEQ ID NO 93
<211> LENGTH: 7
<212> TYPE: RNA
<213> ORGANISM: Artificial
<220> FEATURE:
<223> OTHER INFORMATION: Seed sequence

<400> SEQUENCE: 93 gcuacau                                                                  7

<210> SEQ ID NO 94
<211> LENGTH: 7
<212> TYPE: RNA
<213> ORGANISM: Artificial
<220> FEATURE:
<223> OTHER INFORMATION: Seed sequence

<400> SEQUENCE: 94 gagguag                                                                  7

<210> SEQ ID NO 95
<211> LENGTH: 7
<212> TYPE: RNA
<213> ORGANISM: Artificial
<220> FEATURE:
<223> OTHER INFORMATION: Seed sequence

<400> SEQUENCE: 95 gauaugu                                                                  7

<210> SEQ ID NO 96
<211> LENGTH: 7
<212> TYPE: RNA
<213> ORGANISM: Artificial
<220> FEATURE:
<223> OTHER INFORMATION: Seed sequence

<400> SEQUENCE: 96 auauguu                                                                  7

<210> SEQ ID NO 97
<211> LENGTH: 7
<212> TYPE: RNA
<213> ORGANISM: Artificial
<220> FEATURE:
<223> OTHER INFORMATION: Seed sequence

<400> SEQUENCE: 97 ccauaaa                                                                  7

<210> SEQ ID NO 98
<211> LENGTH: 7
<212> TYPE: RNA
<213> ORGANISM: Artificial
<220> FEATURE:
<223> OTHER INFORMATION: Seed sequence

<400> SEQUENCE: 98 auaaagu                                                                  7

<210> SEQ ID NO 99
<211> LENGTH: 7
```

```
<212> TYPE: RNA
<213> ORGANISM: Artificial
<220> FEATURE:
<223> OTHER INFORMATION: Seed sequence

<400> SEQUENCE: 99 uaaagua                                                               7

<210> SEQ ID NO 100
<211> LENGTH: 7
<212> TYPE: RNA
<213> ORGANISM: Artificial
<220> FEATURE:
<223> OTHER INFORMATION: Seed sequence

<400> SEQUENCE: 100 cauaaag                                                               7

<210> SEQ ID NO 101
<211> LENGTH: 7
<212> TYPE: RNA
<213> ORGANISM: Artificial
<220> FEATURE:
<223> OTHER INFORMATION: Seed sequence

<400> SEQUENCE: 101 aaaguag                                                               7

<210> SEQ ID NO 102
<211> LENGTH: 7
<212> TYPE: RNA
<213> ORGANISM: Artificial
<220> FEATURE:
<223> OTHER INFORMATION: Seed sequence

<400> SEQUENCE: 102 cccauaa                                                               7

<210> SEQ ID NO 103
<211> LENGTH: 7
<212> TYPE: RNA
<213> ORGANISM: Artificial
<220> FEATURE:
<223> OTHER INFORMATION: Seed sequence

<400> SEQUENCE: 103 aguagaa                                                               7

<210> SEQ ID NO 104
<211> LENGTH: 7
<212> TYPE: RNA
<213> ORGANISM: Artificial
<220> FEATURE:
<223> OTHER INFORMATION: Seed sequence

<400> SEQUENCE: 104 aaguaga                                                               7

<210> SEQ ID NO 105
<211> LENGTH: 7
<212> TYPE: RNA
<213> ORGANISM: Artificial
<220> FEATURE:
<223> OTHER INFORMATION: Seed sequence
```

```
<400> SEQUENCE: 105 uaguguu                                                              7

<210> SEQ ID NO 106
<211> LENGTH: 7
<212> TYPE: RNA
<213> ORGANISM: Artificial
<220> FEATURE:
<223> OTHER INFORMATION: Seed sequence

<400> SEQUENCE: 106 aguguuu                                                              7

<210> SEQ ID NO 107
<211> LENGTH: 7
<212> TYPE: RNA
<213> ORGANISM: Artificial
<220> FEATURE:
<223> OTHER INFORMATION: Seed sequence

<400> SEQUENCE: 107 guguuuc                                                              7

<210> SEQ ID NO 108
<211> LENGTH: 7
<212> TYPE: RNA
<213> ORGANISM: Artificial
<220> FEATURE:
<223> OTHER INFORMATION: seed sequence

<400> SEQUENCE: 108 gagugua                                                              7

<210> SEQ ID NO 109
<211> LENGTH: 7
<212> TYPE: RNA
<213> ORGANISM: Artificial
<220> FEATURE:
<223> OTHER INFORMATION: Seed sequence

<400> SEQUENCE: 109 ugagugu                                                              7

<210> SEQ ID NO 110
<211> LENGTH: 7
<212> TYPE: RNA
<213> ORGANISM: Artificial
<220> FEATURE:
<223> OTHER INFORMATION: Seed sequence

<400> SEQUENCE: 110 uguagug                                                              7

<210> SEQ ID NO 111
<211> LENGTH: 7
<212> TYPE: RNA
<213> ORGANISM: Artificial
<220> FEATURE:
<223> OTHER INFORMATION: Seed sequence

<400> SEQUENCE: 111 guagugu                                                              7

<210> SEQ ID NO 112
```

```
<211> LENGTH: 7
<212> TYPE: RNA
<213> ORGANISM: Artificial
<220> FEATURE:
<223> OTHER INFORMATION: Seed sequence

<400> SEQUENCE: 112 cuuuggu                                                                    7

<210> SEQ ID NO 113
<211> LENGTH: 7
<212> TYPE: RNA
<213> ORGANISM: Artificial
<220> FEATURE:
<223> OTHER INFORMATION: Seed sequence

<400> SEQUENCE: 113 uaaagcu                                                                    7

<210> SEQ ID NO 114
<211> LENGTH: 7
<212> TYPE: RNA
<213> ORGANISM: Artificial
<220> FEATURE:
<223> OTHER INFORMATION: Seed sequence

<400> SEQUENCE: 114 aaagcua                                                                    7

<210> SEQ ID NO 115
<211> LENGTH: 7
<212> TYPE: RNA
<213> ORGANISM: Artificial
<220> FEATURE:
<223> OTHER INFORMATION: Seed sequence

<400> SEQUENCE: 115 aagcuag                                                                    7

<210> SEQ ID NO 116
<211> LENGTH: 24
<212> TYPE: RNA
<213> ORGANISM: Artificial
<220> FEATURE:
<223> OTHER INFORMATION: IsomiR sequence

<400> SEQUENCE: 116
uggaagacua gugauuuugu uguu                                                 24

<210> SEQ ID NO 117
<211> LENGTH: 22
<212> TYPE: RNA
<213> ORGANISM: Artificial
<220> FEATURE:
<223> OTHER INFORMATION: IsomiR sequence

<400> SEQUENCE: 117
uggaagacua gugauuuugu ug                                                   22

<210> SEQ ID NO 118
<211> LENGTH: 20
<212> TYPE: RNA
<213> ORGANISM: Artificial
<220> FEATURE:
<223> OTHER INFORMATION: IsomiR sequence

<400> SEQUENCE: 118
```
uggaagacua gugauuuugu                                                    20

<210> SEQ ID NO 119
<211> LENGTH: 25
<212> TYPE: RNA
<213> ORGANISM: Artificial
<220> FEATURE:
<223> OTHER INFORMATION: IsomiR sequence

<400> SEQUENCE: 119
uggaagacua gugauuuugu uguuu                                              25

<210> SEQ ID NO 120
<211> LENGTH: 21
<212> TYPE: RNA
<213> ORGANISM: Artificial
<220> FEATURE:
<223> OTHER INFORMATION: IsomiR sequence

<400> SEQUENCE: 120
uggaagacua gugauuuugu u                                                  21

<210> SEQ ID NO 121
<211> LENGTH: 23
<212> TYPE: RNA
<213> ORGANISM: Artificial
<220> FEATURE:
<223> OTHER INFORMATION: IsomiR sequence

<400> SEQUENCE: 121
ggaagacuag ugauuuuguu guu                                                23

<210> SEQ ID NO 122
<211> LENGTH: 22
<212> TYPE: RNA
<213> ORGANISM: Artificial
<220> FEATURE:
<223> OTHER INFORMATION: IsomiR sequence

<400> SEQUENCE: 122
ggaagacuag ugauuuuguu gu                                                 22

<210> SEQ ID NO 123
<211> LENGTH: 19
<212> TYPE: RNA
<213> ORGANISM: Artificial
<220> FEATURE:
<223> OTHER INFORMATION: IsomiR sequence

<400> SEQUENCE: 123
uggaagacua gugauuuug                                                     19

<210> SEQ ID NO 124
<211> LENGTH: 25
<212> TYPE: RNA
<213> ORGANISM: Artificial
<220> FEATURE:
<223> OTHER INFORMATION: IsomiR sequence

<400> SEQUENCE: 124
uggaagacua gugauuuugu uguuc                                              25

<210> SEQ ID NO 125
<211> LENGTH: 18
<212> TYPE: RNA

<213> ORGANISM: Artificial
<220> FEATURE:
<223> OTHER INFORMATION: IsomiR sequence

<400> SEQUENCE: 125
uggaagacua gugauuuu                                                    18

<210> SEQ ID NO 126
<211> LENGTH: 22
<212> TYPE: RNA
<213> ORGANISM: Artificial
<220> FEATURE:
<223> OTHER INFORMATION: IsomiR sequence

<400> SEQUENCE: 126
gaagacuagu gauuuuguug uu                                               22

<210> SEQ ID NO 127
<211> LENGTH: 21
<212> TYPE: RNA
<213> ORGANISM: Artificial
<220> FEATURE:
<223> OTHER INFORMATION: IsomiR sequence

<400> SEQUENCE: 127
gaagacuagu gauuuuguug u                                                21

<210> SEQ ID NO 128
<211> LENGTH: 26
<212> TYPE: RNA
<213> ORGANISM: Artificial
<220> FEATURE:
<223> OTHER INFORMATION: IsomiR sequence

<400> SEQUENCE: 128
uggaagacua gugauuuugu uguuuu                                           26

<210> SEQ ID NO 129
<211> LENGTH: 24
<212> TYPE: RNA
<213> ORGANISM: Artificial
<220> FEATURE:
<223> OTHER INFORMATION: IsomiR sequence

<400> SEQUENCE: 129
ggaagacuag ugauuuuguu guuu                                             24

<210> SEQ ID NO 130
<211> LENGTH: 23
<212> TYPE: RNA
<213> ORGANISM: Artificial
<220> FEATURE:
<223> OTHER INFORMATION: IsomiR sequence

<400> SEQUENCE: 130
gaagacuagu gauuuuguug uug                                              23

<210> SEQ ID NO 131
<211> LENGTH: 21
<212> TYPE: RNA
<213> ORGANISM: Artificial
<220> FEATURE:
<223> OTHER INFORMATION: IsomiR sequence

<400> SEQUENCE: 131
aagacuagug auuuuguugu u                                                21

<210> SEQ ID NO 132
<211> LENGTH: 20
<212> TYPE: RNA
<213> ORGANISM: Artificial
<220> FEATURE:
<223> OTHER INFORMATION: IsomiR sequence

<400> SEQUENCE: 132
agacuaguga uuuguuguu                                              20

<210> SEQ ID NO 133
<211> LENGTH: 20
<212> TYPE: RNA
<213> ORGANISM: Artificial
<220> FEATURE:
<223> OTHER INFORMATION: IsomiR sequence

<400> SEQUENCE: 133
aagacuagug auuuuguugu                                             20

<210> SEQ ID NO 134
<211> LENGTH: 22
<212> TYPE: RNA
<213> ORGANISM: Artificial
<220> FEATURE:
<223> OTHER INFORMATION: IsomiR sequence

<400> SEQUENCE: 134
gacuagugau uuuguuguuu uu                                          22

<210> SEQ ID NO 135
<211> LENGTH: 19
<212> TYPE: RNA
<213> ORGANISM: Artificial
<220> FEATURE:
<223> OTHER INFORMATION: IsomiR sequence

<400> SEQUENCE: 135 gacugugau uuuguuguu                                               19

<210> SEQ ID NO 136
<211> LENGTH: 21
<212> TYPE: RNA
<213> ORGANISM: Artificial
<220> FEATURE:
<223> OTHER INFORMATION: IsomiR sequence

<400> SEQUENCE: 136
ggaagacuag ugauuuuguu g                                           21

<210> SEQ ID NO 137
<211> LENGTH: 26
<212> TYPE: RNA
<213> ORGANISM: Artificial
<220> FEATURE:
<223> OTHER INFORMATION: IsomiR sequence

<400> SEQUENCE: 137
uggaagacua gugauuuugu uguugu                                      26

<210> SEQ ID NO 138
<211> LENGTH: 27
<212> TYPE: RNA
<213> ORGANISM: Artificial
<220> FEATURE:

<223> OTHER INFORMATION: IsomiR sequence

<400> SEQUENCE: 138
uggaagacua gugauuugu uguucug                                          27

<210> SEQ ID NO 139
<211> LENGTH: 28
<212> TYPE: RNA
<213> ORGANISM: Artificial
<220> FEATURE:
<223> OTHER INFORMATION: IsomiR sequence

<400> SEQUENCE: 139
uggaagacua gugauuugu uguucuga                                         28

<210> SEQ ID NO 140
<211> LENGTH: 19
<212> TYPE: RNA
<213> ORGANISM: Artificial
<220> FEATURE:
<223> OTHER INFORMATION: IsomiR sequence

<400> SEQUENCE: 140
agacuaguga uuuguugu                                                   19

<210> SEQ ID NO 141
<211> LENGTH: 20
<212> TYPE: RNA
<213> ORGANISM: Artificial
<220> FEATURE:
<223> OTHER INFORMATION: IsomiR sequence

<400> SEQUENCE: 141
ggaagacuag ugauuuguu                                                  20

<210> SEQ ID NO 142
<211> LENGTH: 23
<212> TYPE: RNA
<213> ORGANISM: Artificial
<220> FEATURE:
<223> OTHER INFORMATION: IsomiR sequence

<400> SEQUENCE: 142
gacuagugau uuguuguuu uua                                              23

<210> SEQ ID NO 143
<211> LENGTH: 18
<212> TYPE: RNA
<213> ORGANISM: Artificial
<220> FEATURE:
<223> OTHER INFORMATION: IsomiR sequence

<400> SEQUENCE: 143
gacuagugau uuguugu                                                    18

<210> SEQ ID NO 144
<211> LENGTH: 20
<212> TYPE: RNA
<213> ORGANISM: Artificial
<220> FEATURE:
<223> OTHER INFORMATION: IsomiR sequence

<400> SEQUENCE: 144
gacuagugau uuguuguuu                                                  20

```
<210> SEQ ID NO 145
<211> LENGTH: 22
<212> TYPE: RNA
<213> ORGANISM: Artificial
<220> FEATURE:
<223> OTHER INFORMATION: IsomiR sequence

<400> SEQUENCE: 145
guggaagacu agugauuuug uu                                              22

<210> SEQ ID NO 146
<211> LENGTH: 23
<212> TYPE: RNA
<213> ORGANISM: Artificial
<220> FEATURE:
<223> OTHER INFORMATION: IsomiR sequence

<400> SEQUENCE: 146
gaagacuagu gauuuuguug uuu                                             23

<210> SEQ ID NO 147
<211> LENGTH: 25
<212> TYPE: RNA
<213> ORGANISM: Artificial
<220> FEATURE:
<223> OTHER INFORMATION: IsomiR sequence

<400> SEQUENCE: 147
guggaagacu agugauuuug uuguu                                           25

<210> SEQ ID NO 148
<211> LENGTH: 21
<212> TYPE: RNA
<213> ORGANISM: Artificial
<220> FEATURE:
<223> OTHER INFORMATION: IsomiR sequence

<400> SEQUENCE: 148
gacuagugau uuuguuguuu u                                               21

<210> SEQ ID NO 149
<211> LENGTH: 22
<212> TYPE: RNA
<213> ORGANISM: Artificial
<220> FEATURE:
<223> OTHER INFORMATION: IsomiR sequence

<400> SEQUENCE: 149
aagacuagug auuuuguugu uu                                              22

<210> SEQ ID NO 150
<211> LENGTH: 20
<212> TYPE: RNA
<213> ORGANISM: Artificial
<220> FEATURE:
<223> OTHER INFORMATION: IsomiR sequence

<400> SEQUENCE: 150
aacaaaucac agucugccau                                                 20

<210> SEQ ID NO 151
<211> LENGTH: 24
<212> TYPE: RNA
<213> ORGANISM: Artificial
<220> FEATURE:
<223> OTHER INFORMATION: IsomiR sequence
```

```
<400> SEQUENCE: 151
guggaagacu agugauuuug uugu                                    24

<210> SEQ ID NO 152
<211> LENGTH: 27
<212> TYPE: RNA
<213> ORGANISM: Artificial
<220> FEATURE:
<223> OTHER INFORMATION: IsomiR sequence

<400> SEQUENCE: 152
uggaagacua gugauuuugu uguuuuu                                 27

<210> SEQ ID NO 153
<211> LENGTH: 23
<212> TYPE: RNA
<213> ORGANISM: Artificial
<220> FEATURE:
<223> OTHER INFORMATION: IsomiR sequence

<400> SEQUENCE: 153
aagacuagug auuuuguugu uuu                                     23

<210> SEQ ID NO 154
<211> LENGTH: 18
<212> TYPE: RNA
<213> ORGANISM: Artificial
<220> FEATURE:
<223> OTHER INFORMATION: IsomiR sequence

<400> SEQUENCE: 154
acuagugauu uuguuguu                                           18

<210> SEQ ID NO 155
<211> LENGTH: 24
<212> TYPE: RNA
<213> ORGANISM: Artificial
<220> FEATURE:
<223> OTHER INFORMATION: IsomiR sequence

<400> SEQUENCE: 155
ggaagacuag ugauuuuguu guug                                    24

<210> SEQ ID NO 156
<211> LENGTH: 20
<212> TYPE: RNA
<213> ORGANISM: Artificial
<220> FEATURE:
<223> OTHER INFORMATION: IsomiR sequence

<400> SEQUENCE: 156 gaaagacuagu gauuuuguug                                        20

<210> SEQ ID NO 157
<211> LENGTH: 22
<212> TYPE: RNA
<213> ORGANISM: Artificial
<220> FEATURE:
<223> OTHER INFORMATION: IsomiR sequence

<400> SEQUENCE: 157
aagacuagug auuuuguugu ug                                      22

<210> SEQ ID NO 158
<211> LENGTH: 25
```

```
<212> TYPE: RNA
<213> ORGANISM: Artificial
<220> FEATURE:
<223> OTHER INFORMATION: IsomiR sequence

<400> SEQUENCE: 158
uguggaagac uagugauuuu guugu                                          25

<210> SEQ ID NO 159
<211> LENGTH: 22
<212> TYPE: RNA
<213> ORGANISM: Artificial
<220> FEATURE:
<223> OTHER INFORMATION: IsomiR sequence

<400> SEQUENCE: 159
uguggaagac uagugauuuu gu                                             22

<210> SEQ ID NO 160
<211> LENGTH: 24
<212> TYPE: RNA
<213> ORGANISM: Artificial
<220> FEATURE:
<223> OTHER INFORMATION: IsomiR sequence

<400> SEQUENCE: 160
cuggaagacu agugauuuug uugu                                           24

<210> SEQ ID NO 161
<211> LENGTH: 25
<212> TYPE: RNA
<213> ORGANISM: Artificial
<220> FEATURE:
<223> OTHER INFORMATION: IsomiR sequence

<400> SEQUENCE: 161
ggaagacuag ugauuuuguu guuuu                                          25

<210> SEQ ID NO 162
<211> LENGTH: 19
<212> TYPE: RNA
<213> ORGANISM: Artificial
<220> FEATURE:
<223> OTHER INFORMATION: IsomiR sequence

<400> SEQUENCE: 162
ggaagacuag ugauuuugu                                                 19

<210> SEQ ID NO 163
<211> LENGTH: 24
<212> TYPE: RNA
<213> ORGANISM: Artificial
<220> FEATURE:
<223> OTHER INFORMATION: IsomiR sequence

<400> SEQUENCE: 163
gaagacuagu gauuuuguug uuuu                                           24

<210> SEQ ID NO 164
<211> LENGTH: 18
<212> TYPE: RNA
<213> ORGANISM: Artificial
<220> FEATURE:
<223> OTHER INFORMATION: IsomiR sequence

<400> SEQUENCE: 164
```
agacuaguga uuuuguug                                                      18

<210> SEQ ID NO 165
<211> LENGTH: 24
<212> TYPE: RNA
<213> ORGANISM: Artificial
<220> FEATURE:
<223> OTHER INFORMATION: IsomiR sequence

<400> SEQUENCE: 165
aagacuagug auuuuguugu uuuu                                               24

<210> SEQ ID NO 166
<211> LENGTH: 21
<212> TYPE: RNA
<213> ORGANISM: Artificial
<220> FEATURE:
<223> OTHER INFORMATION: IsomiR sequence

<400> SEQUENCE: 166
agacuaguga uuuuguuguu u                                                  21

<210> SEQ ID NO 167
<211> LENGTH: 21
<212> TYPE: RNA
<213> ORGANISM: Artificial
<220> FEATURE:
<223> OTHER INFORMATION: IsomiR sequence

<400> SEQUENCE: 167
aacaaaucac agucugccau a                                                  21

<210> SEQ ID NO 168
<211> LENGTH: 21
<212> TYPE: RNA
<213> ORGANISM: Artificial
<220> FEATURE:
<223> OTHER INFORMATION: IsomiR sequence

<400> SEQUENCE: 168
caacaaauca cagucugcca u                                                  21

<210> SEQ ID NO 169
<211> LENGTH: 22
<212> TYPE: RNA
<213> ORGANISM: Artificial
<220> FEATURE:
<223> OTHER INFORMATION: IsomiR sequence

<400> SEQUENCE: 169
caacaaguca cagccggccu ca                                                 22

<210> SEQ ID NO 170
<211> LENGTH: 20
<212> TYPE: RNA
<213> ORGANISM: Artificial
<220> FEATURE:
<223> OTHER INFORMATION: IsomiR sequence

<400> SEQUENCE: 170
caacaaauca cagucugcca                                                    20

<210> SEQ ID NO 171
<211> LENGTH: 22
<212> TYPE: RNA
<213> ORGANISM: Artificial

```
<220> FEATURE:
<223> OTHER INFORMATION: IsomiR sequence

<400> SEQUENCE: 171
aacaaaucac agucugccau au                                          22

<210> SEQ ID NO 172
<211> LENGTH: 20
<212> TYPE: RNA
<213> ORGANISM: Artificial
<220> FEATURE:
<223> OTHER INFORMATION: IsomiR sequence

<400> SEQUENCE: 172
aacaaaucac agucugccau                                             20

<210> SEQ ID NO 173
<211> LENGTH: 23
<212> TYPE: RNA
<213> ORGANISM: Artificial
<220> FEATURE:
<223> OTHER INFORMATION: IsomiR sequence

<400> SEQUENCE: 173
caacaaguca cagccggccu cau                                         23

<210> SEQ ID NO 174
<211> LENGTH: 23
<212> TYPE: RNA
<213> ORGANISM: Artificial
<220> FEATURE:
<223> OTHER INFORMATION: IsomiR sequence

<400> SEQUENCE: 174
caacaaauca cagucugcca uau                                         23

<210> SEQ ID NO 175
<211> LENGTH: 21
<212> TYPE: RNA
<213> ORGANISM: Artificial
<220> FEATURE:
<223> OTHER INFORMATION: IsomiR sequence

<400> SEQUENCE: 175
acaaaucaca gucugccaua u                                           21

<210> SEQ ID NO 176
<211> LENGTH: 21
<212> TYPE: RNA
<213> ORGANISM: Artificial
<220> FEATURE:
<223> OTHER INFORMATION: IsomiR sequence

<400> SEQUENCE: 176
caacaaguca cagccggccu c                                           21

<210> SEQ ID NO 177
<211> LENGTH: 21
<212> TYPE: RNA
<213> ORGANISM: Artificial
<220> FEATURE:
<223> OTHER INFORMATION: IsomiR sequence

<400> SEQUENCE: 177
aacaagucac agccggccuc a                                           21
```

```
<210> SEQ ID NO 178
<211> LENGTH: 22
<212> TYPE: RNA
<213> ORGANISM: Artificial
<220> FEATURE:
<223> OTHER INFORMATION: IsomiR sequence

<400> SEQUENCE: 178
uucaaguaau ucaggauagg uu                                                22

<210> SEQ ID NO 179
<211> LENGTH: 21
<212> TYPE: RNA
<213> ORGANISM: Artificial
<220> FEATURE:
<223> OTHER INFORMATION: IsomiR sequence

<400> SEQUENCE: 179
ucaaguaauu caggauaggu u                                                 21

<210> SEQ ID NO 180
<211> LENGTH: 20
<212> TYPE: RNA
<213> ORGANISM: Artificial
<220> FEATURE:
<223> OTHER INFORMATION: IsomiR sequence

<400> SEQUENCE: 180
uucaaguaau ucaggauagg                                                   20

<210> SEQ ID NO 181
<211> LENGTH: 21
<212> TYPE: RNA
<213> ORGANISM: Artificial
<220> FEATURE:
<223> OTHER INFORMATION: IsomiR sequence

<400> SEQUENCE: 181
ugagugugug ugugugagug u                                                 21

<210> SEQ ID NO 182
<211> LENGTH: 25
<212> TYPE: RNA
<213> ORGANISM: Artificial
<220> FEATURE:
<223> OTHER INFORMATION: IsomiR sequence

<400> SEQUENCE: 182
ugagugugug ugugugagug ugugu                                             25

<210> SEQ ID NO 183
<211> LENGTH: 22
<212> TYPE: RNA
<213> ORGANISM: Artificial
<220> FEATURE:
<223> OTHER INFORMATION: IsomiR sequence

<400> SEQUENCE: 183
ugagugugug ugugugagug ug                                                22

<210> SEQ ID NO 184
<211> LENGTH: 24
<212> TYPE: RNA
<213> ORGANISM: Artificial
<220> FEATURE:
<223> OTHER INFORMATION: IsomiR sequence
```

-continued

```
<400> SEQUENCE: 184
ugagugugug ugugugagug ugug                                            24

<210> SEQ ID NO 185
<211> LENGTH: 20
<212> TYPE: RNA
<213> ORGANISM: Artificial
<220> FEATURE:
<223> OTHER INFORMATION: IsomiR sequence

<400> SEQUENCE: 185
ugagugugug ugugugagug                                                 20

<210> SEQ ID NO 186
<211> LENGTH: 19
<212> TYPE: RNA
<213> ORGANISM: Artificial
<220> FEATURE:
<223> OTHER INFORMATION: IsomiR sequence

<400> SEQUENCE: 186
ugagugugug ugugugagu                                                  19

<210> SEQ ID NO 187
<211> LENGTH: 22
<212> TYPE: RNA
<213> ORGANISM: Artificial
<220> FEATURE:
<223> OTHER INFORMATION: IsomiR sequence

<400> SEQUENCE: 187
gagugugugu gugugagugu gu                                              22

<210> SEQ ID NO 188
<211> LENGTH: 20
<212> TYPE: RNA
<213> ORGANISM: Artificial
<220> FEATURE:
<223> OTHER INFORMATION: IsomiR sequence

<400> SEQUENCE: 188
gagugugugu gugugagugu                                                 20

<210> SEQ ID NO 189
<211> LENGTH: 22
<212> TYPE: RNA
<213> ORGANISM: Artificial
<220> FEATURE:
<223> OTHER INFORMATION: IsomiR sequence

<400> SEQUENCE: 189
gugagugugu gugugugagu gu                                              22

<210> SEQ ID NO 190
<211> LENGTH: 24
<212> TYPE: RNA
<213> ORGANISM: Artificial
<220> FEATURE:
<223> OTHER INFORMATION: IsomiR sequence

<400> SEQUENCE: 190
gagugugugu gugugagugu gugu                                            24

<210> SEQ ID NO 191
```

```
<211> LENGTH: 21
<212> TYPE: RNA
<213> ORGANISM: Artificial
<220> FEATURE:
<223> OTHER INFORMATION: IsomiR sequence

<400> SEQUENCE: 191
gagugugugu gugugagugu g                                              21

<210> SEQ ID NO 192
<211> LENGTH: 24
<212> TYPE: RNA
<213> ORGANISM: Artificial
<220> FEATURE:
<223> OTHER INFORMATION: IsomiR sequence

<400> SEQUENCE: 192
gugagugugu gugugugagu gugu                                           24

<210> SEQ ID NO 193
<211> LENGTH: 23
<212> TYPE: RNA
<213> ORGANISM: Artificial
<220> FEATURE:
<223> OTHER INFORMATION: IsomiR sequence

<400> SEQUENCE: 193
gagugugugu gugugagugu gug                                            23

<210> SEQ ID NO 194
<211> LENGTH: 18
<212> TYPE: RNA
<213> ORGANISM: Artificial
<220> FEATURE:
<223> OTHER INFORMATION: IsomiR sequence

<400> SEQUENCE: 194
ugagugugug ugugugag                                                  18

<210> SEQ ID NO 195
<211> LENGTH: 19
<212> TYPE: RNA
<213> ORGANISM: Artificial
<220> FEATURE:
<223> OTHER INFORMATION: IsomiR sequence

<400> SEQUENCE: 195
cugcgugggu gcgggcgug                                                 19

<210> SEQ ID NO 196
<211> LENGTH: 18
<212> TYPE: RNA
<213> ORGANISM: Artificial
<220> FEATURE:
<223> OTHER INFORMATION: IsomiR sequence

<400> SEQUENCE: 196
gagugugugu gugugagu                                                  18

<210> SEQ ID NO 197
<211> LENGTH: 21
<212> TYPE: RNA
<213> ORGANISM: Artificial
<220> FEATURE:
<223> OTHER INFORMATION: IsomiR sequence

<400> SEQUENCE: 197
```

```
cacgcucaug cacacaccca c                                            21

<210> SEQ ID NO 198
<211> LENGTH: 20
<212> TYPE: RNA
<213> ORGANISM: Artificial
<220> FEATURE:
<223> OTHER INFORMATION: IsomiR sequence

<400> SEQUENCE: 198
cacgcucaug cacacaccca                                              20

<210> SEQ ID NO 199
<211> LENGTH: 21
<212> TYPE: RNA
<213> ORGANISM: Artificial
<220> FEATURE:
<223> OTHER INFORMATION: IsomiR sequence

<400> SEQUENCE: 199
acgcucaugc acacacccac a                                            21

<210> SEQ ID NO 200
<211> LENGTH: 19
<212> TYPE: RNA
<213> ORGANISM: Artificial
<220> FEATURE:
<223> OTHER INFORMATION: IsomiR sequence

<400> SEQUENCE: 200
cacgcucaug cacacaccc                                               19

<210> SEQ ID NO 201
<211> LENGTH: 23
<212> TYPE: RNA
<213> ORGANISM: Artificial
<220> FEATURE:
<223> OTHER INFORMATION: IsomiR sequence

<400> SEQUENCE: 201
cacgcucaug cacacaccca cac                                          23

<210> SEQ ID NO 202
<211> LENGTH: 18
<212> TYPE: RNA
<213> ORGANISM: Artificial
<220> FEATURE:
<223> OTHER INFORMATION: IsomiR sequence

<400> SEQUENCE: 202
cacgcucaug cacacacc                                                18

<210> SEQ ID NO 203
<211> LENGTH: 20
<212> TYPE: RNA
<213> ORGANISM: Artificial
<220> FEATURE:
<223> OTHER INFORMATION: IsomiR sequence

<400> SEQUENCE: 203
cgcucaugca cacacccaca                                              20

<210> SEQ ID NO 204
<211> LENGTH: 20
<212> TYPE: RNA
```

```
<213> ORGANISM: Artificial
<220> FEATURE:
<223> OTHER INFORMATION: IsomiR sequence

<400> SEQUENCE: 204
acgcucaugc acacacccac                                                    20

<210> SEQ ID NO 205
<211> LENGTH: 22
<212> TYPE: RNA
<213> ORGANISM: Artificial
<220> FEATURE:
<223> OTHER INFORMATION: IsomiR sequence

<400> SEQUENCE: 205
ccacgcucau gcacacaccc ac                                                 22

<210> SEQ ID NO 206
<211> LENGTH: 20
<212> TYPE: RNA
<213> ORGANISM: Artificial
<220> FEATURE:
<223> OTHER INFORMATION: IsomiR sequence

<400> SEQUENCE: 206
uucacagugg cuaaguuccg                                                    20

<210> SEQ ID NO 207
<211> LENGTH: 19
<212> TYPE: RNA
<213> ORGANISM: Artificial
<220> FEATURE:
<223> OTHER INFORMATION: IsomiR sequence

<400> SEQUENCE: 207
uucacagugg cuaaguucc                                                     19

<210> SEQ ID NO 208
<211> LENGTH: 18
<212> TYPE: RNA
<213> ORGANISM: Artificial
<220> FEATURE:
<223> OTHER INFORMATION: IsomiR sequence

<400> SEQUENCE: 208
uucacagugg cuaaguuc                                                      18

<210> SEQ ID NO 209
<211> LENGTH: 17
<212> TYPE: RNA
<213> ORGANISM: Artificial
<220> FEATURE:
<223> OTHER INFORMATION: IsomiR sequence

<400> SEQUENCE: 209
uucacagugg cuaaguu                                                       17

<210> SEQ ID NO 210
<211> LENGTH: 21
<212> TYPE: RNA
<213> ORGANISM: Artificial
<220> FEATURE:
<223> OTHER INFORMATION: IsomiR sequence

<400> SEQUENCE: 210
uauugcacuu gucccggccu g                                                  21
```

```
<210> SEQ ID NO 211
<211> LENGTH: 20
<212> TYPE: RNA
<213> ORGANISM: Artificial
<220> FEATURE:
<223> OTHER INFORMATION: IsomiR sequence

<400> SEQUENCE: 211
uauugcacuu gucccggccu                                                   20

<210> SEQ ID NO 212
<211> LENGTH: 21
<212> TYPE: RNA
<213> ORGANISM: Artificial
<220> FEATURE:
<223> OTHER INFORMATION: IsomiR sequence

<400> SEQUENCE: 212
uaacagucua cagccauggu c                                                 21

<210> SEQ ID NO 213
<211> LENGTH: 20
<212> TYPE: RNA
<213> ORGANISM: Artificial
<220> FEATURE:
<223> OTHER INFORMATION: IsomiR sequence

<400> SEQUENCE: 213
uaacagucua cagccauggu                                                   20

<210> SEQ ID NO 214
<211> LENGTH: 21
<212> TYPE: RNA
<213> ORGANISM: Artificial
<220> FEATURE:
<223> OTHER INFORMATION: IsomiR sequence

<400> SEQUENCE: 214
aacagucuac agccaugguc g                                                 21

<210> SEQ ID NO 215
<211> LENGTH: 19
<212> TYPE: RNA
<213> ORGANISM: Artificial
<220> FEATURE:
<223> OTHER INFORMATION: IsomiR sequence

<400> SEQUENCE: 215
uaacagucua cagccaugg                                                    19

<210> SEQ ID NO 216
<211> LENGTH: 21
<212> TYPE: RNA
<213> ORGANISM: Artificial
<220> FEATURE:
<223> OTHER INFORMATION: IsomiR sequence

<400> SEQUENCE: 216
cguaccguga guaauaaugc g                                                 21

<210> SEQ ID NO 217
<211> LENGTH: 23
<212> TYPE: RNA
<213> ORGANISM: Artificial
<220> FEATURE:
```

<223> OTHER INFORMATION: IsomiR sequence

<400> SEQUENCE: 217
uagcuuauca gacugauguu gac                                           23

<210> SEQ ID NO 218
<211> LENGTH: 21
<212> TYPE: RNA
<213> ORGANISM: Artificial
<220> FEATURE:
<223> OTHER INFORMATION: IsomiR sequence

<400> SEQUENCE: 218
uagcuuauca gacugauguu g                                             21

<210> SEQ ID NO 219
<211> LENGTH: 22
<212> TYPE: RNA
<213> ORGANISM: Artificial
<220> FEATURE:
<223> OTHER INFORMATION: IsomiR sequence

<400> SEQUENCE: 219
guccaguuuu cccaggaauc cc                                            22

<210> SEQ ID NO 220
<211> LENGTH: 21
<212> TYPE: RNA
<213> ORGANISM: Artificial
<220> FEATURE:
<223> OTHER INFORMATION: IsomiR sequence

<400> SEQUENCE: 220
guccaguuuu cccaggaauc c                                             21

<210> SEQ ID NO 221
<211> LENGTH: 20
<212> TYPE: RNA
<213> ORGANISM: Artificial
<220> FEATURE:
<223> OTHER INFORMATION: IsomiR sequence

<400> SEQUENCE: 221
guccaguuuu cccaggaauc                                               20

<210> SEQ ID NO 222
<211> LENGTH: 19
<212> TYPE: RNA
<213> ORGANISM: Artificial
<220> FEATURE:
<223> OTHER INFORMATION: IsomiR sequence

<400> SEQUENCE: 222
guccaguuuu cccaggaau                                                19

<210> SEQ ID NO 223
<211> LENGTH: 22
<212> TYPE: RNA
<213> ORGANISM: Artificial
<220> FEATURE:
<223> OTHER INFORMATION: IsomiR sequence

<400> SEQUENCE: 223
agcuacauug ucugcugggu uu                                            22

-continued

```
<210> SEQ ID NO 224
<211> LENGTH: 21
<212> TYPE: RNA
<213> ORGANISM: Artificial
<220> FEATURE:
<223> OTHER INFORMATION: IsomiR sequence

<400> SEQUENCE: 224
agcuacauug ucugcugggu u                                              21

<210> SEQ ID NO 225
<211> LENGTH: 19
<212> TYPE: RNA
<213> ORGANISM: Artificial
<220> FEATURE:
<223> OTHER INFORMATION: IsomiR sequence

<400> SEQUENCE: 225
agcuacauug ucugcuggg                                                 19

<210> SEQ ID NO 226
<211> LENGTH: 23
<212> TYPE: RNA
<213> ORGANISM: Artificial
<220> FEATURE:
<223> OTHER INFORMATION: IsomiR sequence

<400> SEQUENCE: 226
agcuacaucu ggcuacuggg ucu                                            23

<210> SEQ ID NO 227
<211> LENGTH: 24
<212> TYPE: RNA
<213> ORGANISM: Artificial
<220> FEATURE:
<223> OTHER INFORMATION: IsomiR sequence

<400> SEQUENCE: 227
agcuacaucu ggcuacuggg ucuc                                           24

<210> SEQ ID NO 228
<211> LENGTH: 25
<212> TYPE: RNA
<213> ORGANISM: Artificial
<220> FEATURE:
<223> OTHER INFORMATION: IsomiR sequence

<400> SEQUENCE: 228
agcuacaucu ggcuacuggg ucucu                                          25

<210> SEQ ID NO 229
<211> LENGTH: 20
<212> TYPE: RNA
<213> ORGANISM: Artificial
<220> FEATURE:
<223> OTHER INFORMATION: IsomiR sequence

<400> SEQUENCE: 229
agcuacaucu ggcuacuggg                                                20

<210> SEQ ID NO 230
<211> LENGTH: 22
<212> TYPE: RNA
<213> ORGANISM: Artificial
<220> FEATURE:
<223> OTHER INFORMATION: IsomiR sequence
```

```
<400> SEQUENCE: 230
agcuacaucu ggcuacuggg uc                                              22

<210> SEQ ID NO 231
<211> LENGTH: 21
<212> TYPE: RNA
<213> ORGANISM: Artificial
<220> FEATURE:
<223> OTHER INFORMATION: IsomiR sequence

<400> SEQUENCE: 231
ugagguagua gguuguauag u                                               21

<210> SEQ ID NO 232
<211> LENGTH: 20
<212> TYPE: RNA
<213> ORGANISM: Artificial
<220> FEATURE:
<223> OTHER INFORMATION: IsomiR sequence

<400> SEQUENCE: 232
ugagguagua gguuguauag                                                 20

<210> SEQ ID NO 233
<211> LENGTH: 23
<212> TYPE: RNA
<213> ORGANISM: Artificial
<220> FEATURE:
<223> OTHER INFORMATION: IsomiR sequence

<400> SEQUENCE: 233
ugagguagua gguuguauag uuu                                             23

<210> SEQ ID NO 234
<211> LENGTH: 22
<212> TYPE: RNA
<213> ORGANISM: Artificial
<220> FEATURE:
<223> OTHER INFORMATION: IsomiR sequence

<400> SEQUENCE: 234
ugauauguuu gauauugggu ug                                              22

<210> SEQ ID NO 235
<211> LENGTH: 23
<212> TYPE: RNA
<213> ORGANISM: Artificial
<220> FEATURE:
<223> OTHER INFORMATION: IsomiR sequence

<400> SEQUENCE: 235
ugauauguuu gauauugggu ugu                                             23

<210> SEQ ID NO 236
<211> LENGTH: 20
<212> TYPE: RNA
<213> ORGANISM: Artificial
<220> FEATURE:
<223> OTHER INFORMATION: IsomiR sequence

<400> SEQUENCE: 236
ugauauguuu gauauugggu                                                 20

<210> SEQ ID NO 237
<211> LENGTH: 21
```

```
<212> TYPE: RNA
<213> ORGANISM: Artificial
<220> FEATURE:
<223> OTHER INFORMATION: IsomiR sequence

<400> SEQUENCE: 237
gauauguuug auauuggguu g                                              21

<210> SEQ ID NO 238
<211> LENGTH: 19
<212> TYPE: RNA
<213> ORGANISM: Artificial
<220> FEATURE:
<223> OTHER INFORMATION: IsomiR sequence

<400> SEQUENCE: 238
ugauauguuu gauauuggg                                                 19

<210> SEQ ID NO 239
<211> LENGTH: 22
<212> TYPE: RNA
<213> ORGANISM: Artificial
<220> FEATURE:
<223> OTHER INFORMATION: IsomiR sequence

<400> SEQUENCE: 239
gauauguuug auauuggguu gu                                             22

<210> SEQ ID NO 240
<211> LENGTH: 20
<212> TYPE: RNA
<213> ORGANISM: Artificial
<220> FEATURE:
<223> OTHER INFORMATION: IsomiR sequence

<400> SEQUENCE: 240
gauauguuug auauuggguu                                                20

<210> SEQ ID NO 241
<211> LENGTH: 21
<212> TYPE: RNA
<213> ORGANISM: Artificial
<220> FEATURE:
<223> OTHER INFORMATION: IsomiR sequence

<400> SEQUENCE: 241
cccauaaagu agaaagcacu a                                              21

<210> SEQ ID NO 242
<211> LENGTH: 20
<212> TYPE: RNA
<213> ORGANISM: Artificial
<220> FEATURE:
<223> OTHER INFORMATION: IsomiR sequence

<400> SEQUENCE: 242
cccauaaagu agaaagcacu                                                20

<210> SEQ ID NO 243
<211> LENGTH: 19
<212> TYPE: RNA
<213> ORGANISM: Artificial
<220> FEATURE:
<223> OTHER INFORMATION: IsomiR sequence

<400> SEQUENCE: 243
```

```
cauaaaguag aaagcacua                                               19

<210> SEQ ID NO 244
<211> LENGTH: 22
<212> TYPE: RNA
<213> ORGANISM: Artificial
<220> FEATURE:
<223> OTHER INFORMATION: IsomiR sequence

<400> SEQUENCE: 244
cauaaaguag aaagcacuac ua                                           22

<210> SEQ ID NO 245
<211> LENGTH: 22
<212> TYPE: RNA
<213> ORGANISM: Artificial
<220> FEATURE:
<223> OTHER INFORMATION: IsomiR sequence

<400> SEQUENCE: 245
cccauaaagu agaaagcacu ac                                           22

<210> SEQ ID NO 246
<211> LENGTH: 22
<212> TYPE: RNA
<213> ORGANISM: Artificial
<220> FEATURE:
<223> OTHER INFORMATION: IsomiR sequence

<400> SEQUENCE: 246
auaaaguaga aagcacuacu aa                                           22

<210> SEQ ID NO 247
<211> LENGTH: 20
<212> TYPE: RNA
<213> ORGANISM: Artificial
<220> FEATURE:
<223> OTHER INFORMATION: IsomiR sequence

<400> SEQUENCE: 247
cauaaaguag aaagcacuac                                              20

<210> SEQ ID NO 248
<211> LENGTH: 23
<212> TYPE: RNA
<213> ORGANISM: Artificial
<220> FEATURE:
<223> OTHER INFORMATION: IsomiR sequence

<400> SEQUENCE: 248
cauaaaguag aaagcacuac uaa                                          23

<210> SEQ ID NO 249
<211> LENGTH: 21
<212> TYPE: RNA
<213> ORGANISM: Artificial
<220> FEATURE:
<223> OTHER INFORMATION: IsomiR sequence

<400> SEQUENCE: 249
auaaaguaga aagcacuacu a                                            21

<210> SEQ ID NO 250
<211> LENGTH: 19
<212> TYPE: RNA
<213> ORGANISM: Artificial
```

```
<220> FEATURE:
<223> OTHER INFORMATION: IsomiR sequence

<400> SEQUENCE: 250
cccauaaagu agaaagcac                                                    19

<210> SEQ ID NO 251
<211> LENGTH: 18
<212> TYPE: RNA
<213> ORGANISM: Artificial
<220> FEATURE:
<223> OTHER INFORMATION: IsomiR sequence

<400> SEQUENCE: 251
cccauaaagu agaaagca                                                     18

<210> SEQ ID NO 252
<211> LENGTH: 18
<212> TYPE: RNA
<213> ORGANISM: Artificial
<220> FEATURE:
<223> OTHER INFORMATION: IsomiR sequence

<400> SEQUENCE: 252
cauaaaguag aaagcacu                                                     18

<210> SEQ ID NO 253
<211> LENGTH: 20
<212> TYPE: RNA
<213> ORGANISM: Artificial
<220> FEATURE:
<223> OTHER INFORMATION: IsomiR sequence

<400> SEQUENCE: 253
auaaaguaga aagcacuacu                                                   20

<210> SEQ ID NO 254
<211> LENGTH: 21
<212> TYPE: RNA
<213> ORGANISM: Artificial
<220> FEATURE:
<223> OTHER INFORMATION: IsomiR sequence

<400> SEQUENCE: 254
uaaaguagaa agcacuacua a                                                 21

<210> SEQ ID NO 255
<211> LENGTH: 20
<212> TYPE: RNA
<213> ORGANISM: Artificial
<220> FEATURE:
<223> OTHER INFORMATION: IsomiR sequence

<400> SEQUENCE: 255
ccauaaagua gaaagcacua                                                   20

<210> SEQ ID NO 256
<211> LENGTH: 21
<212> TYPE: RNA
<213> ORGANISM: Artificial
<220> FEATURE:
<223> OTHER INFORMATION: IsomiR sequence

<400> SEQUENCE: 256
ccauaaagua gaaagcacua c                                                 21
```

```
<210> SEQ ID NO 257
<211> LENGTH: 18
<212> TYPE: RNA
<213> ORGANISM: Artificial
<220> FEATURE:
<223> OTHER INFORMATION: IsomiR sequence

<400> SEQUENCE: 257
auaaaguaga aagcacua                                                 18

<210> SEQ ID NO 258
<211> LENGTH: 19
<212> TYPE: RNA
<213> ORGANISM: Artificial
<220> FEATURE:
<223> OTHER INFORMATION: IsomiR sequence

<400> SEQUENCE: 258
ccauaaagua gaaagcacu                                                19

<210> SEQ ID NO 259
<211> LENGTH: 22
<212> TYPE: RNA
<213> ORGANISM: Artificial
<220> FEATURE:
<223> OTHER INFORMATION: IsomiR sequence

<400> SEQUENCE: 259
acccauaaag uagaaagcac ua                                            22

<210> SEQ ID NO 260
<211> LENGTH: 20
<212> TYPE: RNA
<213> ORGANISM: Artificial
<220> FEATURE:
<223> OTHER INFORMATION: IsomiR sequence

<400> SEQUENCE: 260
uaaaguagaa agcacuacua                                               20

<210> SEQ ID NO 261
<211> LENGTH: 23
<212> TYPE: RNA
<213> ORGANISM: Artificial
<220> FEATURE:
<223> OTHER INFORMATION: IsomiR sequence

<400> SEQUENCE: 261
cccauaaagu agaaagcacu acu                                           23

<210> SEQ ID NO 262
<211> LENGTH: 19
<212> TYPE: RNA
<213> ORGANISM: Artificial
<220> FEATURE:
<223> OTHER INFORMATION: IsomiR sequence

<400> SEQUENCE: 262
auaaaguaga aagcacuac                                                19

<210> SEQ ID NO 263
<211> LENGTH: 21
<212> TYPE: RNA
<213> ORGANISM: Artificial
<220> FEATURE:
<223> OTHER INFORMATION: IsomiR sequence
```

```
<400> SEQUENCE: 263
acccauaaag uagaaagcac u                                            21

<210> SEQ ID NO 264
<211> LENGTH: 19
<212> TYPE: RNA
<213> ORGANISM: Artificial
<220> FEATURE:
<223> OTHER INFORMATION: IsomiR sequence

<400> SEQUENCE: 264
uaaaguagaa agcacuacu                                               19

<210> SEQ ID NO 265
<211> LENGTH: 24
<212> TYPE: RNA
<213> ORGANISM: Artificial
<220> FEATURE:
<223> OTHER INFORMATION: IsomiR sequence

<400> SEQUENCE: 265
cauaaaguag aaagcacuac uaac                                         24

<210> SEQ ID NO 266
<211> LENGTH: 20
<212> TYPE: RNA
<213> ORGANISM: Artificial
<220> FEATURE:
<223> OTHER INFORMATION: IsomiR sequence

<400> SEQUENCE: 266
aaaguagaaa gcacuacuaa                                              20

<210> SEQ ID NO 267
<211> LENGTH: 23
<212> TYPE: RNA
<213> ORGANISM: Artificial
<220> FEATURE:
<223> OTHER INFORMATION: IsomiR sequence

<400> SEQUENCE: 267
auaaaguaga aagcacuacu aac                                          23

<210> SEQ ID NO 268
<211> LENGTH: 18
<212> TYPE: RNA
<213> ORGANISM: Artificial
<220> FEATURE:
<223> OTHER INFORMATION: IsomiR sequence

<400> SEQUENCE: 268
aaguagaaag cacuacua                                                18

<210> SEQ ID NO 269
<211> LENGTH: 22
<212> TYPE: RNA
<213> ORGANISM: Artificial
<220> FEATURE:
<223> OTHER INFORMATION: IsomiR sequence

<400> SEQUENCE: 269
guaguguuuc cuacuuuaug ga                                           22

<210> SEQ ID NO 270
```

```
<211> LENGTH: 22
<212> TYPE: RNA
<213> ORGANISM: Artificial
<220> FEATURE:
<223> OTHER INFORMATION: IsomiR sequence

<400> SEQUENCE: 270
uguaguguuu ccuacuuuau gg                                                  22

<210> SEQ ID NO 271
<211> LENGTH: 21
<212> TYPE: RNA
<213> ORGANISM: Artificial
<220> FEATURE:
<223> OTHER INFORMATION: IsomiR sequence

<400> SEQUENCE: 271
guaguguuuc cuacuuuaug g                                                   21

<210> SEQ ID NO 272
<211> LENGTH: 21
<212> TYPE: RNA
<213> ORGANISM: Artificial
<220> FEATURE:
<223> OTHER INFORMATION: IsomiR sequence

<400> SEQUENCE: 272
uguaguguuu ccuacuuuau g                                                   21

<210> SEQ ID NO 273
<211> LENGTH: 20
<212> TYPE: RNA
<213> ORGANISM: Artificial
<220> FEATURE:
<223> OTHER INFORMATION: IsomiR sequence

<400> SEQUENCE: 273
uguaguguuu ccuacuuuau                                                     20

<210> SEQ ID NO 274
<211> LENGTH: 20
<212> TYPE: RNA
<213> ORGANISM: Artificial
<220> FEATURE:
<223> OTHER INFORMATION: IsomiR sequence

<400> SEQUENCE: 274
guaguguuuc cuacuuuaug                                                     20

<210> SEQ ID NO 275
<211> LENGTH: 21
<212> TYPE: RNA
<213> ORGANISM: Artificial
<220> FEATURE:
<223> OTHER INFORMATION: IsomiR sequence

<400> SEQUENCE: 275
uaguguuucc uacuuuaugg a                                                   21

<210> SEQ ID NO 276
<211> LENGTH: 18
<212> TYPE: RNA
<213> ORGANISM: Artificial
<220> FEATURE:
<223> OTHER INFORMATION: IsomiR sequence

<400> SEQUENCE: 276
```
uguaguguuu ccuacuuu                                                18

<210> SEQ ID NO 277
<211> LENGTH: 19
<212> TYPE: RNA
<213> ORGANISM: Artificial
<220> FEATURE:
<223> OTHER INFORMATION: IsomiR sequence

<400> SEQUENCE: 277
uguaguguuu ccuacuuua                                               19

<210> SEQ ID NO 278
<211> LENGTH: 20
<212> TYPE: RNA
<213> ORGANISM: Artificial
<220> FEATURE:
<223> OTHER INFORMATION: IsomiR sequence

<400> SEQUENCE: 278
uaguguuccu acuuuaugg                                               20

<210> SEQ ID NO 279
<211> LENGTH: 23
<212> TYPE: RNA
<213> ORGANISM: Artificial
<220> FEATURE:
<223> OTHER INFORMATION: IsomiR sequence

<400> SEQUENCE: 279
guaguguuuc cuacuuuaug gau                                          23

<210> SEQ ID NO 280
<211> LENGTH: 21
<212> TYPE: RNA
<213> ORGANISM: Artificial
<220> FEATURE:
<223> OTHER INFORMATION: IsomiR sequence

<400> SEQUENCE: 280
ugaguguacu gugggcuucg g                                            21

<210> SEQ ID NO 281
<211> LENGTH: 19
<212> TYPE: RNA
<213> ORGANISM: Artificial
<220> FEATURE:
<223> OTHER INFORMATION: IsomiR sequence

<400> SEQUENCE: 281
guaguguuuc cuacuuuau                                               19

<210> SEQ ID NO 282
<211> LENGTH: 21
<212> TYPE: RNA
<213> ORGANISM: Artificial
<220> FEATURE:
<223> OTHER INFORMATION: IsomiR sequence

<400> SEQUENCE: 282
aguguuuccu acuuuaugga u                                            21

<210> SEQ ID NO 283
<211> LENGTH: 20
<212> TYPE: RNA

```
<213> ORGANISM: Artificial
<220> FEATURE:
<223> OTHER INFORMATION: IsomiR sequence

<400> SEQUENCE: 283
aguguuuccu acuuuaugga                                                    20

<210> SEQ ID NO 284
<211> LENGTH: 22
<212> TYPE: RNA
<213> ORGANISM: Artificial
<220> FEATURE:
<223> OTHER INFORMATION: IsomiR sequence

<400> SEQUENCE: 284
ugaguguacu gugggcuucg ga                                                 22

<210> SEQ ID NO 285
<211> LENGTH: 22
<212> TYPE: RNA
<213> ORGANISM: Artificial
<220> FEATURE:
<223> OTHER INFORMATION: IsomiR sequence

<400> SEQUENCE: 285
guguaguguu uccuacuuua ug                                                 22

<210> SEQ ID NO 286
<211> LENGTH: 23
<212> TYPE: RNA
<213> ORGANISM: Artificial
<220> FEATURE:
<223> OTHER INFORMATION: IsomiR sequence

<400> SEQUENCE: 286
augaguguac ugugggcuuc gga                                                23

<210> SEQ ID NO 287
<211> LENGTH: 19
<212> TYPE: RNA
<213> ORGANISM: Artificial
<220> FEATURE:
<223> OTHER INFORMATION: IsomiR sequence

<400> SEQUENCE: 287
uaguguuccc uacuuuaug                                                     19

<210> SEQ ID NO 288
<211> LENGTH: 23
<212> TYPE: RNA
<213> ORGANISM: Artificial
<220> FEATURE:
<223> OTHER INFORMATION: IsomiR sequence

<400> SEQUENCE: 288
aguguuuccu acuuuaugga uga                                                23

<210> SEQ ID NO 289
<211> LENGTH: 22
<212> TYPE: RNA
<213> ORGANISM: Artificial
<220> FEATURE:
<223> OTHER INFORMATION: IsomiR sequence

<400> SEQUENCE: 289
aguguuuccu acuuuaugga ug                                                 22
```

```
<210> SEQ ID NO 290
<211> LENGTH: 22
<212> TYPE: RNA
<213> ORGANISM: Artificial
<220> FEATURE:
<223> OTHER INFORMATION: IsomiR sequence

<400> SEQUENCE: 290
ucuuugguua ucuagcugua ug                                              22

<210> SEQ ID NO 291
<211> LENGTH: 20
<212> TYPE: RNA
<213> ORGANISM: Artificial
<220> FEATURE:
<223> OTHER INFORMATION: IsomiR sequence

<400> SEQUENCE: 291
ucuuugguua ucuagcugua                                                 20

<210> SEQ ID NO 292
<211> LENGTH: 21
<212> TYPE: RNA
<213> ORGANISM: Artificial
<220> FEATURE:
<223> OTHER INFORMATION: IsomiR sequence

<400> SEQUENCE: 292
ucuuugguua ucuagcugua u                                               21

<210> SEQ ID NO 293
<211> LENGTH: 22
<212> TYPE: RNA
<213> ORGANISM: Artificial
<220> FEATURE:
<223> OTHER INFORMATION: IsomiR sequence

<400> SEQUENCE: 293
uaaagcuaga uaaccgaaag ua                                              22

<210> SEQ ID NO 294
<211> LENGTH: 21
<212> TYPE: RNA
<213> ORGANISM: Artificial
<220> FEATURE:
<223> OTHER INFORMATION: IsomiR sequence

<400> SEQUENCE: 294
uaaagcuaga uaaccgaaag u                                               21

<210> SEQ ID NO 295
<211> LENGTH: 23
<212> TYPE: RNA
<213> ORGANISM: Artificial
<220> FEATURE:
<223> OTHER INFORMATION: IsomiR sequence

<400> SEQUENCE: 295
uaaagcuaga uaaccgaaag uaa                                             23

<210> SEQ ID NO 296
<211> LENGTH: 23
<212> TYPE: RNA
<220> FEATURE:
```

<223> OTHER INFORMATION: IsomiR sequence

<400> SEQUENCE: 296
auaaagcuag auaaccgaaa gua                                              23

<210> SEQ ID NO 297
<211> LENGTH: 21
<212> TYPE: RNA
<213> ORGANISM: Artificial
<220> FEATURE:
<223> OTHER INFORMATION: IsomiR sequence

<400> SEQUENCE: 297
auaaagcuag auaaccgaaa g                                                21

<210> SEQ ID NO 298
<211> LENGTH: 20
<212> TYPE: RNA
<213> ORGANISM: Artificial
<220> FEATURE:
<223> OTHER INFORMATION: IsomiR sequence

<400> SEQUENCE: 298
auaaagcuag auaaccgaaa                                                  20

<210> SEQ ID NO 299
<211> LENGTH: 24
<212> TYPE: RNA
<213> ORGANISM: Artificial
<220> FEATURE:
<223> OTHER INFORMATION: IsomiR sequence

<400> SEQUENCE: 299
auaaagcuag auaaccgaaa guaa                                             24

<210> SEQ ID NO 300
<211> LENGTH: 20
<212> TYPE: RNA
<213> ORGANISM: Artificial
<220> FEATURE:
<223> OTHER INFORMATION: IsomiR sequence

<400> SEQUENCE: 300
uaaagcuaga uaaccgaaag                                                  20

<210> SEQ ID NO 301
<211> LENGTH: 24
<212> TYPE: RNA
<213> ORGANISM: Artificial
<220> FEATURE:
<223> OTHER INFORMATION: IsomiR sequence

<400> SEQUENCE: 301
uaaagcuaga uaaccgaaag uaaa                                             24

<210> SEQ ID NO 302
<211> LENGTH: 19
<212> TYPE: RNA
<213> ORGANISM: Artificial
<220> FEATURE:
<223> OTHER INFORMATION: IsomiR sequence

<400> SEQUENCE: 302
uaaagcuaga uaaccgaaa                                                   19

```
<210> SEQ ID NO 303
<211> LENGTH: 23
<212> TYPE: RNA
<213> ORGANISM: Artificial
<220> FEATURE:
<223> OTHER INFORMATION: IsomiR sequence

<400> SEQUENCE: 303
uaaagcuaga uaaccgaaag uag                                               23

<210> SEQ ID NO 304
<211> LENGTH: 20
<212> TYPE: RNA
<213> ORGANISM: Artificial
<220> FEATURE:
<223> OTHER INFORMATION: IsomiR sequence

<400> SEQUENCE: 304
aaagcuagau aaccgaaagu                                                   20

<210> SEQ ID NO 305
<211> LENGTH: 22
<212> TYPE: RNA
<213> ORGANISM: Artificial
<220> FEATURE:
<223> OTHER INFORMATION: Antagomir sequence

<400> SEQUENCE: 305
cgaccauggc uguagacugu ua                                                22

<210> SEQ ID NO 306
<211> LENGTH: 22
<212> TYPE: RNA
<213> ORGANISM: Artificial
<220> FEATURE:
<223> OTHER INFORMATION: Antagomir sequence

<400> SEQUENCE: 306
aguaacaauc gaaagccacg gu                                                22

<210> SEQ ID NO 307
<211> LENGTH: 22
<212> TYPE: RNA
<213> ORGANISM: Artificial
<220> FEATURE:
<223> OTHER INFORMATION: Antagomir sequence

<400> SEQUENCE: 307
cgcauuauua cucacgguac ga                                                22

<210> SEQ ID NO 308
<211> LENGTH: 21
<212> TYPE: RNA
<213> ORGANISM: Artificial
<220> FEATURE:
<223> OTHER INFORMATION: Antagomir sequence

<400> SEQUENCE: 308
cgcguaccaa aaguaauaau g                                                 21

<210> SEQ ID NO 309
<211> LENGTH: 22
<212> TYPE: RNA
<213> ORGANISM: Artificial
<220> FEATURE:
<223> OTHER INFORMATION: Antagomir sequence
```

<400> SEQUENCE: 309
ucaacaucag ucugauaagc ua                                    22

<210> SEQ ID NO 310
<211> LENGTH: 21
<212> TYPE: RNA
<213> ORGANISM: Artificial
<220> FEATURE:
<223> OTHER INFORMATION: Antagomir sequence

<400> SEQUENCE: 310
acagcccauc gacuggeuguu g                                    21

<210> SEQ ID NO 311
<211> LENGTH: 23
<212> TYPE: DNA
<213> ORGANISM: Artificial
<220> FEATURE:
<223> OTHER INFORMATION: Primer sequence

<400> SEQUENCE: 311
cacgctgttt tgacctccat aga                                   23

<210> SEQ ID NO 312
<211> LENGTH: 18
<212> TYPE: DNA
<213> ORGANISM: Artificial
<220> FEATURE:
<223> OTHER INFORMATION: Primer sequence

<400> SEQUENCE: 312
cactgacggg caccggag                                         18

<210> SEQ ID NO 313
<211> LENGTH: 28
<212> TYPE: DNA
<213> ORGANISM: Artificial
<220> FEATURE:
<223> OTHER INFORMATION: Primer sequence

<400> SEQUENCE: 313
gacctccata gaagattcta gagctagc                              28

<210> SEQ ID NO 314
<211> LENGTH: 49
<212> TYPE: DNA
<213> ORGANISM: Artificial
<220> FEATURE:
<223> OTHER INFORMATION: Primer sequence

<400> SEQUENCE: 314
gtcgtatcca gtgcagggtc cgaggtattc gcactggata cgaacaaca       49

<210> SEQ ID NO 315
<211> LENGTH: 26
<212> TYPE: DNA
<213> ORGANISM: Artificial
<220> FEATURE:
<223> OTHER INFORMATION: Primer sequence

<400> SEQUENCE: 315
gcccgcttgg aagactagtg attttg                                26

<210> SEQ ID NO 316
<211> LENGTH: 50

```
<212> TYPE: DNA
<213> ORGANISM: Artificial
<220> FEATURE:
<223> OTHER INFORMATION: Primer sequence

<400> SEQUENCE: 316
gtcgtatcca gtgcagggtc cgaggtattc gcactggata cgacacctat              50

<210> SEQ ID NO 317
<211> LENGTH: 23
<212> TYPE: DNA
<213> ORGANISM: Artificial
<220> FEATURE:
<223> OTHER INFORMATION: Primer sequence

<400> SEQUENCE: 317
tgccagttca agtaattcag gat                                           23

<210> SEQ ID NO 318
<211> LENGTH: 50
<212> TYPE: DNA
<213> ORGANISM: Artificial
<220> FEATURE:
<223> OTHER INFORMATION: Primer sequence

<400> SEQUENCE: 318
gtcgtatcca gtgcagggtc cgaggtattc gcactggata cgacgagcca              50

<210> SEQ ID NO 319
<211> LENGTH: 24
<212> TYPE: DNA
<213> ORGANISM: Artificial
<220> FEATURE:
<223> OTHER INFORMATION: Primer sequence

<400> SEQUENCE: 319
tgccagcctg ttctccatta cttg                                          24

<210> SEQ ID NO 320
<211> LENGTH: 50
<212> TYPE: DNA
<213> ORGANISM: Artificial
<220> FEATURE:
<223> OTHER INFORMATION: Primer sequence

<400> SEQUENCE: 320
gtcgtatcca gtgcagggtc cgaggtattc gcactggata cgacacacac              50

<210> SEQ ID NO 321
<211> LENGTH: 25
<212> TYPE: DNA
<213> ORGANISM: Artificial
<220> FEATURE:
<223> OTHER INFORMATION: Primer sequence

<400> SEQUENCE: 321
tgccagtgag tgtgtgtgtg tgagt                                         25

<210> SEQ ID NO 322
<211> LENGTH: 50
<212> TYPE: DNA
<213> ORGANISM: Artificial
<220> FEATURE:
<223> OTHER INFORMATION: Primer sequence

<400> SEQUENCE: 322
```

```
gtcgtatcca gtgcagggtc cgaggtattc gcactggata cgactgtggg          50
```

<210> SEQ ID NO 323
<211> LENGTH: 24
<212> TYPE: DNA
<213> ORGANISM: Artificial
<220> FEATURE:
<223> OTHER INFORMATION: Primer sequence

<400> SEQUENCE: 323

```
tgccagcacg ctcatgcaca cacc                                      24
```

<210> SEQ ID NO 324
<211> LENGTH: 50
<212> TYPE: DNA
<213> ORGANISM: Artificial
<220> FEATURE:
<223> OTHER INFORMATION: Primer sequence

<400> SEQUENCE: 324

```
gtcgtatcca gtgcagggtc cgaggtattc gcactggata cgacgcggaa          50
```

<210> SEQ ID NO 325
<211> LENGTH: 23
<212> TYPE: DNA
<213> ORGANISM: Artificial
<220> FEATURE:
<223> OTHER INFORMATION: Primer sequence

<400> SEQUENCE: 325

```
tgccagttca cagtggctaa gtt                                       23
```

<210> SEQ ID NO 326
<211> LENGTH: 50
<212> TYPE: DNA
<213> ORGANISM: Artificial
<220> FEATURE:
<223> OTHER INFORMATION: Primer sequence

<400> SEQUENCE: 326

```
gtcgtatcca gtgcagggtc cgaggtattc gcactggata cgactgctca          50
```

<210> SEQ ID NO 327
<211> LENGTH: 24
<212> TYPE: DNA
<213> ORGANISM: Artificial
<220> FEATURE:
<223> OTHER INFORMATION: Primer sequence

<400> SEQUENCE: 327

```
tgccagaggg cttagctgct tgtg                                      24
```

<210> SEQ ID NO 328
<211> LENGTH: 49
<212> TYPE: DNA
<213> ORGANISM: Artificial
<220> FEATURE:
<223> OTHER INFORMATION: Primer sequence

<400> SEQUENCE: 328

```
gtcgtatcca gtgcagggtc cgaggtattc gcactggata cgaacaggc           49
```

<210> SEQ ID NO 329
<211> LENGTH: 24
<212> TYPE: DNA
<213> ORGANISM: Artificial

```
<220> FEATURE:
<223> OTHER INFORMATION: Primer sequence

<400> SEQUENCE: 329
tgccagtatt gcacttgtcc cggc                                              24

<210> SEQ ID NO 330
<211> LENGTH: 49
<212> TYPE: DNA
<213> ORGANISM: Artificial
<220> FEATURE:
<223> OTHER INFORMATION: Primer sequence

<400> SEQUENCE: 330
gtcgtatcca gtgcagggtc cgaggtattc gcactggata cgaaaccca                   49

<210> SEQ ID NO 331
<211> LENGTH: 25
<212> TYPE: DNA
<213> ORGANISM: Artificial
<220> FEATURE:
<223> OTHER INFORMATION: Primer sequence

<400> SEQUENCE: 331
gcccgctaag cccttacccc aaaaa                                             25

<210> SEQ ID NO 332
<211> LENGTH: 50
<212> TYPE: DNA
<213> ORGANISM: Artificial
<220> FEATURE:
<223> OTHER INFORMATION: Primer sequence

<400> SEQUENCE: 332
gtcgtatcca gtgcagggtc cgaggtattc gcactggata cgacagtagt                  50

<210> SEQ ID NO 333
<211> LENGTH: 23
<212> TYPE: DNA
<213> ORGANISM: Artificial
<220> FEATURE:
<223> OTHER INFORMATION: Primer sequence

<400> SEQUENCE: 333
gcccgccata aagtagaaag cac                                               23

<210> SEQ ID NO 334
<211> LENGTH: 50
<212> TYPE: DNA
<213> ORGANISM: Artificial
<220> FEATURE:
<223> OTHER INFORMATION: Primer sequence

<400> SEQUENCE: 334
gtcgtatcca gtgcagggtc cgaggtattc gcactggata cgactccata                  50

<210> SEQ ID NO 335
<211> LENGTH: 25
<212> TYPE: DNA
<213> ORGANISM: Artificial
<220> FEATURE:
<223> OTHER INFORMATION: Primer sequence

<400> SEQUENCE: 335
tgccagtgta gtgtttccta cttta                                             25
```

<210> SEQ ID NO 336
<211> LENGTH: 50
<212> TYPE: DNA
<213> ORGANISM: Artificial
<220> FEATURE:
<223> OTHER INFORMATION: Primer sequence

<400> SEQUENCE: 336
gtcgtatcca gtgcagggtc cgaggtattc gcactggata cgactcatac        50

<210> SEQ ID NO 337
<211> LENGTH: 25
<212> TYPE: DNA
<213> ORGANISM: Artificial
<220> FEATURE:
<223> OTHER INFORMATION: Primer sequence

<400> SEQUENCE: 337
tgccagtctt tggttatcta gctgt        25

<210> SEQ ID NO 338
<211> LENGTH: 50
<212> TYPE: DNA
<213> ORGANISM: Artificial
<220> FEATURE:
<223> OTHER INFORMATION: Primer sequence

<400> SEQUENCE: 338
gtcgtatcca gtgcagggtc cgaggtattc gcactggata cgacactttc        50

<210> SEQ ID NO 339
<211> LENGTH: 24
<212> TYPE: DNA
<213> ORGANISM: Artificial
<220> FEATURE:
<223> OTHER INFORMATION: Primer sequence

<400> SEQUENCE: 339
tgccagataa agctagataa ccga        24

<210> SEQ ID NO 340
<211> LENGTH: 16
<212> TYPE: DNA
<213> ORGANISM: Artificial
<220> FEATURE:
<223> OTHER INFORMATION: Primer sequence

<400> SEQUENCE: 340
gtgcagggtc cgaggt        16

<210> SEQ ID NO 341
<211> LENGTH: 16
<212> TYPE: DNA
<213> ORGANISM: Artificial
<220> FEATURE:
<223> OTHER INFORMATION: Primer sequence

<400> SEQUENCE: 341
gtcatccttg cgcagg        16

<210> SEQ ID NO 342
<211> LENGTH: 20
<212> TYPE: DNA
<213> ORGANISM: Artificial
<220> FEATURE:
<223> OTHER INFORMATION: Primer sequence

```
<400> SEQUENCE: 342
cgcttcggca gcacatatac                                               20

<210> SEQ ID NO 343
<211> LENGTH: 20
<212> TYPE: DNA
<213> ORGANISM: Artificial
<220> FEATURE:
<223> OTHER INFORMATION: Primer sequence

<400> SEQUENCE: 343
aggggccatg ctaatcttct                                               20

<210> SEQ ID NO 344
<211> LENGTH: 23
<212> TYPE: DNA
<213> ORGANISM: Artificial
<220> FEATURE:
<223> OTHER INFORMATION: Primer sequence

<400> SEQUENCE: 344
cacgctgttt tgacctccat aga                                           23

<210> SEQ ID NO 345
<211> LENGTH: 18
<212> TYPE: DNA
<213> ORGANISM: Artificial
<220> FEATURE:
<223> OTHER INFORMATION: Primer sequence

<400> SEQUENCE: 345
cactgacggg caccggag                                                 18

<210> SEQ ID NO 346
<211> LENGTH: 21
<212> TYPE: DNA
<213> ORGANISM: Artificial
<220> FEATURE:
<223> OTHER INFORMATION: Primer sequence

<400> SEQUENCE: 346
caucgucgau cguagcgcat t                                             21

<210> SEQ ID NO 347
<211> LENGTH: 21
<212> TYPE: DNA
<213> ORGANISM: Artificial
<220> FEATURE:
<223> OTHER INFORMATION: Primer sequence

<400> SEQUENCE: 347
ugcgcuacga ucgacgaugt t                                             21

<210> SEQ ID NO 348
<211> LENGTH: 7
<212> TYPE: RNA
<213> ORGANISM: Artificial
<220> FEATURE:
<223> OTHER INFORMATION: Seed sequence

<400> SEQUENCE: 348 ggaagac                                                             7

<210> SEQ ID NO 349
```

```
<211> LENGTH: 7
<212> TYPE: RNA
<213> ORGANISM: Artificial
<220> FEATURE:
<223> OTHER INFORMATION: Seed sequence

<400> SEQUENCE: 349 aacaaau                                                               7

<210> SEQ ID NO 350
<211> LENGTH: 7
<212> TYPE: RNA
<213> ORGANISM: Artificial
<220> FEATURE:
<223> OTHER INFORMATION: Seed sequence

<400> SEQUENCE: 350 aacaaau                                                               7

<210> SEQ ID NO 351
<211> LENGTH: 7
<212> TYPE: RNA
<213> ORGANISM: Artificial
<220> FEATURE:
<223> OTHER INFORMATION: Seed sequence

<400> SEQUENCE: 351 ucaagua                                                               7

<210> SEQ ID NO 352
<211> LENGTH: 7
<212> TYPE: RNA
<213> ORGANISM: Artificial
<220> FEATURE:
<223> OTHER INFORMATION: Seed sequence

<400> SEQUENCE: 352 cuguucu                                                               7

<210> SEQ ID NO 353
<211> LENGTH: 7
<212> TYPE: RNA
<213> ORGANISM: Artificial
<220> FEATURE:
<223> OTHER INFORMATION: Seed sequence

<400> SEQUENCE: 353 gagugug                                                               7

<210> SEQ ID NO 354
<211> LENGTH: 7
<212> TYPE: RNA
<213> ORGANISM: Artificial
<220> FEATURE:
<223> OTHER INFORMATION: Seed sequence

<400> SEQUENCE: 354 acgcuca                                                               7

<210> SEQ ID NO 355
<211> LENGTH: 7
<212> TYPE: RNA
<213> ORGANISM: Artificial
<220> FEATURE:
<223> OTHER INFORMATION: Seed sequence

<400> SEQUENCE: 355
```

```
ucacagu                                                         7

<210> SEQ ID NO 356
<211> LENGTH: 7
<212> TYPE: RNA
<213> ORGANISM: Artificial
<220> FEATURE:
<223> OTHER INFORMATION: Seed sequence

<400> SEQUENCE: 356 gggcuua                                                         7

<210> SEQ ID NO 357
<211> LENGTH: 7
<212> TYPE: RNA
<213> ORGANISM: Artificial
<220> FEATURE:
<223> OTHER INFORMATION: Seed sequence

<400> SEQUENCE: 357 auugcac                                                         7

<210> SEQ ID NO 358
<211> LENGTH: 7
<212> TYPE: RNA
<213> ORGANISM: Artificial
<220> FEATURE:
<223> OTHER INFORMATION: Seed sequence

<400> SEQUENCE: 358 gguuggg                                                         7

<210> SEQ ID NO 359
<211> LENGTH: 7
<212> TYPE: RNA
<213> ORGANISM: Artificial
<220> FEATURE:
<223> OTHER INFORMATION: Seed sequence

<400> SEQUENCE: 359 aacaguc                                                         7

<210> SEQ ID NO 360
<211> LENGTH: 7
<212> TYPE: RNA
<213> ORGANISM: Artificial
<220> FEATURE:
<223> OTHER INFORMATION: Seed sequence

<400> SEQUENCE: 360 ccguggc                                                         7

<210> SEQ ID NO 361
<211> LENGTH: 7
<212> TYPE: RNA
<213> ORGANISM: Artificial
<220> FEATURE:
<223> OTHER INFORMATION: Seed sequence

<400> SEQUENCE: 361 cguaccg                                                         7

<210> SEQ ID NO 362
<211> LENGTH: 7
<212> TYPE: RNA
```

```
<213> ORGANISM: Artificial
<220> FEATURE:
<223> OTHER INFORMATION: Seed sequence

<400> SEQUENCE: 362 auuauua                                                                    7

<210> SEQ ID NO 363
<211> LENGTH: 7
<212> TYPE: RNA
<213> ORGANISM: Artificial
<220> FEATURE:
<223> OTHER INFORMATION: Seed sequence

<400> SEQUENCE: 363 agcuuau                                                                    7

<210> SEQ ID NO 364
<211> LENGTH: 7
<212> TYPE: RNA
<213> ORGANISM: Artificial
<220> FEATURE:
<223> OTHER INFORMATION: Seed sequence

<400> SEQUENCE: 364 aacacca                                                                    7

<210> SEQ ID NO 365
<211> LENGTH: 7
<212> TYPE: RNA
<213> ORGANISM: Artificial
<220> FEATURE:
<223> OTHER INFORMATION: Seed sequence

<400> SEQUENCE: 365 uccaguu                                                                    7

<210> SEQ ID NO 366
<211> LENGTH: 7
<212> TYPE: RNA
<213> ORGANISM: Artificial
<220> FEATURE:
<223> OTHER INFORMATION: Seed sequence

<400> SEQUENCE: 366 gauuccu                                                                    7

<210> SEQ ID NO 367
<211> LENGTH: 7
<212> TYPE: RNA
<213> ORGANISM: Artificial
<220> FEATURE:
<223> OTHER INFORMATION: Seed sequence

<400> SEQUENCE: 367 gagguag                                                                    7

<210> SEQ ID NO 368
<211> LENGTH: 7
<212> TYPE: RNA
<213> ORGANISM: Artificial
<220> FEATURE:
<223> OTHER INFORMATION: Seed sequence

<400> SEQUENCE: 368 uauacaa                                                                    7
```

```
<210> SEQ ID NO 369
<211> LENGTH: 7
<212> TYPE: RNA
<213> ORGANISM: Artificial
<220> FEATURE:
<223> OTHER INFORMATION: Seed sequence

<400> SEQUENCE: 369 uguacag                                                                   7

<210> SEQ ID NO 370
<211> LENGTH: 7
<212> TYPE: RNA
<213> ORGANISM: Artificial
<220> FEATURE:
<223> OTHER INFORMATION: Seed sequence

<400> SEQUENCE: 370 gcuacau                                                                   7

<210> SEQ ID NO 371
<211> LENGTH: 7
<212> TYPE: RNA
<213> ORGANISM: Artificial
<220> FEATURE:
<223> OTHER INFORMATION: Seed sequence

<400> SEQUENCE: 371 ccuggca                                                                   7

<210> SEQ ID NO 372
<211> LENGTH: 7
<212> TYPE: RNA
<213> ORGANISM: Artificial
<220> FEATURE:
<223> OTHER INFORMATION: Seed sequence

<400> SEQUENCE: 372 gcuacau                                                                   7

<210> SEQ ID NO 373
<211> LENGTH: 7
<212> TYPE: RNA
<213> ORGANISM: Artificial
<220> FEATURE:
<223> OTHER INFORMATION: Seed sequence

<400> SEQUENCE: 373 ucaguag                                                                   7

<210> SEQ ID NO 374
<211> LENGTH: 7
<212> TYPE: RNA
<213> ORGANISM: Artificial
<220> FEATURE:
<223> OTHER INFORMATION: Seed sequence

<400> SEQUENCE: 374 gauaugu                                                                   7

<210> SEQ ID NO 375
<211> LENGTH: 7
<212> TYPE: RNA
<220> FEATURE:
```

```
<223> OTHER INFORMATION: Seed sequence

<400> SEQUENCE: 375 auaaagu                                                                    7

<210> SEQ ID NO 376
<211> LENGTH: 7
<212> TYPE: RNA
<213> ORGANISM: Artificial
<220> FEATURE:
<223> OTHER INFORMATION: Seed sequence

<400> SEQUENCE: 376 guagugu                                                                    7

<210> SEQ ID NO 377
<211> LENGTH: 7
<212> TYPE: RNA
<213> ORGANISM: Artificial
<220> FEATURE:
<223> OTHER INFORMATION: Seed sequence

<400> SEQUENCE: 377 cuuuggu                                                                    7

<210> SEQ ID NO 378
<211> LENGTH: 7
<212> TYPE: RNA
<213> ORGANISM: Artificial
<220> FEATURE:
<223> OTHER INFORMATION: Seed sequence

<400> SEQUENCE: 378 uaaagcu                                                                    7

<210> SEQ ID NO 379
<211> LENGTH: 7
<212> TYPE: RNA
<213> ORGANISM: Artificial
<220> FEATURE:
<223> OTHER INFORMATION: seed sequence

<400> SEQUENCE: 379 uuugguu                                                                    7

<210> SEQ ID NO 380
<211> LENGTH: 7
<212> TYPE: RNA
<213> ORGANISM: Artificial
<220> FEATURE:
<223> OTHER INFORMATION: seed sequence

<400> SEQUENCE: 380 uugguua                                                                    7

<210> SEQ ID NO 381
<211> LENGTH: 7
<212> TYPE: RNA
<213> ORGANISM: Artificial
<220> FEATURE:
<223> OTHER INFORMATION: seed sequence

<400> SEQUENCE: 381 ucuuugg                                                                    7
```

```
<210> SEQ ID NO 382
<211> LENGTH: 19
<212> TYPE: RNA
<213> ORGANISM: Artificial
<220> FEATURE:
<223> OTHER INFORMATION: isomir

<400> SEQUENCE: 382
ucuuugguua ucuagcugu                                                19

<210> SEQ ID NO 383
<211> LENGTH: 22
<212> TYPE: RNA
<213> ORGANISM: Artificial
<220> FEATURE:
<223> OTHER INFORMATION: isomir

<400> SEQUENCE: 383
cuuugguuau cuagcuguau ga                                            22

<210> SEQ ID NO 384
<211> LENGTH: 18
<212> TYPE: RNA
<213> ORGANISM: Artificial
<220> FEATURE:
<223> OTHER INFORMATION: isomir

<400> SEQUENCE: 384
ucuuugguua ucuagcug                                                 18

<210> SEQ ID NO 385
<211> LENGTH: 24
<212> TYPE: RNA
<213> ORGANISM: Artificial
<220> FEATURE:
<223> OTHER INFORMATION: isomir

<400> SEQUENCE: 385
ucuuugguua ucuagcugua ugag                                          24

<210> SEQ ID NO 386
<211> LENGTH: 21
<212> TYPE: RNA
<213> ORGANISM: Artificial
<220> FEATURE:
<223> OTHER INFORMATION: isomir

<400> SEQUENCE: 386
cuuugguuau cuagcuguau g                                             21

<210> SEQ ID NO 387
<211> LENGTH: 21
<212> TYPE: RNA
<213> ORGANISM: Artificial
<220> FEATURE:
<223> OTHER INFORMATION: isomir

<400> SEQUENCE: 387
uuugguuauc uagcuguaug a                                             21

<210> SEQ ID NO 388
<211> LENGTH: 20
<212> TYPE: RNA
<213> ORGANISM: Artificial
<220> FEATURE:
<223> OTHER INFORMATION: isomir
```

```
<400> SEQUENCE: 388
cuuugguuau cuagcuguau                                               20

<210> SEQ ID NO 389
<211> LENGTH: 19
<212> TYPE: RNA
<213> ORGANISM: Artificial
<220> FEATURE:
<223> OTHER INFORMATION: isomir

<400> SEQUENCE: 389
cuuugguuau cuagcugua                                                19

<210> SEQ ID NO 390
<211> LENGTH: 23
<212> TYPE: RNA
<213> ORGANISM: Artificial
<220> FEATURE:
<223> OTHER INFORMATION: isomir

<400> SEQUENCE: 390
cuuugguuau cuagcuguau gag                                           23

<210> SEQ ID NO 391
<211> LENGTH: 23
<212> TYPE: RNA
<213> ORGANISM: Artificial
<220> FEATURE:
<223> OTHER INFORMATION: isomir

<400> SEQUENCE: 391
aucuuugguu aucuagcugu aug                                           23

<210> SEQ ID NO 392
<211> LENGTH: 22
<212> TYPE: RNA
<213> ORGANISM: Artificial
<220> FEATURE:
<223> OTHER INFORMATION: isomir

<400> SEQUENCE: 392
uuugguuauc uagcuguaug ag                                            22

<210> SEQ ID NO 393
<211> LENGTH: 24
<212> TYPE: RNA
<213> ORGANISM: Artificial
<220> FEATURE:
<223> OTHER INFORMATION: isomir

<400> SEQUENCE: 393
aucuuugguu aucuagcugu auga                                          24

<210> SEQ ID NO 394
<211> LENGTH: 18
<212> TYPE: RNA
<213> ORGANISM: Artificial
<220> FEATURE:
<223> OTHER INFORMATION: isomir

<400> SEQUENCE: 394
cuuugguuau cuagcugu                                                 18

<210> SEQ ID NO 395
<211> LENGTH: 25
```

```
<212> TYPE: RNA
<213> ORGANISM: Artificial
<220> FEATURE:
<223> OTHER INFORMATION: isomir

<400> SEQUENCE: 395
ucuuugguua ucuagcugua ugagu                                          25

<210> SEQ ID NO 396
<211> LENGTH: 21
<212> TYPE: RNA
<213> ORGANISM: Artificial
<220> FEATURE:
<223> OTHER INFORMATION: isomir

<400> SEQUENCE: 396
aucuuugguu aucuagcugu a                                              21

<210> SEQ ID NO 397
<211> LENGTH: 21
<212> TYPE: DNA
<213> ORGANISM: Artificial
<220> FEATURE:
<223> OTHER INFORMATION: oligonucleotide

<400> SEQUENCE: 397
ccggaaaucu ggagaaucat t                                              21

<210> SEQ ID NO 398
<211> LENGTH: 21
<212> TYPE: DNA
<213> ORGANISM: Artificial
<220> FEATURE:
<223> OTHER INFORMATION: oligonucleotide

<400> SEQUENCE: 398
ugauucucca gauuuccggt t                                              21
```